(12) United States Patent
Hopper et al.

(10) Patent No.: US 11,518,761 B2
(45) Date of Patent: Dec. 6, 2022

(54) CDPK1 INHIBITORS, COMPOSITIONS, AND METHODS RELATED THERETO

(71) Applicants: Vyera Pharmaceuticals, LLC, New York, NY (US); Washington University, St. Louis, MO (US)

(72) Inventors: Allen T. Hopper, Lexington, MA (US); L. David Sibley, University City, MO (US); James W. Janetka, St. Louis, MO (US); Jon Helander, St. Louis, MO (US)

(73) Assignees: Vyera Pharmaceuticals, LLC, New York, NY (US); Washington University, St. Louis, MO (US)

( * ) Notice: Subject to any disclaimer, the term of this patent is extended or adjusted under 35 U.S.C. 154(b) by 93 days.

(21) Appl. No.: 16/639,507

(22) PCT Filed: Aug. 17, 2018

(86) PCT No.: PCT/US2018/000285
§ 371 (c)(1),
(2) Date: Feb. 14, 2020

(87) PCT Pub. No.: WO2019/036001
PCT Pub. Date: Feb. 21, 2019

(65) Prior Publication Data
US 2021/0032240 A1    Feb. 4, 2021

Related U.S. Application Data

(60) Provisional application No. 62/546,921, filed on Aug. 17, 2017.

(51) Int. Cl.
*C07D 471/04* (2006.01)
(52) U.S. Cl.
CPC .................................. *C07D 471/04* (2013.01)
(58) Field of Classification Search
CPC .................................................. C07D 471/04
See application file for complete search history.

(56) References Cited

U.S. PATENT DOCUMENTS

| | | | |
|---|---|---|---|
| 5,593,997 | A | 1/1997 | Dow et al. |
| 8,697,709 | B2 | 4/2014 | Dar et al. |
| 2010/0331297 | A1 | 12/2010 | Bulawa et al. |
| 2011/0275651 | A1 | 11/2011 | Dar et al. |
| 2012/0077827 | A1 | 3/2012 | Ibrahim et al. |
| 2013/0018040 | A1 | 1/2013 | Van Voorhis et al. |
| 2021/0032240 | A1 | 2/2021 | Hopper et al. |
| 2021/0115047 | A1 | 4/2021 | Hopper |
| 2021/0347780 | A1 | 11/2021 | Hopper et al. |

FOREIGN PATENT DOCUMENTS

| | | |
|---|---|---|
| WO | WO-2004/056830 A1 | 7/2004 |
| WO | WO-2006/068760 A2 | 6/2006 |
| WO | WO-2009/062118 A2 | 5/2009 |
| WO | WO-2010/045542 A2 | 4/2010 |
| WO | WO-2011/153553 A2 | 12/2011 |
| WO | WO-2013/010136 A2 | 1/2013 |
| WO | WO-2017/161344 A1 | 9/2017 |
| WO | WO-2018/170236 A1 | 9/2018 |
| WO | WO-2019/036001 A1 | 2/2019 |
| WO | WO-2020/061279 A1 | 3/2020 |

OTHER PUBLICATIONS

Extended European Search Report for EP Application No. 18846012.5 dated Dec. 1, 2020.
Extended European Search Report for EP Application No. EP 18767756 dated Nov. 18, 2020.
Janetka et al., "Optimizing pyrazolopyrimidine inhibitors of calcium dependent protein kinase 1 for treatment of acute and chronic toxoplasmosis," Journal of Medicinal Chemistry: 69 pages (2020).
RN 1151650-86-0, registry database compound (2009).
RN 1349721-69-2, registry database compound (2011).
RN 1369538-12-4, registry database compound (2012).
RN 1369538-14-6, registry database compound (2012).
RN 1772577-05-5, registry database compound (2015).
International Search Report and Written Opinion for International Application No. PCT/US2018/000285 dated Dec. 18, 2018.
International Search Report and Written Opinion for International Application No. PCT/US2018/022595 dated Jun. 7, 2018.
International Search Report and Written Opinion for International Application No. PCT/US2019/051877 dated Dec. 22, 2019.
Kuhlenschmidt et al., "Inhibition of Calcium-Dependent Protein Kinase 1 (CDPK1) In Vitro by Pyrazolopyrimidine Derivatives Does Not Correlate with Sensitivity of Cryptosporidium parvum Growth in Cell Culture," Antimicrob. Agents Chemother, 60(1):570-579 (2016).
Larson et al., "Multiple determinants for selective inhibition of apicomplexan calcium-dependent protein kinase CDPK1," J Med Chem 55:2803-2810 (2012).
Lourido et al., "Optimizing Small Molecule Inhibitors of Calcium-Dependent Protein Kinase 1 to Prevent Infection by Toxoplasma Gondii," J Med Chem 56(7):3068-3077 (2013).

(Continued)

*Primary Examiner* — Alicia L Otton
(74) *Attorney, Agent, or Firm* — Foley Hoag LLP; Lucas P. Watkins

(57) ABSTRACT

The invention relates to inhibitors of calcium-dependent protein kinase 1 (CDPK1) and pharmaceutical preparations thereof. The invention further relates to methods of treatment of parasitic infections, such as *T. gondii*, *P. falciparum*, *C. hominis*, or *C. parvum* infections, using the novel inhibitors of the invention.

21 Claims, No Drawings

(56) References Cited

OTHER PUBLICATIONS

Okuzumi et al., "Synthesis and Evaluation of Indazole Based Analog Sensitive Akt Inhibitors," Mol Biosys 6(8):1389-1402 (2010).
Rutaganira et al., "Inhibition of calcium dependent protein kinase 1 (CDPKI1) by pyrazolopyrimidine analogs decreases establishment and reoccurrence of central nervous system disease by Toxoplasma gondii," J Med Chem 60(24):9976-9989 (2017).
Traxler et al., "Use of a Pharmacophore Model for the Design of EGF-R Tyrosine Kinase Inhibitors: 4-(Phenylamino)pyrazolo[3,4-d]pyrimidines," J Med Chem, 40(22):3601-3616 (1997).

CDPK1 INHIBITORS, COMPOSITIONS, AND METHODS RELATED THERETO

RELATED APPLICATIONS

This application is the U.S. National Phase of International Patent Application No. PCT/US2018/00285, filed Aug. 17, 2018, which claims the benefit of priority to U.S. Provisional Patent Application No. 62/546,921, filed on Aug. 17, 2017, each of which is hereby incorporated by reference in its entirety.

BACKGROUND OF THE INVENTION

The phylum Apicomplexa contains parasites that are the causative agents for many serious human and animal diseases. Apicomplexans have complex life cycles sometimes existing in a single host and in other cases alternating between hosts. In the case of *Toxoplasma gondii* (*T. gondii*), cats transmit the disease by shedding infectious oocysts, which can contaminate food and water. Herbivorous hosts such as agricultural animals are also susceptible and in such animals infection culminates in the formation of long-lived tissue cysts that characterize chronic infections. Humans can become infected by ingesting oocysts found in contaminated water or by eating undercooked meat that contains tissue cysts. Although many strains of *T. gondii* are non-pathogenic, infection with some isolates is associated with severe infection in immunocompetent individuals. In some regions of the world, notably South America, toxoplasmosis can lead to severe eye disease and loss of vision.

Other human pathogens within the Apicomplexa include *Plasmodium* spp., (e.g. *Plasmodium falciparum, Plasmodium vivax*), *Babesia* spp. (e.g. *Babesia microti, Babesia bigemina*), *Cyclospora cayetanensis, Isospora belli, Sarcocystis neurona,* and *Cryptosporidium* spp. (e.g., *Cryptosporidium parvum* or *Cryptosporidium hominis*), which cause malaria, toxoplasmosis, babesiosis, cyclosporiasis, isosporiasis, sarcocystosis, and cryptosporidiosis respectively). As well, there are a number of apicomplexan parasites that cause serious economic loss in agricultural animals including *Eimeria* spp., the causative agent of coccidiosis, and *Sarcocystis* spp., which causes Equine Protozoal Myeloencephalitis, as well as parasites that cause disease in companion animals such as *Neospora caninum* that causes neosporosis in dogs. Treatment options for all of these infections are severely limited.

Existing treatments for toxoplasmosis include administration of pyrimethamine, usually in combination with a dihydropteroate synthase (DHPS) sulfonamide inhibitor (e.g., sulfadiazine) to improve efficacy and the tetrahydrofolate folinic acid also called leucovorin to improve tolerability. Allergic reactions to sulfonamide drugs are common and therefore some patients are not able to receive the combination therapy. Pyrimethamine treatment may cause severe side-effects and toxicity, including nausea, vomiting, leukopenia, bone marrow toxicity, teratogenicity and central nervous system toxicity.

In addition, the existing treatments for toxoplasmosis do not eradicate chronic infection, which posses the major risk in immunocompromised patients. Approximately 1-2 billion people are estimated to be chronically infected worldwide. Thus, there is a need for new treatments for acute and chronic toxoplasmosis. Likewise, there is a need for new treatments for infections with *Plasmodium* spp., *Babesia* spp., *Cryptosporidium* spp., *Eimeria* spp., *Cyclospora cayetanensis, Isospora belli, Sarcocystis neurona,* and *Neospora caninum*.

SUMMARY OF THE INVENTION

In certain embodiments, the present invention relates to compounds having the structure of formula (I):

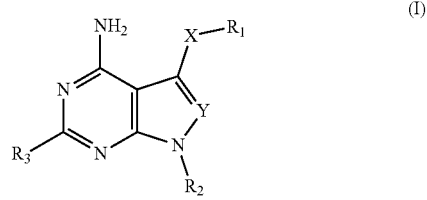

wherein:
X is $R^6$, O, S, $(NR^4)$, $OR^6$, $SR^6$, or $(NR^4)R^6$;
Y is N or CH;
$R^1$ is $C_{6-10}$ aryl or 5-10 member heteroaryl;
$R^2$ is $C_{3-6}$ cycloalkyl;
$R^3$ is H, $C_{1-6}$ alkyl, $C_{1-6}$ haloalkyl, $C_{3-6}$ cycloalkyl;
$R^4$ is H or $C_{1-6}$ alkyl; and
$R^6$ is $C_{1-6}$ alkylene or $C_{1-6}$ alkenylene;
or a pharmaceutically acceptable salt thereof.

The invention further relates to pharmaceutical compositions of such compounds, as well as methods of using such compounds to treat infections (e.g., parasitic infections, such as *Plasmodium* spp., (e.g. *Plasmodium falciparum, Plasmodium vivax*), *Babesia* spp. (e.g. *Babesia microti, Babesia bigemina*), *Cyclospora cayetanensis, Isospora belli, Sarcocystis neurona,* and *Cryptosporidium* spp. (e.g., *Cryptosporidium parvum* or *Cryptosporidium hominis*), which cause malaria, toxoplasmosis, babesiosis, cyclosporiasis, isosporiasis, sarcocystosis, and cryptosporidiosis respectively).

DETAILED DESCRIPTION OF THE INVENTION

In some aspects, the present invention relates to compounds having the structure of formula (I):

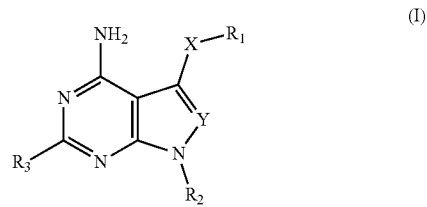

wherein:
X is $R^6$, O, S, $(NR^4)$, $OR^6$, $SR^6$, or $(NR^4)R^6$;
Y is N or CH;
$R^1$ is $C_{6-10}$ aryl or 5-10 member heteroaryl;
$R^2$ is $C_{3-6}$ cycloalkyl;
$R^3$ is H, $C_{1-6}$ alkyl, $C_{1-6}$ haloalkyl, $C_{3-6}$ cycloalkyl;
$R^4$ is H or $C_{1-6}$ alkyl; and
$R^6$ is $C_{1-6}$ alkylene or $C_{1-6}$ alkenylene;
or a pharmaceutically acceptable salt thereof.

In certain embodiments, X is $R^6$. In certain embodiments, X is $OR^6$, $SR^6$, or $(NR^4)R^6$. In certain preferred embodiments, X is O, S, or $(NR^4)$. In further preferred embodiments, X is O.

In certain embodiments, $R^1$ is unsubstituted.

In certain embodiments, $R^1$ is substituted with one or more $R^5$; and each $R^5$ is independently selected from alkyl, such as haloalkyl, cycloalkyl, halo, hydroxyl, oxo, alkoxy, cycloalkyloxy, amino, amidine, imine, cyano, azido, sulfhydryl, alkylthio, heterocyclyl, aryl, and heteroaryl. In certain embodiments, each $R^5$ is independently selected from $C_{1-3}$ alkyl, $C_{1-3}$ alkoxy, $C_{1-3}$ haloalkyl, cyano, and halo. In certain embodiments, each $R^5$ is independently selected from $C_{1-3}$ alkyl, $C_{1-3}$ haloalkyl, and halo. In certain preferred embodiments, each $R^5$ is independently selected from methyl, trifluoromethyl, cyano, chloro, and fluoro. In certain preferred embodiments, each $R^5$ is independently selected from methyl, trifluoromethyl, chloro, and fluoro.

In certain embodiments, $R^1$ is substituted with aryl, heteroaryl, cycloalkyl, or heterocyclyl. In certain embodiments, $R^1$ is substituted with phenyl, pyridyl, pyrimidinyl, pyridazinyl, pyrazinyl, azaindolyl, quinolinyl, isoquinolinyl, piperidinyl, piperazinyl, tetrahydropyranyl, or dihydropyranyl. In certain embodiments, $R^1$ is substituted with phenyl, pyridyl, pyrimidinyl, pyridazinyl, pyrazinyl, azaindolyl, quinolinyl, isoquinolinyl, piperidinyl, piperazinyl, tetrahydropyranyl, or dihydropyranyl. In certain preferred embodiments, $R^1$ is substituted with tetrahydropyranyl, or dihydropyranyl.

In certain embodiments, $R^1$ is phenyl, and is optionally substituted as described above. In certain preferred embodiments, $R^1$ is phenyl substituted at the meta-position with $R^5$. In certain preferred embodiments, $R^1$ is 3-chlorophenyl, 3-cyanophenyl, 3-fluorophenyl, 3-trifluoromethylphenyl or 3 methoxyphenyl.

In certain embodiments, $R^1$ is a 6 member heteroaryl (such as pyridinyl, pyrimidinyl, pyridazinyl, pyrazinyl), and is optionally substituted as described above. In certain preferred embodiments, $R^1$ is pyrazine, and is optionally substituted as described above. In certain preferred embodiments, $R^1$ is pyridin-2-yl substituted at the 4-position with $R^5$. In certain preferred embodiments, $R^1$ is pyridin-2-yl substituted at the 4-position with $R^5$, wherein $R^5$ is not chloro. In certain preferred embodiments, $R^1$ is pyridin-2-yl substituted at the 4-position with $R^5$, wherein $R^5$ is trifluoromethyl, cyano, or hydroxyl. In certain preferred embodiments, $R^1$ is 4-fluoropyridin-2-yl, 4-chloropyridin-2-yl, 4-cyanopyridin-2-yl, 4-trifluoromethylpyridin-2-yl, or 4-methoxypyridin-2-yl.

In certain embodiments, $R^1$ is a 9 member heteroaryl. In certain preferred embodiments, $R^1$ is indolyl (such as indol-3-yl) or azaindolyl (such as 7-aza-indol-3-yl or 5-azaindol-6-yl), and is optionally substituted as described above. In certain preferred embodiments, $R^1$ is 6-fluoroindol-3-yl, 5-fluoro-7-azaindol-3-yl and 5-fluoroindol-3-yl.

In certain embodiments, $R^2$ is unsubstituted.

In certain embodiments, $R^2$ is substituted with one or more $R^7$, and each $R^7$ is independently selected from alkyl, such as haloalkyl, cycloalkyl, halogen, hydroxyl, oxo, alkoxy, cycloalkyloxy, cyano, alkylthio. In certain embodiments, each $R^7$ is independently selected from $C_{1-3}$ alkyl, $C_{1-3}$ haloalkyl, hydroxyl, or halo. In certain embodiments, each $R^7$ is independently selected from $C_{1-3}$ alkyl, $C_{1-3}$ haloalkyl, or halo. In certain preferred embodiments, each $R^7$ is independently selected from methyl, trifluoromethyl, hydroxyl, chloro, or fluoro. In certain preferred embodiments, each $R^7$ is independently selected from methyl, trifluoromethyl, chloro, or fluoro. In certain preferred embodiments, each $R^7$ is fluoro.

In certain embodiments, the $R^7$ substituent has a cis configuration relative to the pyrazolo[3,4-d]pyrimidine core.

In certain embodiments, the $R^7$ substituent has a trans configuration relative to the pyrazolo[3,4-d]pyrimidine core.

In certain preferred embodiments, $R^2$ is cyclopropyl or cyclobutyl. In certain preferred embodiments, $R^2$ is cyclopropyl, such as unsubstituted cyclopropyl. In certain preferred embodiments, $R^2$ is cyclobutyl.

In certain embodiments, $R^2$ is cyclopropyl or cyclobutyl, substituted by one or more $R^7$ selected from trifluoromethyl, carboxyl, and ester. In certain embodiments, $R^7$ is alkyl ester, such as $C_{1-3}$ alkyl ester.

In certain preferred embodiments, $R^2$ is hydroxycyclobutyl (such as cis-3-hydroxycyclobutyl or trans-3-hydroxycyclobutyl), fluorocyclobutyl (such as cis-3-fluorocyclobutyl or trans-3-fluorocyclobutyl), difluorocyclobutyl (such as 3,3-difluorocyclobutyl), or oxocyclobutyl (such as 3-oxo-cyclobutyl).

In certain preferred embodiments, $R^2$ is selected from hydroxycyclopropyl (such as cis-hydroxycyclopropyl or trans-hydroxycyclopropyl), fluorocyclopropyl (such as cis-fluorocyclopropyl or trans-fluorocyclopropyl), or difluorocyclopropyl (such as 2,2-difluorocyclopropyl).

In certain embodiments, $R^3$ is H, $C_{1-3}$ alkyl, trifluoromethyl, or cyclopropyl. In certain preferred embodiments, $R^3$ is H.

In certain embodiments, $R^4$ is H or $C_{1-3}$ alkyl.

In certain embodiments, $R^6$ is methylene, ethylene, or ethenylene. In certain embodiments, $R^6$ is absent. In certain preferred embodiments, $R^6$ is methylene.

In certain preferred embodiments, Y is CH.

In certain preferred embodiments, the present disclosure provides compounds of formula (Ia):

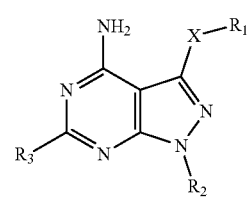

(Ia)

wherein X is $R^6$, O, S, or $(NR^4)$; $R^1$ is phenyl optionally substituted with one or more $R^5$ independently selected from $C_{1-3}$ alkyl, $C_{1-3}$ haloalkyl, cyano, or halo; R is $C_{3-4}$ cycloalkyl substituted with one or more $R^7$ selected from hydroxyl or fluoro; $R^3$ is H; $R^4$ is H or $C_{1-6}$ alkyl; and $R^6$ is $C_{1-3}$ alkylene; or a pharmaceutically acceptable salt thereof. In certain embodiments, $R^1$ is chlorophenyl. $R^1$ is 2-chlorophenyl. In certain embodiments, the compound is:

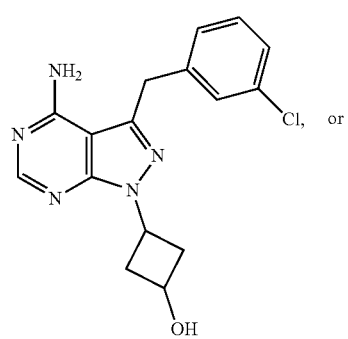

or

-continued

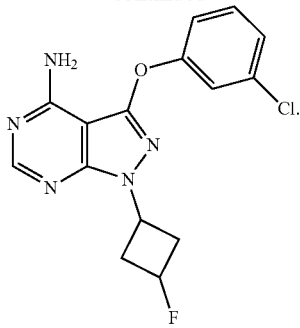
5

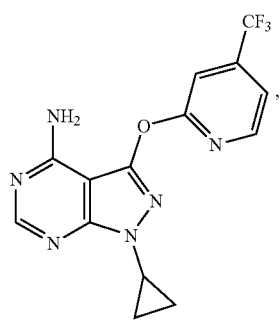

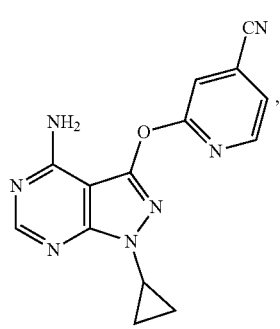

In certain such embodiments, the compound is a cis or trans isomer of such compounds.

In certain preferred embodiments, the present disclosure provides compounds of formula (Ib):

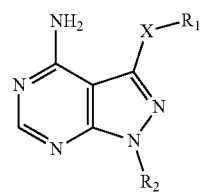
(Ib)

wherein X is $R^6$, O, S, or ($NR^4$), preferably O; $R^1$ is pyridin-2-yl substituted at the 4-position with one $R^5$ selected as described with respect to formula (I); $R^2$ is $C_{3-4}$ cycloalkyl; $R^4$ is H or $C_{1-6}$ alkyl; and $R^6$ is $C_{1-3}$ alkylene; or a pharmaceutically acceptable salt thereof. In certain preferred embodiments, $R^5$ is not 4-fluoro. In certain preferred embodiments, $R^5$ is selected from $C_{1-3}$ alkyl (such as $C_{1-3}$ haloalkyl), $C_{1-3}$ alkoxy (such as $C_{1-3}$ haloalkoxy), halogen, or cyano. In certain preferred embodiments, $R^5$ is selected from $C_{1-3}$ alkyl (such as $C_{1-3}$ haloalkyl), $C_{1-3}$ alkoxy (such as $C_{1-3}$ haloalkoxy), or cyano.

In certain embodiments, $R^2$ is selected from hydroxycyclobutyl, fluorocyclobutyl, difluorocyclobutyl, oxocyclobutyl, hydroxycyclopropyl, fluorocyclopropyl, or difluorocyclopropyl. Alternatively, $R^2$ may be unsubstituted cyclopropyl. In other embodiments, $R^2$ is cyclopropyl or cyclobutyl, substituted by one or more $R^7$ selected from trifluoromethyl, carboxyl, and ester. In certain embodiments, $R^7$ is alkyl ester, such as $C_{1-3}$ alkyl ester.

In certain embodiments, the $R^7$ substituent has a cis configuration relative to the pyrazolo[3,4-d]pyrimidine core.

In certain embodiments, the $R^7$ substituent has a trans configuration relative to the pyrazolo[3,4-d]pyrimidine core.

In certain preferred embodiments, $R^1$ is 4-(trifluoromethyl)pyridin-2-yl, 4-fluoropyridin-2-yl or 4-cyanopyridin-2-yl. In certain embodiments, the compound is:

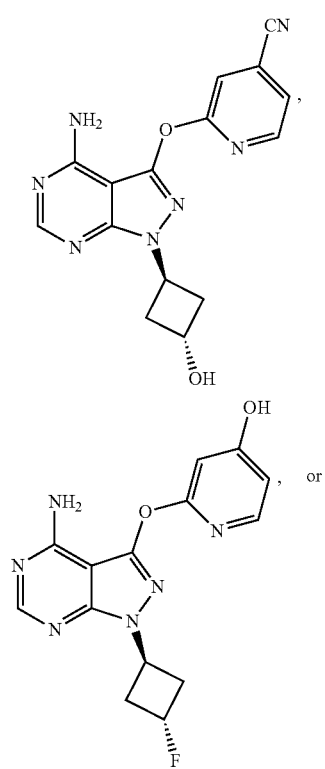

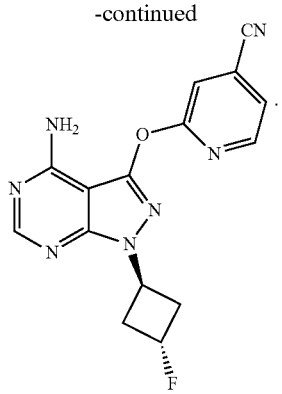

In certain such embodiments, the compound is a cis or trans isomer of such compounds.

In another aspect, the present invention relates to a pharmaceutical composition comprising a compound as disclosed herein.

In yet another aspect, the present invention relates to a method of preventing or inhibiting the growth or proliferation of a microorganism using a compound of formula (I). In certain embodiments, the microorganism is a protozoan. In certain embodiments, the microorganism is a protozoan. In certain embodiments, the protozoan is an Apicomplexan, for instance of genera *Toxoplasma, Cryptosporidium*, or *Plasmodium*. In certain embodiments, the microorganism is *T. gondii*, or is of genera *Cryptosporidium* or *Plasmodium*. In certain preferred embodiments, the microorganisms are *T. gondii, P. falciparum, C. hominis*, or *C. parvum*.

In certain embodiments inhibiting the growth or proliferation of a microorganism comprises applying a compound having the structure of formula (I) to a location. The compound may be applied in the form of a spray (e.g., from a spray bottle) or by wiping (e.g., with a pre-soaked wipe, a mop, or a sponge). In certain embodiments, the location is one where the microorganism is known or suspected to be present. In certain embodiments, the location is one that is at risk for the presence of the microorganism. In certain embodiments, the compound of formula (I) is applied prophylactically. In certain embodiments, the compound of formula (I) is applied after suspected contamination by the protozoan. In certain embodiments, the location may be a surface, such as a cooking surface or a surface that has contact with material suspected of containing the microorganism, such as a surface that has had contact with raw meat or animal (such as cat) feces. In certain embodiments, the cooking surface is a cutting board, a counter, or a utensil, such as a knife or fork. In certain embodiments, the location may be the surface or interior of a food, such as a meat or a vegetable. In certain embodiments, the location may be a liquid, such as water, for instance drinking water. In certain embodiments, the location may be soil. In certain embodiments, the location may be a place where a cat has defecated or will defecate, or an area where cat feces or cat litter is likely to spread or to have been spread. In further embodiments, the location is a litterbox or the area around a litterbox. In certain embodiments, the location is a body surface, such as a hand.

In certain embodiments, the compound of formula (I) is used to prevent transmission of the microorganism between people and/or animals. In further embodiments, the transmission is congenital transmission. In further embodiments, the compound of formula (I) is administered to a mother, administered to an infant, applied to the skin of the mother, or applied to the skin of the infant. In certain embodiments, the compound of formula (I) is applied to blood, such as blood intended for transfusion. In certain embodiments, the compound of formula (I) is applied to an organ, such as an organ intended for transplant. In certain embodiments, the compound of formula (I) is administered to an organ donor prior to transplant. In certain embodiments, the compound of formula (I) is administered to an animal, such as a cat or a mouse.

In yet another aspect, the present invention relates to a method of treating an infection, comprising administering a compound having the structure of formula (I), a pharmaceutically acceptable salt or prodrug thereof, or a pharmaceutical composition comprising such a compound, salt, or prodrug. In certain embodiments, the infection is caused by a protozoan. In certain embodiments, the protozoan is an Apicomplexan, for instance of genera *Toxoplasma, Cryptosporidium*, or *Plasmodium*. In certain embodiments, the microorganism is *T. gondii*, or is of genera *Cryptosporidium* or *Plasmodium*. In certain preferred embodiments, the microorganisms are *T. gondii, P. falciparum, C. hominis*, or *C. parvum*.

In yet another aspect, the present invention relates to one of the compounds or compositions disclosed herein, a pharmaceutically acceptable salt or prodrug thereof, or a pharmaceutical composition comprising such a compound, salt, or prodrug, for use in the treatment of an infection. In certain embodiments, the infection is caused by a protozoan, such as an Apicomplexan protozoan. In certain embodiments, the protozoan is of genus *Toxoplasma, Cryptosporidium*, or *Plasmodium*. In certain embodiments, the protozoan is an Apicomplexan, for instance of genera *Toxoplasma, Cryptosporidium*, or *Plasmodium*. In certain embodiments, the microorganism is *T. gondii*, or is of genera *Cryptosporidium* or *Plasmodium*. In certain preferred embodiments, the microorganisms are *T. gondii, P. falciparum, C. hominis*, or *C. parvum*.

In still another aspect, the present invention relates to a compound having the structure of formula (I), a pharmaceutically acceptable salt or prodrug thereof, or a pharmaceutical composition comprising such a compound, salt, or prodrug for use in the treatment of an infection.

DISCUSSION

Apicomplexans contain from 6-11 related calcium dependent protein kinases (CDPKs), depending on the species. In addition to TgCDPK1, which controls invasion and egress, TgCDPK2 and TgCPDK6 have also been shown to play essential roles in bradyzoite development and cell division, respectively. CDPKs differ substantially in their ATP binding pocket from human kinases. In particular, CDPK1 from *Toxoplasma gondii, Neospora caninum, Sarcocystis neurona*, and *Cryptosporidium* spp. contain a glycine gatekeeper, predicting that they will be sensitive to the compounds described herein. Other CDPKs contain different substitutions in their ATP binding pocket, and they may also be targeted by the inhibitors described herein. *Plasmodium* also contains a number of CDPKs that are important in infection of red blood cells, as well as development in the mosquito during transmission. Additional roles for CDPKs in related parasites may be defined by future studies and some of these enzymes may also be inhibited by the compounds described herein.

The compounds disclosed herein inhibit CDPK1, and can prevent or ameliorate infections, including toxoplasmosis.

In certain embodiments, the compounds herein preferentially inhibit protozoan CDPK1 relative to other human kinases. In certain embodiments, the protozoan is an Apicomplexan, for instance of genera *Toxoplasma, Cryptosporidium*, or *Plasmodium*. In certain embodiments, the microorganism is *T. gondii*, or is of genera *Cryptosporidium* or *Plasmodium*. In certain preferred embodiments, the microorganisms are *T. gondii, P. falciparum, C. hominis*, or *C. parvum* In certain such embodiments, the selectivity of the compounds herein for protozoan CDPK1 (such as *T. gondii, P. falciparum, C. hominis*, or *C. parvum*) versus human SRC kinase (as determined by the ratio of the compound's $IC_{50}$ against each enzyme) is greater than 3-fold, greater than 10-fold, greater than 30-fold, greater than 50-fold, greater than 75-fold, greater than 100-fold, or greater than 300-fold. In certain embodiments, the compounds herein have an $IC_{50}$ for protozoan CDPK1 (such as *T. gondii, P. falciparum, C. hominis*, or *C. parvum*) less than 3000, less than 1500, less than 1000 nM, or less than 300, preferably less than 100 nM or less than 30 nM. In certain embodiments, the selectivity of the compounds herein for *T. gondii, P. falciparum, C. hominis*, or *C. parvum* versus human SRC kinase (as determined by the ratio of the compound's $IC_{50}$ against each kinase) is greater than 3-fold, greater than 10-fold, greater than 30-fold, greater than 50-fold, greater than 75-fold, greater than 100-fold, or greater than 300-fold. In certain embodiments, the compounds herein have an $IC_{50}$ for *T. gondii, P. falciparum, C. hominis*, or *C. parvum* CDPK1 of less than 1000 nM or less than 100 nM, preferably less than 10 nM.

In certain embodiments, compounds of the invention may be prodrugs of the compounds disclosed herein, e.g., wherein a hydroxyl in the parent compound is presented as an ester or a carbonate, or a carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomers. For example, a compound of the invention may have greater than 30% de, 40% de, 50% de, 60% de, 70% de, 80% de, 90% de, or even 95% or greater de.

In certain embodiments, the present invention relates to methods of treatment with a compound disclosed herein, or a pharmaceutically acceptable salt thereof. In certain embodiments, the therapeutic preparation may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

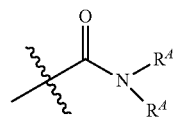

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

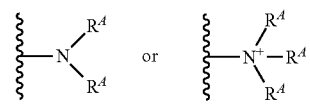

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

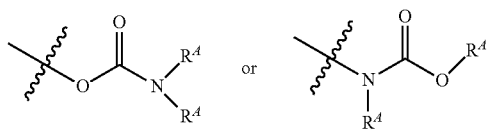

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included-in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^A$, wherein R$^A$ represents a hydrocarbyl group.

The term "carboxy", as used herein, refers to a group represented by the formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

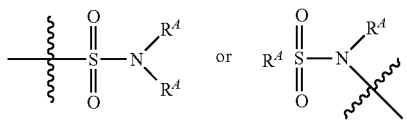

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^A$, wherein $R^A$ represents a hydrocarbyl.

The term "thioalkyl", as used herein, refers to an alkyl group substituted with a thiol group.

The term "thioester", as used herein, refers to a group —C(O)S$R^A$ or —SC(O)$R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

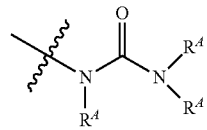

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions; are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

Use of CDPK1 Inhibitors

Another embodiment of the invention is the use of the compounds described herein for the treatment of infections (e.g., parasitic infections, such as toxoplasmosis). In certain embodiments, the compounds described herein may be used conjointly with other compounds useful for that purpose, such as sulfadiazene, sulfamethoxazole, clindamycin, spiramycin, atovaquone, DHFR inhibitors, or cytochrome $BC_1$ inhibitors.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15)-alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base-, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial; intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general:

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, L-ascorbic acid, L-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, D-glucoheptonic acid, D-gluconic acid, D-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, L-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, L-pyroglutamic acid, salicylic acid, sebacic acid, stearic acid, succinic acid, sulfuric acid, L-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

Example 1: General Methods

NMR spectra were recorded on a Varian 400 MHz for $^1$H NMR. LCMS were taken on a quadrupole Mass Spectrometer on Shimadzu LCMS 2010 (Column: sepax ODS 50×2.0 mm, 5 um) or Agilent 1200 HPLC, 1956 MSD (Column: Shim-pack XR-ODS 30×3.0 mm, 2.2 um) operating in ES (+) ionization mode.

Example 2: Synthetic Methods

Synthesis Method A: The General Procedure of Method a is Represented by the Preparation of 3-(3-chlorobenzyl)-1-cyclopropyl-1H-pyrazolo[3,4-d]pyrimidin-4-amine ($R_1$ is Cyclopropyl and $R^2$ is-3-chlorophenyl)

Synthetic Scheme 1 representing Method A.

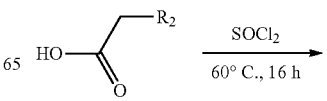

Step 1

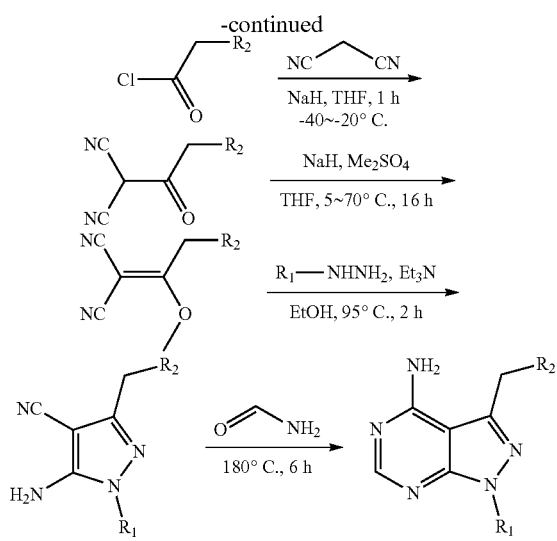

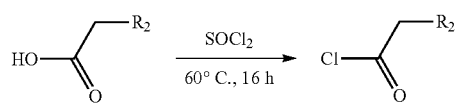

A solution of 2-(3-chlorophenyl)acetic acid (50.0 g, 293.1 mmol, 1.0 eq) in SOCl₂ (300.0 mL) was stirred at 60° C. for about 16 h. TLC (Petroleum ether/Ethyl acetate=3/1) showed the starting material was consumed completely (quenched by methanol). Then the mixture was concentrated by rotary evaporator to give 2-(3-chlorophenyl)acetyl chloride (55.4 g, crude) as light yellow liquid.

Step 2

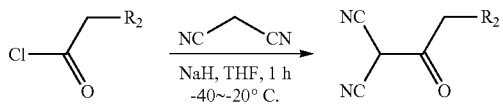

To a solution of propanedinitrile (19.4 g, 293.1 mmol, 1.0 eq) in THF (500.0 mL) was added NaH (14.1 g, 351.7 mmol, 60% purity, 1.2 eq) in portions at −40° C.~−20° C., stirred for about 20 min and then a solution of 2-(3-chlorophenyl) acetyl chloride (55.4 g, crude, 1.0 eq) in THF (500.0 mL) was added while maintaining the temperature between −40° C. and −20° C. Stirring continued at this temperature for about 40 min. TLC (petroleum ether/ethyl acetate=2/1; product R$_f$=0.4) indicated the reaction was complete, and the reaction was quenched by addition of 1 L of water, extracted with 3×500 mL of ethyl acetate and the combined organic fractions were dried (sodium sulfate) and concentrated. Purification by column chromatography (SiO₂, Petroleum ether/Ethyl acetate=5/1 to 2/1) provided 2-(2-(3-chlorophenyl)acetyl)malononitrile (21.0 g, 96.0 mmol, 32.8% yield) as red oil.

Step 3

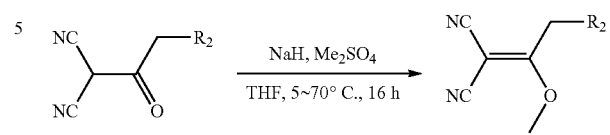

To a solution of 2-(2-(3-chorophenyl)acetyl)malononitrile (6.7 g, 30.5 mmol, 1.0 eq) in THF (70.0 mL) was added NaH (1.8 g, 45.8 mmol, 60% purity, 1.5 eq) in portions at 5° C. After stirring at 5° C. for about 15 min, Me₂SO₄ (15.4 g, 122.0 mmol, 4.0 eq) was added dropwise and then the reaction mixture was heated to 70° C. for about 16 h. The reaction was quenched by addition of 300 mL of water, extracted with 3×200 mL of ethyl acetate and the combined organic fractions were dried (sodium sulfate) and concentrated. Purification by column chromatography (SiO₂, petroleum ether/ethyl acetate=10/1 to 3/1) provided 2-(2-(3-chlorophenyl)-1-methoxyethylidene)malononitrile (14.0 g, 60.2 mmol, 65.7% yield) as a yellow oil. ¹H NMR (400 MHz, CDCl₃) δ=7.35 (d, J=5.2 Hz, 2H), 7.25 (d, J=9.6 Hz, 1H), 7.16 (t, J=3.6 Hz, 1H), 4.09 (s, 3H), 3.98 (s, 2H).

Step 4

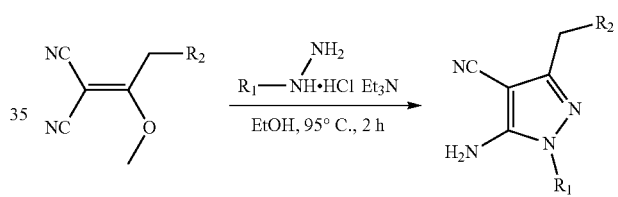

To a mixture of 2-(2-(3-chlorophenyl)-1-methoxyethylidene)malononitrile (4.0 g, 17.2 mmol, 1.0 eq) and cyclopropylhydrazine (3.73 g, 34.4 mmol, 2.0 eq, HCl) in ethanol (50.0 mL) was added triethylamine (6.9 g, 68.7 mmol, 4.0 eq). After stirring at 95° C. for 2 h under nitrogen atmosphere the reaction was deemed complete by TLC (Petroleum ether/Ethyl acetate=1/1; product R$_f$ 0.4) and concentrated under reduced pressure. The residue was purified by column chromatography (SiO₂, Petroleum ether/Ethyl acetate=5/1 to 3/1) to give 5-amino-3-(3-chlorobenzyl)-1-cyclopropyl-1H-pyrazole-4-carbonitrile (4.0 g, 14.6 mmol, 85.3% yield) as a yellow solid. ¹H NMR: (400 MHz, CDCl₃) δ=7.27 (s, 1H), 7.24-7.17 (m, 3H), 4.63 (s, 2H), 3.86 (s, 2H), 3.10-3.05 (m, 1H), 1.14-1.08 (m, 4H).

Step 5

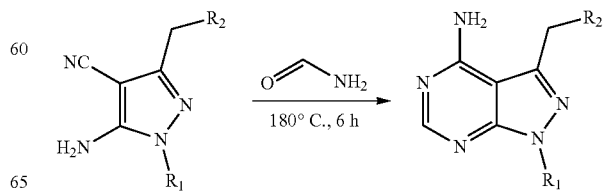

5-Amino-3-(3-chlorobenzyl)-1-cyclopropyl-1H-pyrazole-4-carbonitrile (400.0 mg, 1.5 mmol, 1.0 eq) and formamide (9.0 g, 200.7 mmol, 8.0 mL, 136.8 eq) were stirred at 180° C. for about 6 h. Reaction progress was monitored by TLC (Dichloromethane/Methanol=10/1, $R_f$=0.55) and upon completion, the mixture was poured into about 15 mL of water and extracted with 3×20 mL of ethyl acetate. The combined organic fractions were dried (Na2SO4), concentrated and the remaining residue purified by column chromatography (SiO$_2$, DCM/Methanol 30/1 to 20/1) to provide 420 mg of product as a yellow solid. Further purification of 70 mg crude product by HPLC (condition: neutral) gave 21.4 mg of 3-(3-chlorobenzyl)-1-cyclopropyl-1H-pyrazolo[3,4-d]pyrimidin-4-amine (Compound 1) as a white solid. $^1$H NMR: (400 MHz, CDCl$_3$) δ=8.34 (s, 1H), 7.25 (d, J=1.2 Hz, 2H), 7.20 (s, 1H), 7.09 (d, J=5.6 Hz, 1H), 4.94 (s, 2H), 4.26 (s, 2H), 3.75-3.71 (m, 1H), 1.34-1.30 (m, 2H), 1.19-1.14 (m, 2H). LCMS: (M+H)$^+$: 300.1, Rt: 2.254 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

The following compounds were prepared in a similar manner as for method A using different starting materials.

TABLE 1

Compounds Prepared by Method A

| Compound No. | IUPAC Name | MW | LC/MS Observed (M + H) | $^1$H NMR (400 MHz) |
|---|---|---|---|---|
| 2 | 3-(4-chlorobenzyl)-1-cyclopropyl-1H-pyrazolo[3,4-d]pyrimidin-4-amine | 299.76 | 300.0 | (CHLOROFORM-d) δ = 8.33 (s, 1H), 7.33-7.26 (m, 2H), 7.17-7.14 (m, 2H), 4.91 (s, 2H), 3.74-3.72 (m, 1H), 1.32-1.31 (m, 2H), 1.19-1.16 (m, 2H) |
| 3 | 3-(3-chlorobenzyl)-1-cyclopropyl-1H-pyrazolo[3,4-d]pyrimidin-4-amine | 299.76 | 300.1 | (CHLOROFORM-d) δ = 8.34 (s, 1H), 7.25 (d, J = 1.2 Hz, 2H), 7.20 (s, 1H), 7.09 (d, J = 5.6 Hz, 1H), 4.94 (s, 2H), 4.26 (s, 2H), 3.75-3.71 (m, 1H), 1.34-1.30 (m, 2H), 1.19-1.14 (m, 2H) |
| 4 | 3-(3-chloro-5-fluorobenzyl)-1-cyclopropyl-1H-pyrazolo[3,4-d]pyrimidin-4-amine | 317.75 | 318.1 | (CHLOROFORM-d ) δ = 8.38 (s, 1H), 7.03 (d, J = 6.8 Hz, 2H), 6.82 (d, J = 9.2 Hz, 1H), 4.96 (s, 2H), 4.27 (s, 2H), 3.76 (d, J = 3.6 Hz, 1H), 1.34 (s, 2H), 1.20 (t, J = 6.2 Hz, 2H) |
| 5 | 1-cyclopropyl-3-(3-fluorobenzyl)-1H-pyrazolo[3,4-d]pyrimidin-4-amine | 283.30 | 284.2 | (DMSO-d6) δ = 8.14 (s, 1H), 7.35-7.28 (m, 1H), 7.09-7.02 (m, 2H), 7.02-6.97 (m, 1H), 4.34 (s, 2H), 3.77-3.70 (m, 1H), 3.31-3.28 (m, 2H), 1.15-0.98 (m, 4H) |
| 52 | 3-((4-chloropyridin-2-yl)methyl)-1-cyclopropyl-1H-pyrazolo[3,4-d]pyrimidin-4-amine | 300.1 | 301.1 | (ACETONITRILE-d3 + D2O) δ = 8.45 (d, J = 5.6, 1H), 8.13 (s, 1H), 7.56 (d, J = 1.6 Hz, 1H), 7.37 (d, J = 5.2, 1H), 4.70 (s, 2H), 3.88-3.83 (m, 1H), 1.29-1.20 (m, 4H) |

Synthesis Method B: The General Procedure of Method B is Represented by the Preparation of 3-(3-chlorobenzyl)-1-cyclobutyl-1H-pyrazolo[3,4-d]pyrimidin-4-amine Synthesis Method C: General Procedure Represented by the Preparation of 1-cyclopropyl-3-(3-(pyridin-2-yl)benzyl)-1H-pyrazolo[3,4-d]pyrimidin-4-amine

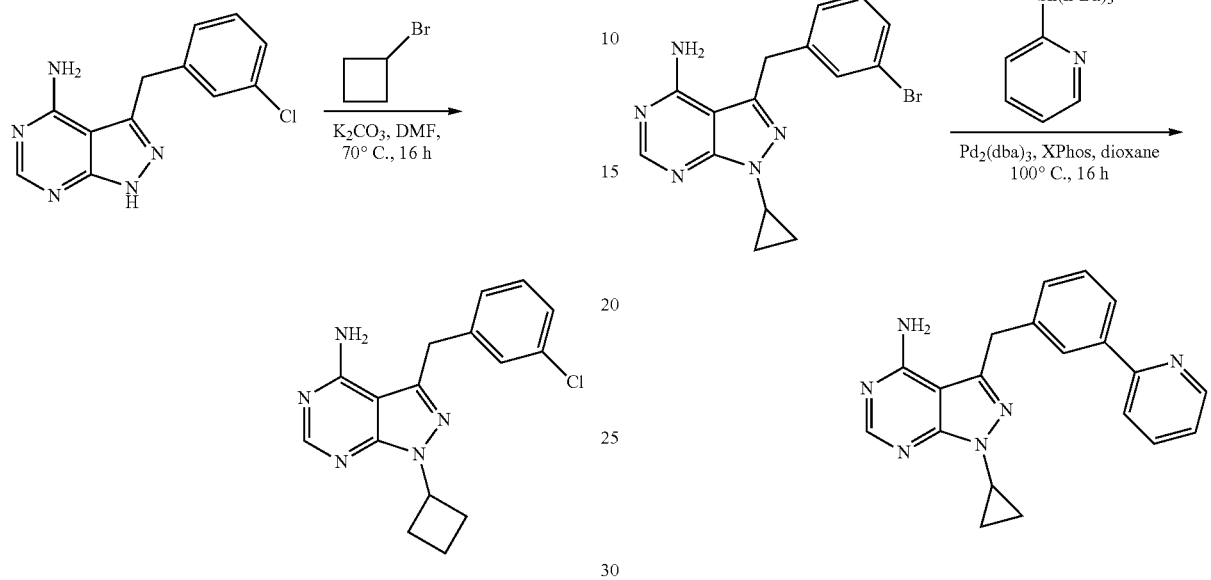

To a suspension of 3-(3-chlorobenzyl)-1H-pyrazolo[3,4-d]pyrimidin-4-amine (100.0 mg, 385.1 μmol, 1.0 eq) and K$_2$CO$_3$ (106.4 mg, 770.1 μmol, 2.0 eq; prepared as described in method A with R1=H) in anhydrous DMF (4.0 mL) under nitrogen was added bromocyclobutane (104.0 mg, 770.1 μmol, 2.0 eq), and the mixture was stirred at 70° C. for 16 h. The reaction mixture was filtered and the filtrate was purified by prep-HPLC (condition: neutral) to give 3-(3-chlorobenzyl)-1-cyclobutyl-1H-pyrazolo[3,4-d]pyrimidin-4-amine (Compound 6) (45.5 mg, 145.0 μmol, 37.7% yield) as an off-white solid, $^1$H NMR: (400 MHz, DMSO-d$_6$) δ=8.13 (s, 1H), 7.36-7.19 (m, 5H), 5.27-5.19 (m, 1H), 4.40 (s, 2H), 2.69-2.62 (m, 2H), 2.36-2.34 (m, 2H), 1.87-1.81 (m, 2H). LCMS: (M+H)$^+$: 314.3, Rt: 2.471 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

The following compound was prepared in a similar manner as for method A using different starting materials.

A mixture of 3-(3-bromobenzyl)-1-cyclopropyl-1H-pyrazolo[3,4-d]pyrimidin-4-amine (100 mg, 290.52 μmol, 1.00 eq), tributyl(2-pyridyl)stannane (106.95 mg, 290.52 μmol, 1.00 eq), Pd$_2$(dba)$_3$ (7.98 mg, 8.72 μmol, 0.03 eq), XPhos (23.54 mg, 49.39 μmol, 0.17 eq) in dioxane (2.00 mL) was stirred at 100° C. for about 16 h under nitrogen atmosphere. The reaction was monitored by LCMS and upon completion the reaction mixture was filtered and the filtrate purified by prep-HPLC (condition: TFA) to give 1-cyclopropyl-3-(3-(pyridin-2-yl)benzyl)-1H-pyrazolo[3,4-d]pyrimidin-4-amine (Compound 7) (16.52 mg, 36.19 μmol, 12.46% yield) as a white solid. $^1$H NMR: (400 MHz, METHANOL-d$_4$) δ=8.73 (d, J=5.2 Hz, 1H), 8.38-8.31 (m, 2H), 8.13 (d, J=8.0 Hz, 1H), 7.87-7.80 (m, 2H), 7.78-7.73 (m, 1H), 7.60-7.54 (t, J=7.6 Hz, 1H), 7.51-7.46 (m, 1H), 4.54 (s, 2H), 3.92 (m, 1H), 1.32-1.22 (m, 2H), 1.20-1.10 (m, 2H). LCMS: Obtained M+H 343.1, expected M+H 343.2. LC/MS conditions (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array

| Compound No. | IUPAC Name | MW | LC/MS Observed (M + H) | 1H NMR (400 MHz) |
|---|---|---|---|---|
| 53 | 3-(3-chlorobenzyl)-1-(3,3-difluorocyclobutyl)-1H-pyrazolo[3,4-d]pyrimidin-4-amine | 349 | 350.1 | (METHANOL-d4) δ = 8.31 (s, 1H), 7.31-7.26 (m, 3H), 7.22 (d, J = 15.6 Hz, 1H), 5.38-5.29 (m, 1H), 4.45 (s, 2H), 3.48-3.32 (m, 2H), 3.18-3.15 (m, 2H) |

(DAD) and evaporative light scattering (ELSD) detection as well as positive electrospray ionization (MS).

Alternative Synthesis Method C: General Procedure Represented by the Preparation of 3-([1,1'-biphenyl]-3-ylmethyl)-1-cyclopropyl-1H-pyrazolo[3,4-d]pyrimidin-4-amine Synthetic Scheme 4 Representing Alternative Method C

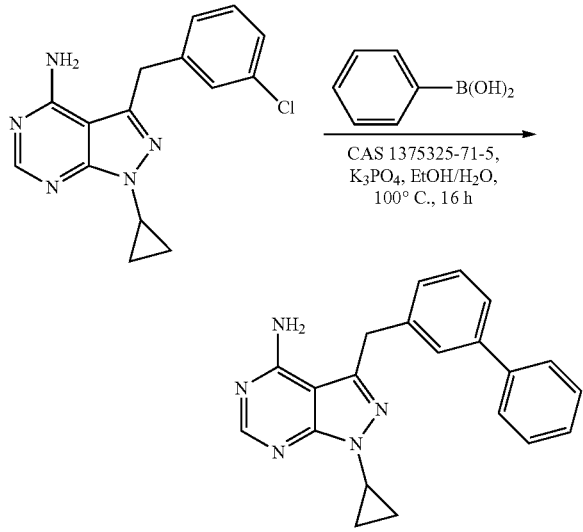

note: CAS: 1375325-71-5 is [2-(2-aminophenyl)phenyl]-chloro-palladium; tritert-butylphosphane A mixture of 3-(3-chlorobenzyl)-1-cyclopropyl-1H-pyrazolo[3,4-d]pyrimidin-4-amine (50.0 mg, 166.8 µmol, 1.0 eq), phenylboronic acid (30.5 mg, 250.2 µmol, 1.5 eq), $K_3PO_4$ (70.8 mg, 333.6 µmol, 2.0 eq), chloro[(tri-tert-butylphosphine)-2-(2-aminobiphenyl)]palladium(II) (CAS: 1375325-71-5) (8.5 mg, 16.7 µmol, 0.1 eq) in ethanol (4.0 mL) and $H_2O$ (1.0 mL) was stirred at 100° C. for about 16 h under nitrogen atmosphere. The mixture was filtered and the filtrate was concentrated by rotary evaporator and the resulting residue was purified by prep-HPLC (condition: neutral) to afford 3-([1,1'-biphenyl]-3-ylmethyl)-1-cyclopropyl-1H-pyrazolo[3,4-d]pyrimidin-4-amine (Compound 8) (23.3 mg, 68.2 µmol, 40.9% yield) as a white solid. $^1$H NMR: (400 MHz, $CDCl_3$) δ=8.34 (s, 1H), 7.54-7.46 (m, 3H), 7.44-7.41 (m, 4H), 7.37-7.36 (m, 1H), 7.34-7.20 (m, 1H), 4.90 (s, 2H), 4.37 (s, 2H), 3.74 (d, J=3.6 Hz, 1H), 1.35 (s, 2H), 1.20-1.16 (m, 2H). LCMS: (M+H)$^+$: 242.2, Rt: 2.519 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 µm particles). Detection methods are diode array (DAD) and evaporative light scattering (ELSD) detection as well as positive electrospray ionization (MS).

The following compounds were prepared in a similar fashion as described above for method C using different starting materials.

TABLE 2

Compounds Prepared by Method C

| Compound No. | IUPAC Name | MW | LC/MS Observed (M + H) | 1H NMR (400 MHz) |
|---|---|---|---|---|
| 9 | 3-([1,1'-biphenyl]-3-ylmethyl)-1-cyclopropyl-1H-pyrazolo[3,4-d]pyrimidin-4-amine | 341.41 | 342.2 | (CHLOROFORM-d) δ = 8.34 (s, 1H), 7.54-7.46 (m, 3H), 7.44-7.41 (m, 4H), 7.37-7.36 (m, 1H), 7.34-7.20 (m, 1H), 4.90 (s, 2H), 4.37 (s, 2H), 3.74 (d, J = 3.6 Hz, 1H), 1.35 (s, 2H), 1.20-1.16 (m, 2H) |
| 10 | 1-cyclopropyl-3-(3-(pyrimidin-5-yl)benzyl)-1H-pyrazolo[3,4-d]pyrimidin-4-amine | 343.39 | 344.1 | (DMSO-d6) δ = 9.18 (s, 1H), 9.08 (s, 2H), 8.15 (s, 1H), 7.80 (s, 1H), 7.64 (d, J = 7.6 Hz, 1H), 7.43 (t, J = 7.6 Hz, 1H), 7.27 (d, J = 7.2 Hz, 1H), 7.02 (s, 1H), 4.41 (s, 2H), 3.76-3.70 (m, 1H), 1.15-1.11 (m, 2H), 1.04-0.99 (m, 2H) |
| 11 | 1-cyclopropyl-3-(3-(pyridin-4-yl)benzyl)-1H-pyrazolo[3,4-d]pyrimidin-4-amine | 342.40 | 343.2 | (DMSO-d6) δ = 8.63 (s, 2H), 8.15 (s, 1H), 7.79 (s, 1H), 7.63 (s, 3H), 7.41 (s, 1H), 7.28 (s, 1H), 4.41 (s, 2H), 3.74 (s, 1H), 1.12 (d, J = 40.4 Hz, 4H) |
| 12 | 1-cyclopropyl-3-(3-(pyridin-3-yl)benzyl)-1H-pyrazolo[3,4-d]pyrimidin-4-amine | 342.40 | 343.2 | (METHANOL-d4) δ = 9.00 (s, 1H), 8.73 (d, J = 5.2 Hz, 1H), 8.59 (d, J = 7.2 Hz, 1H), 8.32 (s, 1H), 7.97-7.91 (m, 1H), 7.71-7.63 (m, 2H), 7.52 (t, J = 7.6 Hz, 1H), 7.39 (d, J = 7.6 Hz, 1H), 4.51 (s, 2H), 3.89 (m, 1H), 1.31-1.24 (m, 2H), 1.18-1.11 (m, 2H) |

TABLE 2-continued

Compounds Prepared by Method C

| Compound No. | IUPAC Name | MW | LC/MS Observed (M + H) | 1H NMR (400 MHz) |
|---|---|---|---|---|
| 13 | 1-cyclopropyl-3-(3-(pyridin-2-yl)benzyl)-1H-pyrazolo[3,4-d]pyrimidin-4-amine | 342.40 | 343.1 | (METHANOL-d4) δ = 8.73 (d, J = 5.2 Hz, 1H), 8.38-8.31 (m, 2H), 8.13 (d, J = 8.0 Hz, 1H), 7.87-7.80 (m, 2H), 7.78-7.73 (m, 1H), 7.60-7.54 (t, J = 7.6 Hz, 1H), 7.51-7.46 (m, 1H), 4.54 (s, 2H), 3.92 (m, 1H), 1.32-1.22 (m, 2H), 1.20-1.10 (m, 2H) |
| 14 | 1-cyclopropyl-3-(3-(pyrimidin-2-yl)benzyl)-1H-pyrazolo[3,4-d]pyrimidin-4-amine | 343.39 | 344.1 | (METHANOL-d4) δ = 8.82 (d, J = 5.2 Hz, 2H), 8.34-8.25 (m, 3H), 7.50-7.44 (m, 1H), 7.44-7.38 (m, 1H), 7.36 (t, J = 4.8 Hz, 1H), 4.50 (s, 2H), 3.91 (m, 1H), 1.35-1.27 (m, 2H), 1.21-1.11 (m, 2H) |
| 54 | 1-cyclopropyl-3-((4-phenylpyridin-2-yl)oxy)-1H-pyrazolo[3,4-d]pyrimidin-4-amine | 344.1 | 345.1 | (METHANOL-d4) δ = 8.32 (s, 1H), 8.25 (d, J = 5.2 Hz, 1H), 7.80-7.78 (m, 2H), 7.69 (s, 1H), 7.57-7.48 (m, 4H), 3.83-3.78 (m, 1H), 1.27-1.21 (m, 2H), 1.18-1.11 (m, 2H) |
| 55 | 3-([3,4'-bipyridin]-2'-yloxy)-1-cyclopropyl-1H-pyrazolo[3,4-d]pyrimidin-4-amine | 345.1 | 346.1 | (METHANOL-d4) δ = 9.05 (d, J = 2.0 Hz, 1H), 8.75-8.73 (m, 1H), 8.43-8.40 (m, 1H), 8.35-8.32 (m, 2H), 7.77-7.73 (m, 2H), 7.65-7.64 (m, 1H), 3.88-3.83 (m, 1H), 1.26-1.22 (m, 2H), 1.15-1.12 (m, 2H) |
| 56 | 1-cyclopropyl-3-((5-fluoro-[3,4'-bipyridin]-2'-yl)oxy)-1H-pyrazolo[3,4-d]pyrimidin-4-amine | 363.1 | 364.1 | (DMSO-d6) δ = 8.98 (s, 1H), 8.71 (d, J = 2.8 Hz, 1H), 8.29-8.26 (m, 1H), 8.23-8.21 (m, 114), 8.19 (s, 1H), 7.69 (s, 1H), 7.66-7.64 (m, 1H), 3.72-3.67 (m, 1H), 1.08-0.99 (m, 4H) |
| 57 | 1-cyclopropyl-3-((4-(3,6-dihydro-2H-pyran-4-yl)pyridin-2-yl)oxy)-1H-pyrazolo[3,4-d]pyrimidin-4-amine | 350.1 | 351.1 | (METHANOL-d4) δ = 8.33 (s, 1H), 8.13 (d, J = 5.6 Hz, 1H), 7.43 (s, 1H), 7.37-7.36 (m, 1H), 6.61-6.60 (m, 1H), 4.35-4.33 (m, 2H), 3.94 (t, J = 5.6 Hz, 2H), 3.84-3.81 (m, 1H), 2.58-2.52 (m, 2H), 1.25-1.09 (m, 4H) |
| 58 | 1-cyclopropyl-3-((2-phenylpyridin-4-yl)oxy)-1H-pyrazolo[3,4-d]pyrimidin-4-amine | 345.1 | 345.1 | (METHANOL-d4) δ = 8.76 (d, J = 6.4 Hz, 1H), 8.37 (s, 1H), 8.19 (d, J = 2.4 Hz, 1H), 7.97-7.93 (m, 2H), 7.84-7.82 (m, 1H), 7.64-7.61 (m, 3H), 3.91-3.86 (m, 1H), 1.28-1.26 (m, 2H), 1.17-1.15 (m, 2H) |
| 59 | 3-([2,3'-bipyridin]-4-yloxy)-1-cyclopropyl-1H-pyrazolo[3,4-d]pyrimidin-4-amine | 345.1 | 346.1 | (METHANOL-d4) δ = 9.41 (s, 1H), 8.95-8.93 (m, 1H), 8.83 (d, J = 5.2 Hz, 1H), 8.77 (d, J = 6.0 Hz, 1H), 8.37 (s, 1H), 8.15 (d, J = 2.0 Hz, 1H), 8.0-7.97 (m, 1H), 7.62-7.60 (m, 1H), 3.89-3.83 (m, 1H), 1.27-1.23 (m, 2H), 1.15-1.13 (m, 2H) |
| 60 | 1-cyclopropyl-3-((5'-fluoro-[2,3'-bipyridin]-4-yl)oxy)-1H-pyrazolo[3,4-d]pyrimidin-4-amine | 363.1 | 364.1 | (DMSO-d6) δ = 9.16 (s, 1H), 8.70-8.65 (m, 2H), 8.35-8.31 (m, 1H), 8.23 (s, 1H), 8.13 (d, J 1H), 3.73-3.68 (m, 1H), 1.15-1.02 (m, 4H) |
| 61 | 1-cyclopropyl-3-((2-(3,6-dihydro-2H-pyran-4-yl)pyridin-4-yl)oxy)-1H-pyrazolo[3,4-d]pyrimidin-4-amine | 350.1 | 351.1 | (METHANOL-d4) δ = 8.68 (d, J = 6.8 Hz, 1H), 8.38 (s, 1H), 8.00 (d, J = 2.0 Hz, 1H), 7.88-7.86 (m, 1H), 6.91-6.90 (m, 1H), 4.42-4.40 (m, 2H), 3.97 (t, J = 5.2 Hz, 2H), 3.92-3.89 (m, 1H), 2.66-2.61 (m, 2H), 1.28-1.15 (m, 4H) |

Synthesis Method D: General Procedure Represented by the Preparation of (4-amino-1-cyclopropyl-1H-pyrazolo[3,4-d]pyrimidin-3-yl)(phenyl)methanol and 3-benzyl-1-cyclopropyl-1H-pyrazolo[3,4-d]pyrimidin-4-amine

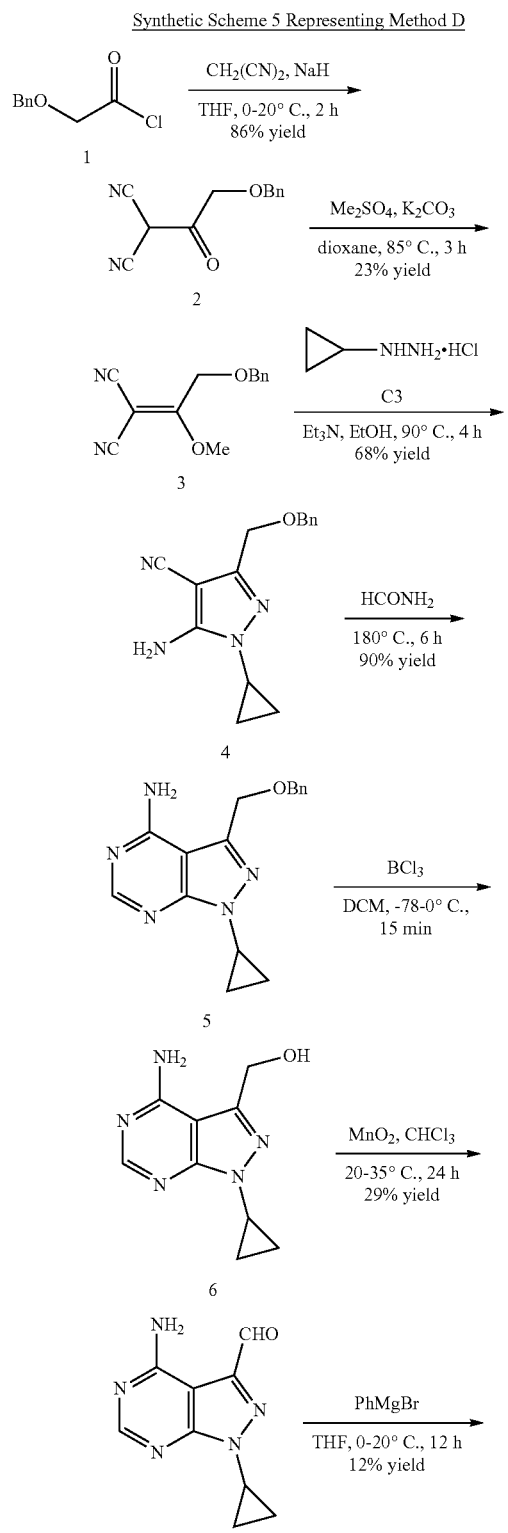

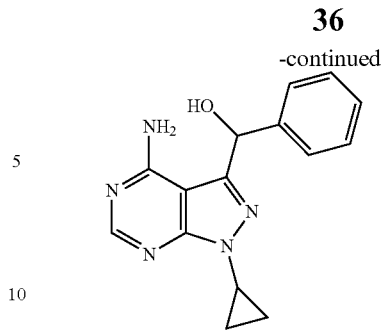

Step 1

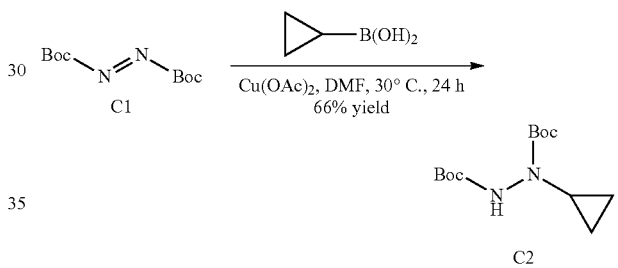

Di-tert-butyl (E)-diazene-1,2-dicarboxylate (200.0 g, 868.5 mmol, 1.0 eq), cyclopropylboronic acid (149.2 g, 1.7 mol, 2.0 eq) and Cu(OAc)$_2$ (15.7 g, 86.8 mmol, 0.1 eq) were combined in DMF (2.0 L), degassed and purged with N$_2$ three times, and then stirred at 30° C. for 24 h under N$_2$ atmosphere. The mixture was concentrated under reduced pressure and partitioned between EtOAc (2 L) and H$_2$O (2 L). The organic phase was separated, washed with brine (2 L), dried over Na$_2$SO$_4$, filtered and concentrated under reduced pressure to give a residue. The residue was taken up in 2 L of petroleum ether, stirred for 16 h and filtered to collect the solid to afford di-tert-butyl 1-cyclopropylhydrazine-1,2-dicarboxylate (470.0 g, 66.0% yield) as a white solid. $^1$H NMR (400 MHz, CDCl$_3$) δ=3.12-3.04 (m, 1H), 1.63 (s, 1H), 0.87-0.80 (m, 4H)

Step 2

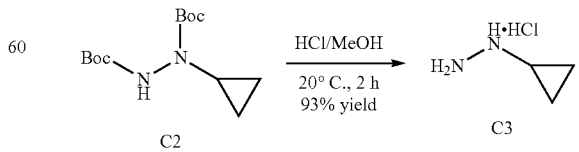

Di-tert-butyl 1-cyclopropylhydrazine-1,2-dicarboxylate (20.0 g, 73.4 mmol, 1.0 eq) was stirred in HCl/MeOH (200.0 mL) at 20° C. for 2 h. The mixture was concentrated under reduced pressure to give cyclopropylhydrazine (10.0 g, 68.9 mmol, 93.8% yield) without further purification.

Step 3

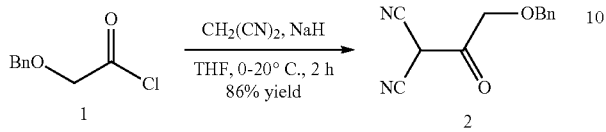

Malononitrile (12.5 g, 189.5 mmol, 1.0 eq) was dissolved in THF (600.0 mL) and the solution stirred at 0-5° C. while NaH (15.1 g, 379.1 mmol, 60% purity, 2.0 eq) was added in portions followed by drop-wise addition of 2-(benzyloxy) acetyl chloride (35.0 g, 189.5 mmol, 29.4 mL, 1.0 eq) in THF (70.0 mL). The solution was stirred at 20° C. for 2 h. The reaction mixture was poured into 1 M HCl (0.5 L), and extracted with 3×100 mL of EtOAc. The combined organic fractions were washed with brine (250 mL), dried over Na₂SO₄, filtered and concentrated under reduced pressure. The remaining residue was triturated with petroleum ether (250 mL) to give 2-(2-(benzyloxy)acetyl)malononitrile (37.5 g, 165 mmol, 86.7% yield) as a yellow solid.

Step 4

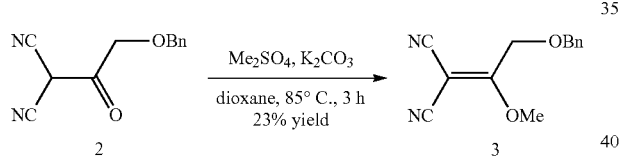

A mixture of 2-(2-(benzyloxy)acetyl)malononitrile (35.0 g, 163.3 mmol, 1.0 eq), Me₂SO₄ (28.8 g, 228.7 mmol, 21.6 mL, 1.4 eq) and K₂CO₃ (38.3 g, 277.7 mmol, 1.7 eq) in dioxane (500.0 mL) was degassed and purged with N₂ three times and then stirred at 85° C. for 3 h under N₂ atmosphere. The mixture was concentrated under reduced pressure and the residue purified by column chromatography (SiO₂, petroleum ether/ethyl acetate=1/1) to afford 2-(2-(benzyloxy)-1-methoxyethylidene)malononitrile (17.0 g, 38.7 mmol, 23.6% yield) as a yellow oil. ¹H NMR: (400 MHz, CDCl₃) δ=7.41-7.35 (m, 5H), 4.63 (s, 2H), 4.45 (s, 2H), 4.20 (s, 3H).

Step 5

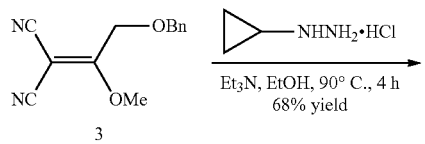

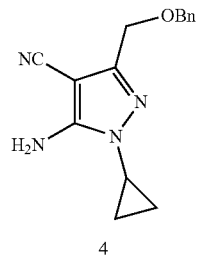

A mixture of 2-(2-(benzyloxy)-1-methoxyethylidene)malononitrile (20.0 g, 87.6 mmol, 1.0 eq), cyclopropylhydrazine (10.4 g, 96.3 mmol, 1.1 eq, HCl), Et₃N (11.5 g, 113.9 mmol, 15.7 mL, 1.3 eq) in EtOH (400.0 mL) was degassed and purged with N₂ three times and then stirred at 90° C. for 4 h under N₂ atmosphere. The mixture was concentrated under reduced pressure and the remaining residue was purified by column chromatography (SiO₂, petroleum ether/ethyl acetate=1/2) to afford 5-amino-3-((benzyloxy)methyl)-1-cyclopropyl-1H-pyrazole-4-carbonitrile (16.0 g, 59.6 mmol, 68.0% yield) as a yellow solid. ¹H NMR: (400 MHz, CDCl₃) δ=7.44-7.39 (m, 2H), 7.35 (t, J=7.2 Hz, 2H), 7.32-7.27 (m, 1H), 4.67 (s, 2H), 4.61 (s, 2H), 4.47 (s, 2H), 3.12-3.04 (m, 1H), 1.16-1.05 (m, 4H).

Step 6

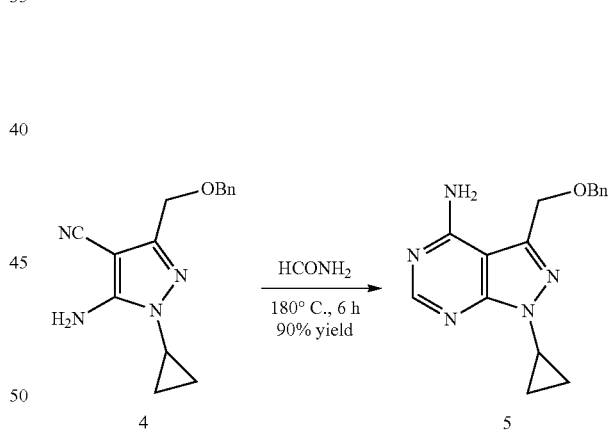

A mixture of 5-amino-3-((benzyloxy)methyl)-1-cyclopropyl-1H-pyrazole-4-carbonitrile (15.0 g, 55.9 mmol, 1.0 eq) and formamide (254.2 g, 5.6 mol, 225.0 mL, 100.9 eq) was degassed and purged with N₂ three times, and then stirred at 180° C. for 6 h under N₂ atmosphere. The solution stood for 12 h at 20° C. and the deposited crystalline material was separated by filtration and washed with formamide (30 mL), water (100 mL) and dried under reduced pressure to give 3-((benzyloxy)methyl)-1-cyclopropyl-1H-pyrazolo[3,4-d]pyrimidin-4-amine (15.0 g, 50.6 mmol, 90.5% yield) as a yellow solid. ¹H NMR: (400 MHz, CDCl₃) δ=8.33 (s, 1H), 8.22 (d, J=13.6 Hz, 1H), 7.39-7.28 (m, 5H), 4.86 (s, 2H), 4.59 (s, 2H), 3.72-3.66 (m, 1H), 1.30-1.23 (m, 2H), 1.18-1.09 (m, 2H).

Step 7

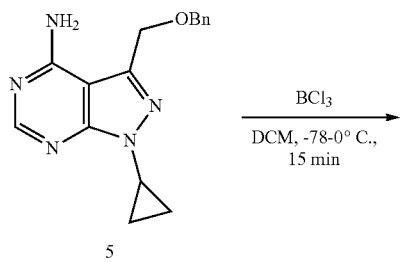

A mixture of (4-amino-1-cyclopropyl-1H-pyrazolo[3,4-d]pyrimidin-3-yl)methanol (5.0 g, 24.3 mmol, 1.0 eq) and MnO$_2$ (21.1 g, 243.6 mmol, 10.0 eq) in CHCl$_3$ (20.0 mL) was degassed and purged with N$_2$ three times, and then stirred at 20-35° C. for 24 h under N$_2$ atmosphere. The mixture was filtered and the filtrate was concentrated under reduced pressure to give 4-amino-1-cyclopropyl-1H-pyrazolo[3,4-d]pyrimidine-3-carbaldehyde (2.0 g, 7.0 mmol, 29.0% yield) as a yellow solid without further purification. $^1$H NMR: (400 MHz, METHANOL-d$_4$) δ=9.91 (s, 1H), 8.29 (s, 1H), 4.04-3.98 (m, 1H), 1.36-1.34 (m, 2H), 1.21-1.19 (m, 2H).

Step 9

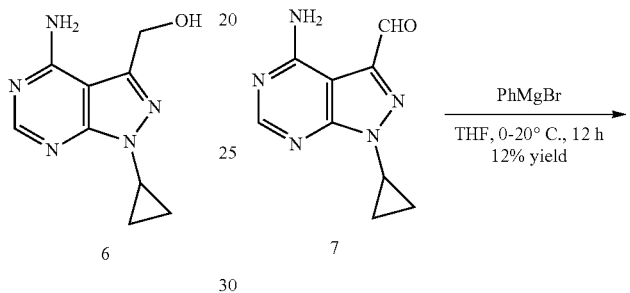

To a solution of 3-((benzyloxy)methyl)-1-cyclopropyl-1H-pyrazolo[3,4-d]pyrimidin-4-amine (13.0 g, 44.0 mmol, 1.0 eq) in DCM (390.0 mL) was added BCl$_3$ (1 M, 176.0 mL, 4.0 eq) dropwise at −78° C., then the reaction was warmed to 0° C., and stirred at 0° C. for 15 min. TLC (DCM/MeOH=10/1) indicated no starting material remained and one major new spot with larger polarity was detected. The reaction was quenched with MeOH (100 mL) at −78° C. and then the pH was adjusted to 7 by addition of NH$_3$.H$_2$O at 0° C. The mixture was filtered and the filtrate was concentrated under reduced pressure. The remaining residue was precipitated by addition of petroleum ether (100 mL), filtered and the filter cake was concentrated under reduced pressure to give (4-amino-1-cyclopropyl-1H-pyrazolo[3,4-d]pyrimidin-3-yl)methanol (15.0 g, crude) as a brown solid. $^1$H NMR: (400 MHz, METHANOL-d$_4$) δ=8.18 (s, 1H), 8.05 (s, 1H), 4.82 (s, 2H), 3.70-3.59 (m, 1H), 1.19-1.07 (m, 4H).

Step 8

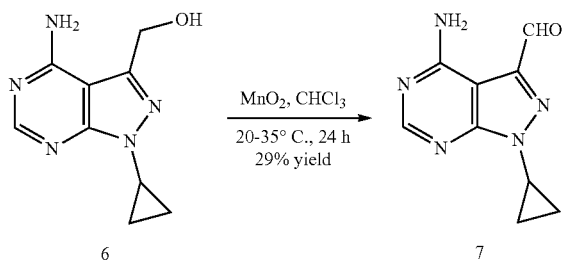

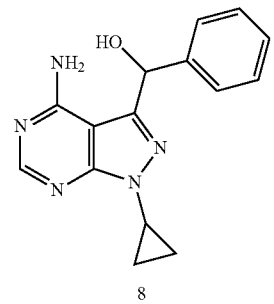

To a solution of 4-amino-1-cyclopropyl-1H-pyrazolo[3,4-d]pyrimidine-3-carbaldehyde (200.0 mg, 984.2 μmol, 1.0 eq) in THF (10.0 mL) was added bromo(phenyl)magnesium (3 M, 656.1 μL, 2.0 eq) at 0° C. The mixture was warmed to 20° C. and stirred at 20° C. for 12 h, then quenched with saturated NH$_4$Cl aq. (10 mL) and extracted with DCM (2×5 mL). The combined organic layers were dried over Na$_2$SO$_4$, filtered and concentrated under reduced pressure. The remaining residue was purified by prep-HPLC (condition: neutral) to give (4-amino-1-cyclopropyl-1H-pyrazolo[3,4-d]pyrimidin-3-yl)(phenyl)methanol (39.0 mg, 125.1 μmol, 12.7% yield, 90.2% purity) as a white solid. $^1$H NMR: (400 MHz, METHANOL-d$_4$) δ=8.18 (s, 1H), 7.41-7.36 (m, 2H), 7.31 (t, J=7.6 Hz, 2H), 7.26-7.20 (m, 1H), 6.02 (s, 1H), 3.71-3.65 (m, 1H), 1.20-1.18 (m, 2H), 1.13-1.10 (m, 2H). LCMS: (M+H)⁺: 282.1, Rt: 2.267 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Step 10

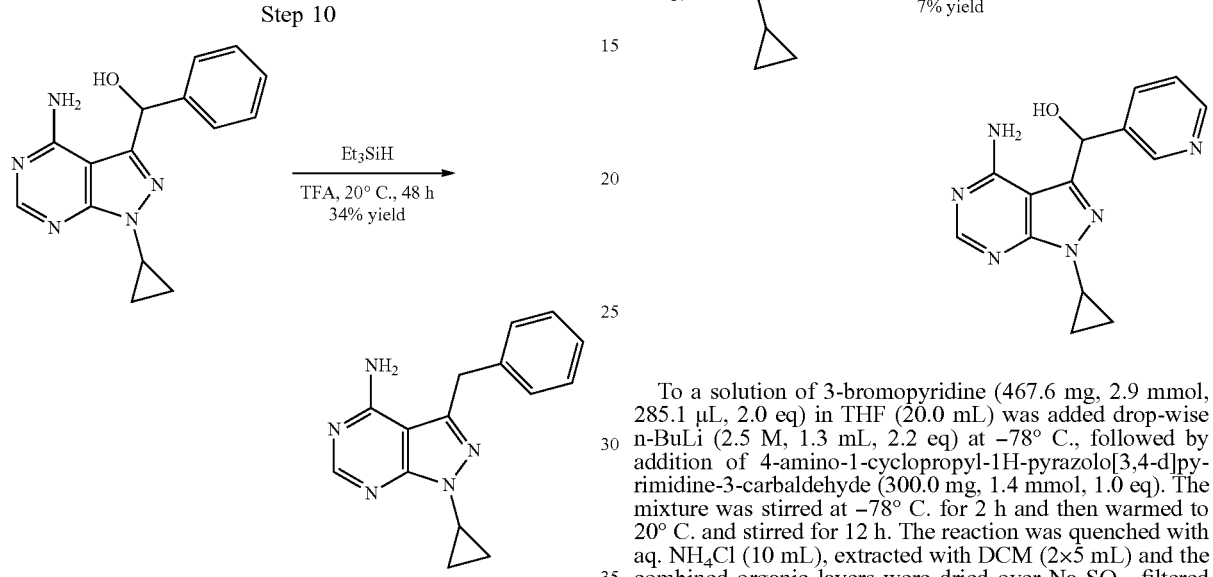

To a solution of (4-amino-1-cyclopropyl-1H-pyrazolo[3,4-d]pyrimidin-3-yl)(phenyl)methanol (19.0 mg, 67.5 μmol, 1.0 eq) in TFA (500.0 μL) was added Et₃SiH (27.4 mg, 236.3 μmol, 37.6 μL, 3.5 eq). The mixture was stirred at 20° C. for 48 h, concentrated under reduced pressure and purified by prep-HPLC (condition: TFA) to give 3-benzyl-1-cyclopropyl-1H-pyrazolo[3,4-d]pyrimidin-4-amine (Compound 15) (6.2 mg, 23.0 mol, 34.1% yield, 98.7% purity) as a white solid. ¹H NMR: (400 MHz, METHANOL-d₄) δ=8.29 (s, 1H), 7.34-7.27 (m, 2H), 7.27-7.16 (m, 3H), 4.38 (s, 2H), 3.91-3.85 (m, 1H), 1.32-1.26 (m, 2H), 1.19-1.13 (m, 2H). LCMS: (M+H)⁺: 266.1, Rt: 1.983 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive elctrospray ionization (MS).

Alternative Step 9. Represented by the Preparation of (4-amino-1-cyclopropyl-1H-pyrazolo[3,4-d]pyrimidin-3-yl)(pyridin-3-yl)methanol

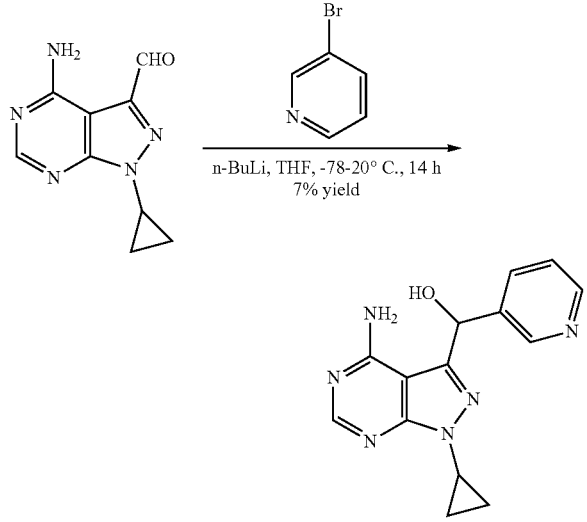

To a solution of 3-bromopyridine (467.6 mg, 2.9 mmol, 285.1 μL, 2.0 eq) in THF (20.0 mL) was added drop-wise n-BuLi (2.5 M, 1.3 mL, 2.2 eq) at −78° C., followed by addition of 4-amino-1-cyclopropyl-1H-pyrazolo[3,4-d]pyrimidine-3-carbaldehyde (300.0 mg, 1.4 mmol, 1.0 eq). The mixture was stirred at −78° C. for 2 h and then warmed to 20° C. and stirred for 12 h. The reaction was quenched with aq. NH₄Cl (10 mL), extracted with DCM (2×5 mL) and the combined organic layers were dried over Na₂SO₄, filtered and concentrated under reduced pressure. The residue was purified by prep-HPLC (condition: TFA) to give (4-amino-1-cyclopropyl-1H-pyrazolo[3,4-d]pyrimidin-3-yl)(pyridin-3-yl)methanol (Compound 18) (30.0 mg, 105.4 μmol, 7.1% yield, 99.2% purity) as a yellow solid. ¹H NMR: (400 MHz, METHANOL-d₄) δ=8.87 (d, J=1.6 Hz, 1H), 8.70 (d, J=5.6 Hz, 1H), 8.39 (d, J=8.0 Hz, 1H), 8.36 (s, 1H), 7.86 (dd, J=5.6, 8.0 Hz, 1H), 6.34 (s, 1H), 3.95-3.89 (m, 1H), 1.28-1.22 (m, 2H), 1.18-1.11 (m, 2H). LCMS: (M+H)⁺: 283.1, Rt: 2.037 min. LC/MS (The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

The following compounds were prepared in a similar manner as for method D using different starting materials.

TABLE 3

Compounds Prepared by Method D

| Compound No. | IUPAC Name | MW | LC/MS Observed (M + H) | 1H NMR (400 MHz) |
|---|---|---|---|---|
| 16 | (4-amino-1-cyclopropyl-1H-pyrazolo[3,4-d]pyrimidin-3-yl)(phenyl)methanol | 281.31 | 282.1 | (METHANOL-d4) δ = 8.18 (s, 1H), 7.41-7.36 (m, 2H), 7.31 (t, J = 7.6 Hz, 2H), 7.26-7.20 (m, 1H), 6.02 (s, 1H), 3.71-3.65 (m, 1H), 1.20-1.18 (m, 2H), 1.13-1.10 (m, 2H) |

TABLE 3-continued

Compounds Prepared by Method D

| Compound No. | IUPAC Name | MW | LC/MS Observed (M + H) | 1H NMR (400 MHz) |
|---|---|---|---|---|
| 17 | 3-benzyl-1-cyclopropyl-1H-pyrazolo[3,4-d]pyrimidin-4-amine | 265.31 | 266.1 | (METHANOL-d4) δ = 8.29 (s, 1H), 7.34-7.27 (m, 2H), 7.27-7.16 (m, 3H), 4.38 (s, 2H), 3.91-3.85 (m, 1H), 1.32-1.26 (m, 2H), 1.19-1.13 (m, 2H) |
| 18 | (4-amino-1-cyclopropyl-1H-pyrazolo[3,4-d]pyrimidin-3-yl)(pyridin-3-yl)methanol | 282.30 | 283.1 | (METHANOL-d4) δ = 8.87 (d, J = 1.6 Hz, 1H), 8.70 (d, J = 5.6 Hz, 1H), 8.39 (d, J = 8.0 Hz, 1H), 8.36 (s, 1H), 7.86 (dd, J = 5.6, 8.0 Hz, 1H), 6.34 (s, 1H), 3.95-3.89 (m, 1H), 1.28-1.22 (m, 2H), 1.18-1.11 (m, 2H) |

Synthesis Method E: General Procedure Represented by the Preparation of 3-(3-chlorophenethyl)-1-cyclopropyl-1H-pyrazolo[3,4-d]pyrimidin-4-amine and 1-cyclopropyl-3-(3-fluorophenethyl)-1H-pyrazolo[3,4-d]pyrimidin-4-amine

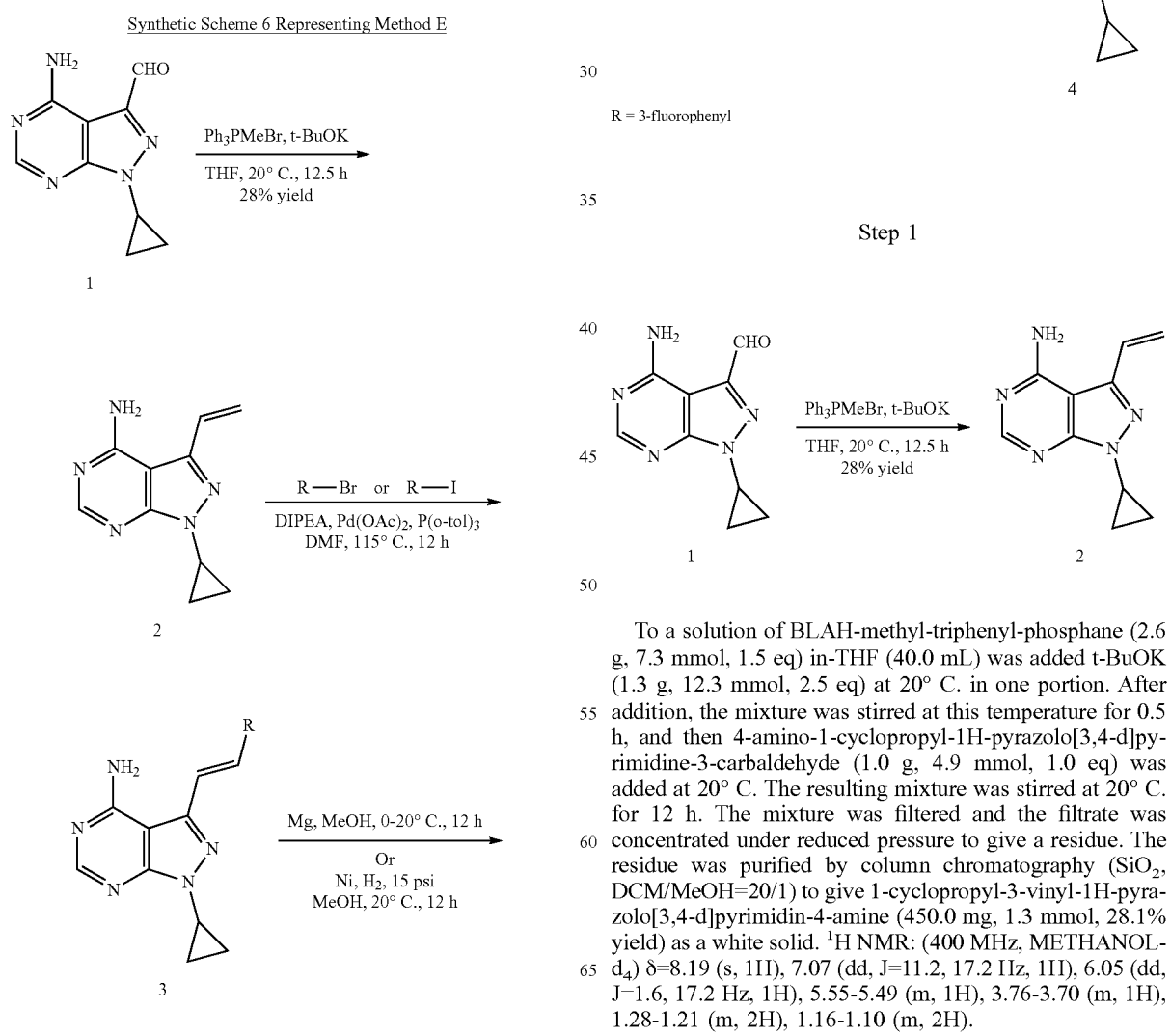

R = 3-fluorophenyl

Step 1

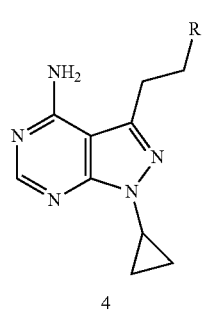

To a solution of BLAH-methyl-triphenyl-phosphane (2.6 g, 7.3 mmol, 1.5 eq) in-THF (40.0 mL) was added t-BuOK (1.3 g, 12.3 mmol, 2.5 eq) at 20° C. in one portion. After addition, the mixture was stirred at this temperature for 0.5 h, and then 4-amino-1-cyclopropyl-1H-pyrazolo[3,4-d]pyrimidine-3-carbaldehyde (1.0 g, 4.9 mmol, 1.0 eq) was added at 20° C. The resulting mixture was stirred at 20° C. for 12 h. The mixture was filtered and the filtrate was concentrated under reduced pressure to give a residue. The residue was purified by column chromatography (SiO$_2$, DCM/MeOH=20/1) to give 1-cyclopropyl-3-vinyl-1H-pyrazolo[3,4-d]pyrimidin-4-amine (450.0 mg, 1.3 mmol, 28.1% yield) as a white solid. $^1$H NMR: (400 MHz, METHANOL-d$_4$) δ=8.19 (s, 1H), 7.07 (dd, J=11.2, 17.2 Hz, 1H), 6.05 (dd, J=1.6, 17.2 Hz, 1H), 5.55-5.49 (m, 1H), 3.76-3.70 (m, 1H), 1.28-1.21 (m, 2H), 1.16-1.10 (m, 2H).

Step 2

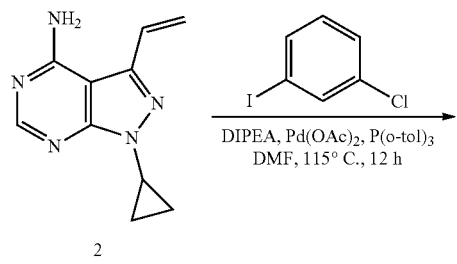

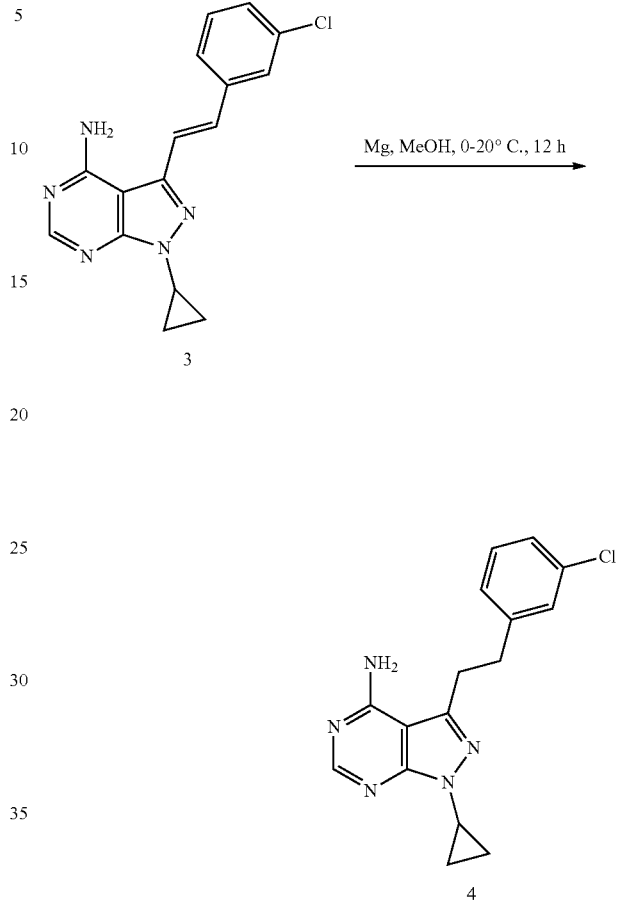

Step 3

1-Cyclopropyl-3-vinyl-1H-pyrazolo[3,4-d]pyrimidin-4-amine (125.0 mg, 621.1 µmol, 1.0 eq), 3-chloroiodobenzene (148.1 mg, 621.1 µmol, 76.7 µL, 1.0 eq), Pd(OAc)$_2$ (1.3 mg, 6.2 µmol, 0.01 eq), tri-ortho-tolylphosphine (56.7 mg, 186.3 µmol, 0.3 eq) and DIPEA (120.4 mg, 931.7 µmol, 162.7 µL, 1.5 eq) were combined in DMF (1.5 mL) and degassed and purged with N$_2$ three times, then stirred at 115° C. for 12 h under N$_2$ atmosphere. The mixture was filtered over celite and the filtrate was concentrated under reduced pressure. The residue was purified by prep-HPLC (condition: TFA) to give (E)-3-(3-chlorostyryl)-1-cyclopropyl-1H-pyrazolo[3,4-d]pyrimidin-4-amine (50.0 mg, 110.3 µmol, 17.7% yield, 94% purity, TFA) as a brown solid. $^1$H NMR: (400 MHz, METHANOL-d$_4$) δ=8.31 (s, 1H), 7.81 (s, 1H), 7.60-7.56 (m, 3H), 7.36 (td, J=8.0, 16.0 Hz, 2H), 3.98 (m, 1H), 1.40-1.33 (m, 2H), 1.23-1.15 (m, 2H). LCMS: (M+H)$^+$: 312.1, Rt: 2.445 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 µm particles). Detection methods are diode array (DAD) and evaporative light scattering (ELSD) detection as well as positive electrospray ionization (MS).

To a solution of (E)-3-(3-chlorostyryl)-1-cyclopropyl-1H-pyrazolo[3,4-d]pyrimidin-4-amine (15.0 mg, 53.9 µmol, 1.0 eq) in MeOH (10.0 mL) was added Mg (26.2 mg, 1.0 mmol, 20.0 eq) at 0° C. The mixture was warmed to 20° C. and stirred at 20° C. for 12 h. The mixture was quenched with sat. NH$_4$Cl aq. (10 mL), extracted with DCM (2×5 mL). The combined organic extracts were dried over Na$_2$SO$_4$, filtered and concentrated under reduced pressure. The residue was purified by prep-HPLC (condition: neutral) to give 3-(3-chlorophenethyl)-1-cyclopropyl-1H-pyrazolo[3,4-d]pyrimidin-4-amine (Compound 19) (3.1 mg, 10.8 µmol, 20.1% yield, 98% purity) as a white solid. $^1$H NMR: (400 MHz, METHANOL-d$_4$) δ=8.27 (s, 1H), 7.19 (s, 3H), 7.11 (s, 1H), 3.84 (s, 1H), 3.39-3.35 (m, 2H), 3.09 (d, J=8.0 Hz, 2H), 1.20 (s, 2H), 1.13 (s, 2H). LCMS: (M+H)$^+$: 314.0, RT: 2.382 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 m particles). Detection methods are diode array (DAD) and evaporative light scattering (ELSD) detection as well as positive electrospray ionization (MS).

Step 3A

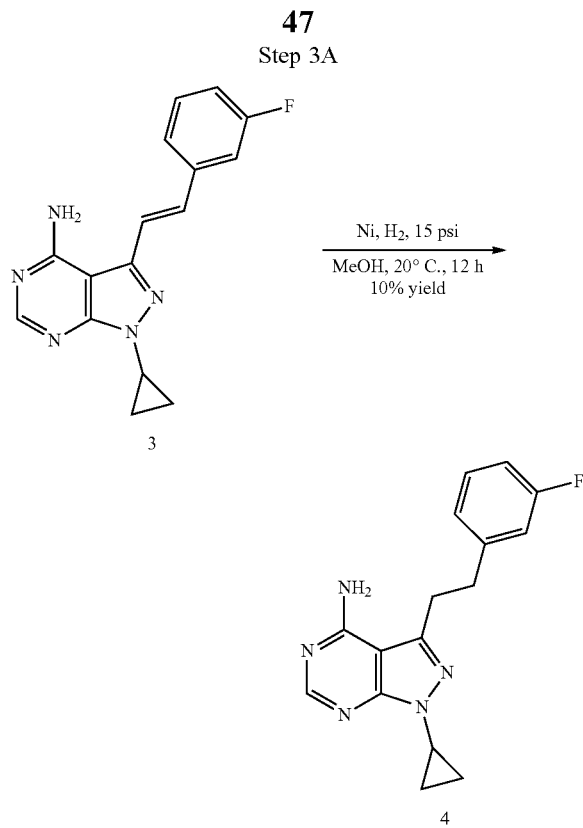

To a solution of (E)-1-cyclopropyl-3-(3-fluorostyryl)-1H-pyrazolo[3,4-d]pyrimidin-4-amine (30.0 mg, 101.5 µmol, 1.0 eq) in MeOH (5.0 mL) was added Raney-Ni (0.6 g). The suspension was degassed and purged with $H_2$ three times and then stirred under $H_2$ (15 Psi) at 20° C. for 12 h, filtered over celite and concentrated under reduced pressure. The residue was purified by prep-HPLC (condition: TFA) to give 1-cyclopropyl-3-(3-fluorophenethyl)-1H-pyrazolo[3,4-d]pyrimidin-4-amine (Compound 20) (3.1 mg, 10.3 µmol, 10.1% yield, 99.3% purity) as a white solid. $^1$H NMR: (400 MHz, METHANOL-d$_4$) δ=8.27 (s, 1H), 7.24 (d, J=7.6 Hz, 1H), 7.00-6.86 (m, 3H), 3.83 (s, 1H), 3.15-3.06 (m, 2H), 1.19 (s, 2H), 1.12 (d, J=6.4 Hz, 2H). LCMS: (M+H)$^+$: 298.1, RT: 2.203 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 µm particles). Detection methods are diode array (DAD) and evaporative light scattering (ELSD) detection as well as positive electrospray ionization (MS).

The following compounds were prepared in a similar manner as described in method E using different starting materials.

TABLE 4

Compounds Prepared by Method E

| Compound No. | IUPAC Name | MW | LC/MS Observed (M + H) | 1H NMR (400 MHz) |
|---|---|---|---|---|
| 21 | (E)-1-cyclopropyl-3-(2-(pyridin-3-yl)vinyl)-1H-pyrazolo[3,4-d]pyrimidin-4-amine | 278.31 | 279.1 | (METHANOL-d4) δ = 8.99 (s, 1H), 8.69-8.56 (m, 2H), 8.34 (s, 1H), 7.87-7.77 (m, 2H), 7.75-7.66 (m, 1H), 4.03 (m, 1H), 1.40-1.34 (m, 2H), 1.24-1.17 (m, 2H) |
| 22 | 1-cyclopropyl-3-(3-fluorophenethyl)-1H-pyrazolo[3,4-d]pyrimidin-4-amine | 297.33 | 298.1 | (METHANOL-d4) δ = 8.27 (s, 1H), 7.24 (d, J = 7.6 Hz, 1H), 7.00-6.86 (m, 3H), 3.83 (s, 1H), 3.15-3.06 (m, 2H), 1.19 (s, 2H), 1.12 (d, J = 6.4 Hz, 2H) |
| 23 | (E)-3-(3-chlorostyryl)-1-cyclopropyl-1H-pyrazolo[3,4-d]pyrimidin-4-amine | 311.77 | 312.1 | (METHANOL-d4) δ = 8.31 (s, 1H), 7.81 (s, 1H), 7.60-7.56 (m, 3H), 7.36 (td, J = 8.0, 16.0 Hz, 2H), 3.98 (m, 1H), 1.40-1.33 (m, 2H), 1.23-1.15 (m, 2H) |
| 24 | (E)-3-(4-chlorostyryl)-1-cyclopropyl-1H-pyrazolo[3,4-d]pyrimidin-4-amine | 311.77 | 312.1 | (METHANOL-d4) δ = 8.31 (s, 1H), 7.68 (d, J = 8.4 Hz, 2H), 7.62-7.48 (m, 2H), 7.40 (d, J = 8.4 Hz, 2H), 4.00-3.91 (m, 1H), 1.39-1.33 (m, 2H), 1.22-1.15 (m, 2H) |
| 25 | (E)-1-cyclopropyl-3-(3-fluorostyryl)-1H-pyrazolo[3,4-d]pyrimidin-4-amine | 295.31 | 296.1 | (METHANOL-d4) δ = 8.32 (s, 1H), 7.64-7.51 (m, 3H), 7.49-7.36 (m, 2H), 7.11-7.03 (m, 1H), 3.99 (m, 1H), 1.41-1.33 (m, 2H), 1.24-1.16 (m, 2H) |
| 26 | 3-(3-chlorophenethyl)-1-cyclopropyl-1H-pyrazolo[3,4-d]pyrimidin-4-amine | 313.78 | 314.0 | (METHANOL-d4) δ = 8.27 (s, 1H), 7.19 (s, 3H), 7.11 (s, 1H), 3.84 (s, 1H), 3.39-3.35 (m, 2H), 3.09 (d, J = 8.0 Hz, 2H), 1.20 (s, 2H), 1.13 (s, 2H) |

TABLE 4-continued

Compounds Prepared by Method E

| Compound No. | IUPAC Name | MW | LC/MS Observed (M + H) | 1H NMR (400 MHz) |
|---|---|---|---|---|
| 27 | 3-(4-chlorophenethyl)-1-cyclopropyl-1H-pyrazolo[3,4-d]pyrimidin-4-amine | 313.78 | 314.1 | (METHANOL-d4) δ = 8.27 (s, 1H), 7.25-7.21 (m, 2H), 7.17-7.12 (m, 2H), 3.88-3.79 (m, 1H), 3.28 (s, 2H), 3.11-3.04 (m, 2H), 1.18 (d, J = 2.4 Hz, 2H), 1.15-1.09 (m, 2H) |
| 28 | 1-cyclopropyl-3-(2-(pyridin-3-yl)ethyl)-1H-pyrazolo[3,4-d]pyrimidin-4-amine | 280.33 | 281.1 | (METHANOL-d4) δ = 8.32 (d, J = 13.6 Hz, 2H), 8.16 (s, 1H), 7.66 (d, J = 8.0 Hz, 1H), 7.32 (s, 1H), 3.63 (s, 1H), 3.29-3.27 (m, 2H), 3.12 (d, J = 7.2 Hz, 2H), 1.09 (s, 4H) |
| 62 | (E)-1-cyclopropyl-3-(2-(6-methylpyridin-3-yl)vinyl)-1H-pyrazolo[3,4-d]pyrimidin-4-amine | 292.1 | 293.1 | (DMSO-d6) δ = 9.01 (s, 1H), 8.72 (d, J = 7.2 Hz, 1H), 8.37 (s, 1H), 7.88-7.84 (m, 1H), 7.82-7.79 (m, 1H), 7.61-7.56 (m, 1H), 3.96-3.90 (m, 1H), 2.67 (s, 3H), 1.26-1.22 (m, 2H), 1.16-1.13 (m, 2H) |
| 63 | 1-cyclopropyl-3-(2-(6-methylpyridin-3-yl)ethyl)-1H-pyrazolo[3,4-d]pyrimidin-4-amine | 293.9 | 295.1 | (DMSO-d6) δ = 8.65 (s, 1H), 8.30-8.26 (m, 2H), 7.77 (d, J = 8.4 Hz, 1H), 3.79-3.74 (m, 1H), 3.35-3.31 (m, 2H), 3.14-3.10 (m, 2H), 2.65 (s, 3H), 1.05-1.04 (m, 4H) |

Synthesis Method F: General Procedure Represented by the Preparation of 3-((6-chloropyridin-2-yl)oxy)-1-cyclopropyl-1H-pyrazolo[3,4-d]pyrimidin-4-amine

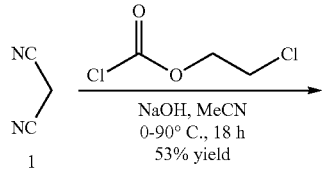

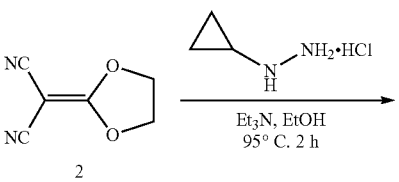

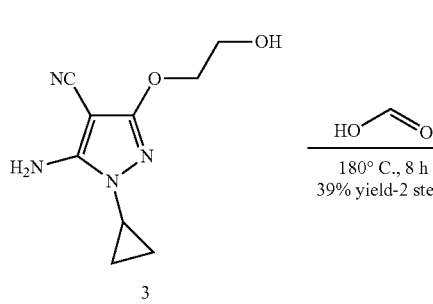

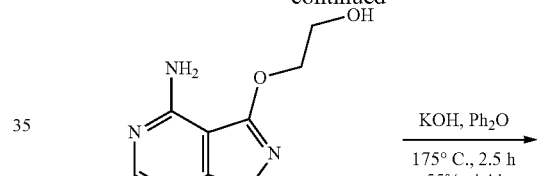

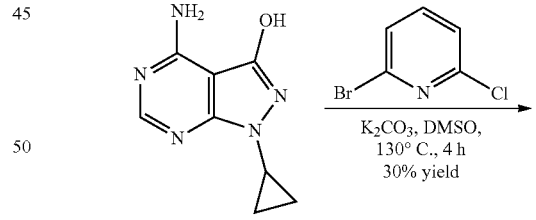

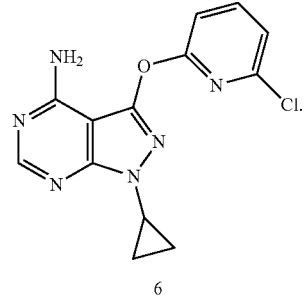

Step 1

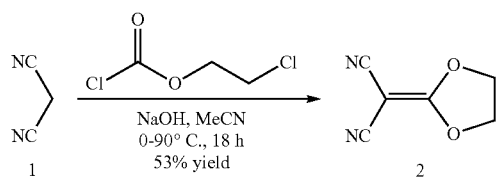

Malononitrile (20.0 g, 302.8 mmol, 1.0 eq) and NaOH (24.2 g, 605.5 mmol, 2.0 eq) were combined in MeCN (500.0 mL), degassed and purged with nitrogen three times, and stirred at 25° C. for about 2 h under nitrogen atmosphere. The reaction mixture was filtered and the solid collected, resuspended in MeCN (500.0 mL) and 2-chloroethyl carbonochloridate (43.3 g, 302.8 mmol, 1.0 eq), diluted in 100 mL MeCN, was added dropwise at 0° C. The reaction was stirred at 90° C. for about 16 h, concentrated under reduced pressure and purified by column chromatography (SiO$_2$, DCM/MeOH=10/1 to 4/1) to give 22.0 g (53.4% yield) of 2-(1,3-dioxolan-2-ylidene)malononitrile as a light yellow solid.

Step 2

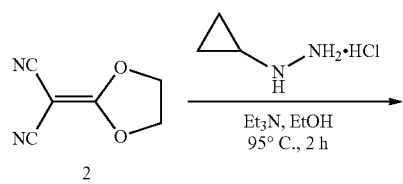

2-(1,3-Dioxolan-2-ylidene)malononitrile (16.0 g, 117.5 mmol, 1.0 eq), cyclopropylhydrazine (20.5 g, 141.1 mmol, 1.2 eq, HCl) and triethylamine (47.6 g, 470.2 mmol, 4.0 eq) were combined in ethanol (200.0 mL) and stirred at 95° C. for about 2 h under nitrogen atmosphere. The reaction mixture was concentrated by rotary evaporator to give 5-amino-1-cyclopropyl-3-(2-hydroxyethoxy)-1H-pyrazole-4-carbonitrile (40 g, crude) as a yellow solid which was used for next step directly.

Step 3

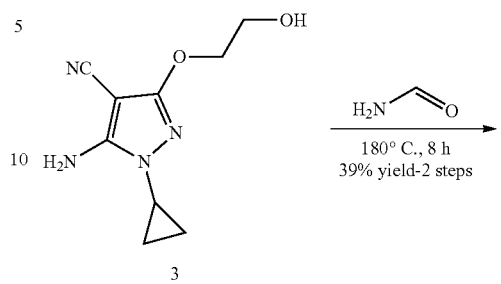

5-Amino-1-cyclopropyl-3-(2-hydroxyethoxy)-1H-pyrazole-4-carbonitrile (30.0 g, crude) was stirred in formamide (150.0 mL) at 180° C. for about 8 h. The reaction mixture was purified by prep-HPLC (condition: neutral) to give 2-((4-amino-1-cyclopropyl-1H-pyrazolo[3,4-d]pyrimidin-3-yl)oxy)ethan-1-ol (9 g, 38.3 mmol) as a yellow solid. $^1$H NMR: (400 MHz, DMSO-d$_6$) δ=8.11 (s, 1H), 7.68 (s, 1H), 6.72 (s, 1H), 5.03 (t, J=6.4 Hz, 1H), 4.20 (t, J=4.4 Hz, 2H), 3.74-3.71 (m, 2H), 3.55-3.51 (m, 1H), 1.07-1.04 (m, 2H), 0.98-0.95 (m, 2H).

Step 4

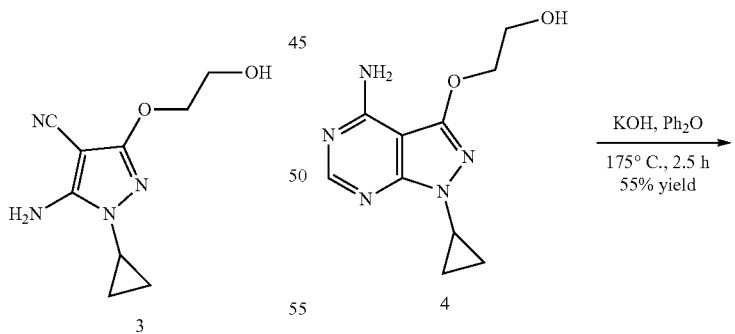

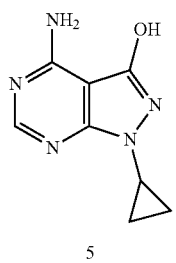

2-((4-Amino-1-cyclopropyl-1H-pyrazolo[3,4-d]pyrimidin-3-yl)oxy)ethan-1-ol (6.0 g, 25.5 mmol, 1.0 eq) and KOH (17.2 g, 306.1 mmol, 12.0 eq) were stirred in diphenyl ether (15.0 mL) at 175° C. for about 2.5 h. The reaction mixture was washed with 30 mL of petroleum ether, filtered and the solid was dissolved in about 15 mL of water. The pH was adjusted to between 6 and 7 with HCl and the newly formed precipitate was collected by filtration and dried under reduced pressure to give 4-amino-1-cyclopropyl-H-pyrazolo[3,4-d]pyrimidin-3-ol (3.0 g, 55.4% yield, 90% purity) as a white solid used without further purification. $^1$H NMR: (400 MHz, DMSO-d$_6$) δ=11.18 (s, 1H), 8.08 (s, 1H), 7.51-7.37 (m, 1H), 6.61 (s, 1H), 3.47-3.42 (m, 1H), 1.04-1.00 (m, 2H), 0.94-0.91 (m, 2H).

Step 5

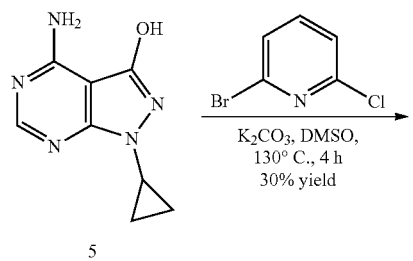

5

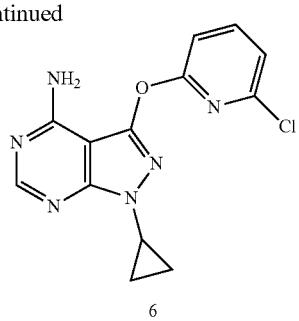

6

4-Amino-1-cyclopropyl-1H-pyrazolo[3,4-d]pyrimidin-3-ol (0.2 g, 1.1 mmol, 1 eq), 2-bromo-6-chloro-pyridine (402.6 mg, 2.1 mmol, 2 eq) and K$_2$CO$_3$ (173.5 mg, 1.3 mmol, 1.2 eq) were combined in DMSO (4 mL) was stirred at 130° C. for about 4 h. The mixture was filtered and the filtrate was purified by prep-HPLC (condition: TFA) to give 3-((6-chloropyridin-2-yl)oxy)-1-cyclopropyl-1H-pyrazolo[3,4-d]pyrimidin-4-amine (Compound 29)(97.7 mg, 30.1% yield, 97.5% purity) as a light yellow solid. $^1$H NMR: (400 MHz, DMSO-d$_6$) δ=8.59-8.45 (m, 1H), 8.34 (s, 1H), 7.98 (t, J=(8.0 Hz, 1H), 7.37 (d, =7.6 Hz, 1H), 7.24 (d, J=8.0 Hz, 1H), 3.80-3.75 (m, 1H), 1.08-1.04 (m, 4H). LCMS: (M+H)$^+$: 303.1, Rt: 2.356 min. LC/MS (The gradient was 10-100% B in 3.4 m with hold at 100% B for 0.45 min, 100-10% Bin 0.01 min, and then held at 10% B for 0.65 min (0.8 mL/min flowrate). Mobile phase A was 0.0375% CF$_3$CO$_2$H in water, mobile phase was 0.018% CF$_3$CO$_2$H in CH$_3$CN. The column used for the chromatography was a 2.0×50 mm phenomenex Luna-C18 column (5 m particles). Detection methods are diode array (DAD) and evaporative light scattering (ELSD) detection as well as positive electrospray ionization (MS).

The following compounds were prepared in a similar manner as described in method F using different starting materials.

TABLE 5

Compounds Prepared by Method E

| Compound No. | IUPAC Name | MW | LC/MS Observed (M + H) | 1H NMR (400 MHz) |
|---|---|---|---|---|
| 30 | 3-((6-chloropyridin-2-yl)oxy)-1-cyclopropyl-1H-pyrazolo[3,4-d]pyrimidin-4-amine | 302.71904 | 303.1 | (DMSO-d6) δ = 8.59-8.45 (m, 1H), 8.34 (s, 1H), 7.98 (t, J = 8.0 Hz, 1H), 7.37 (d, J = 7.6 Hz, 1H), 7.24 (d, J = 8.0 Hz, 1H), 3.80-3.75 (m, 1H), 1.08-1.04 (m, 4H) |
| 31 | 3-((6-bromopyridin-2-yl)oxy)-1-cyclopropyl-1H-pyrazolo[3,4-d]pyrimidin-4-amine | 347.17004 | 347.0/349.0 | (DMSO-d6) δ = 8.60 (s, 1H), 8.35 (s, 1H), 7.87 (t, J = 7.8 Hz, 1H), 7.50 (d, J = 7.6 Hz, 1H), 7.27-7.22 (m, 1H), 6.33 (s, 1H), 3.77 (d, J = 4.0 Hz, 1H), 1.08-1.03 (m, 4H) |
| 37 | 3-((5-chloropyridin-3-yl)oxy)-1-cyclopropyl-1H-pyrazolo[3,4-d]pyrimidin-4-amine | 302.72 | 303.1 | (DMSO-d6) δ = 8.70 (s, 1H), 8.48 (s, 1H), 8.20 (m, 1H), 8.10 (s, 1H), 7.82 (s, 1H), 7.14 (s, 1H), 3.62 (d, J = 4.0 Hz, 1H), 1.06 (d, J = 2.8 Hz, 2H), 1.00 (d, J = 5.6 Hz, 2H) |

TABLE 5-continued

Compounds Prepared by Method E

| Compound No. | IUPAC Name | MW | LC/MS Observed (M + H) | 1H NMR (400 MHz) |
|---|---|---|---|---|
| 38 | 1-cyclopropyl-3-(pyridin-2-yloxy)-1H-pyrazolo[3,4-d]pyrimidin-4-amine | 268.27 | 269.1 | (DMSO-d6) δ = 8.20 (s, 1H), 8.14 (d, J = 3.6 Hz, 1H), 7.90 (t, J = 6.8 Hz, 1H), 7.20 (d, J = 8.0 Hz, 2H), 3.72-3.66 (m, 1H), 1.06 (d, J = 3.2 Hz, 2H), 1.02-0.97 (m, 2H) |
| 39 | 1-cyclopropyl-3-(pyrazin-2-yloxy)-1H-pyrazolo[3,4-d]pyrimidin-4-amine | 269.26 | 270.1 | (DMSO-d6) δ = 8.65 (s, 1H), 8.42 (d, J = 2.8 Hz, 1H), 8.20 (s, 2H), 7.59-7.12 (m, 2H), 3.74-3.68 (m, 1H), 1.09-1.05 (m, 2H), 1.03-0.98 (m, 2H) |
| 40 | 1-cyclopropyl-3-((6-methylpyridin-2-yl)oxy)-1H-pyrazolo[3,4-d]pyrimidin-4-amine | 282.30 | 283.1 | (DMSO-d6) δ = 8.19 (s, 1H), 7.77 (t, J = 7.6 Hz, 1H), 7.06 (d, J = 6.8 Hz, 1H), 6.97 (d, J = 8.4 Hz, 1H), 3.68 (d, J = 4.0 Hz, 1H), 2.31 (s, 3H), 1.05 (s, 2H), 1.00 (d, J = 6.8 Hz, 2H) |
| 41 | 1-cyclopropyl-3-((5-fluoropyridin-3-yl)oxy)-1H-pyrazolo[3,4-d]pyrimidin-4-amine | 286.26 | 287.1 | (DMSO-d6) δ = 8.62 (s, 1H), 8.46 (d, J = 2.8 Hz, 1H), 8.20 (s, 1H), 7.95-7.92 (m, 1H), 7.91 (s, 1H), 7.13 (s, 1H), 3.65-3.59 (m, 1H), 1.09-1.05 (m, 2H), 1.02-0.98 (m, 2H) |
| 42 | 3-((4-chloropyridin-2-yl)oxy)-1-cyclopropyl-1H-pyrazolo[3,4-d]pyrimidin-4-amine | 302.72 | 303.1 | (DMSO-d6) δ = 8.20 (s, 1H), 8.12 (d, J = 5.6 Hz, 1H), 7.38 (d, J = 1.6 Hz, 1H), 7.32 (t, J = 3.6 Hz, 1H), 3.73-3.68 (m, 1H), 1.09-1.05 (m, 2H), 1.03-1.00 (m, 2H) |
| 43 | 3-((2-chloropyridin-4-yl)oxy)-1-cyclopropyl-1H-pyrazolo[3,4-d]pyrimidin-4-amine | 302.72 | 303.1 | (DMSO-d6) δ = 8.38 (d, J = 6.0 Hz, 1H), 8.22 (s, 1H), 7.86 (br s, 1H), 7.54 (d, J = 2.0 Hz, 1H), 7.43-7.41 (m, 1H), 7.14-7.02 (m, 1H), 3.72-3.67 (m, 1H), 1.13-1.10 (m, 2H), 1.05-1.02 (m, 2H) |
| 44 | 1-cyclopropyl-3-((2-methylpyridin-4-yl)oxy)-1H-pyrazolo[3,4-d]pyrimidin-4-amine | 282.30 | 283 | (DMSO-d6) δ = 8.38 (d, J = 6.0 Hz, 1H), 8.21 (s, 1H), 7.17 (s, 1H), 7.13 (d, J = 5.2 Hz, 1H), 3.70-3.67 (m, 1H), 2.45 (s, 3H), 1.10 (d, J = 3.2 Hz, 2H), 1.02 (d, J = 5.2 Hz, 2H) |
| 64 | 3-((5-chloropyridin-3-yl)oxy)-1-cyclopropyl-1H-pyrazolo[3,4-d]pyrimidin-4-amine | 302.07 | 303.1 | (DMSO-d6) δ = 8.70 (s, 1H), 8.48 (s, 1H), 8.20 (s, 1H), 8.10 (s, 1H), 7.83 (s, 1H), 7.14 (s, 1H), 3.62 (d, J = 4.0 Hz, 1H), 1.07 (d, J = 2.4 Hz, 2H), 1.00 (d, J = 5.6 Hz, 2H) |
| 66 | 1-cyclopropyl-3-(pyrazin-2-yloxy)-1H-pyrazolo[3,4-d]pyrimidin-4-amine | 269.1 | 270.1 | (DMSO-d6) δ = 8.65 (s, 1H), 8.43 (d, J = 2.4 Hz, 1H), 8.21 (s, 2H), 7.86-6.80 (m, 2H), 3.75-3.67 (m, 1H), 1.10-1.04 (m, 2H), 1.04-0.98 (m, 2H) |

TABLE 5-continued

Compounds Prepared by Method E

| Compound No. | IUPAC Name | MW | LC/MS Observed (M + H) | 1H NMR (400 MHz) |
|---|---|---|---|---|
| 67 | 1-cyclopropyl-3((6-methylpyridin-2-yl)oxy)-1H-pyrazolo[3,4-d]pyrimidin-4-amine | 282.12 | 283.1 | (DMSO-d6) δ = 8.19 (s, 1H), 7.78 (t, J = 7.6 Hz, 1H), 7.07 (d, J = 7.2 Hz, 1H), 6.97 (d, J = 8.4 Hz, 1H), 3.68 (d, J = 4.0 Hz, 1H), 2.32 (s, 3H), 1.05 (s, 2H), 1.00 (d, J = 7.2 Hz, 2H) |
| 68 | 1-cyclopropyl-3-((5-fluoropyridin-3-yl)oxy)-1H-pyrazolo[3,4-d]pyrimidin-4-amine | 286.1 | 287.1 | (DMSO-d6) δ = 8.62 (s, 1H), 8.46 (d, J = 2.4 Hz, 1H), 8.21 (s, 1H), 7.94 (td, J = 2.4, 10.4 Hz, 1H), 7.88-7.64 (m, 1H), 7.14 (s, 1H), 3.62 (tt, J = 3.6, 7.2 Hz, 1H), 1.11-1.05 (m, 2H), 1.03-0.96 (m, 2H) |
| 70 | 3-((2-chloropyridin-4-yl)oxy)-1-cyclopropyl-1H-pyrazolo[3,4-d]pyrimidin-4-amine | 302.07 | 303.1 | (DMSO-d6) δ = 8.38 (d, J = 6.0 Hz, 1H), 8.22 (s, 1H), 7.86 (s, 1H), 7.55 (d, J = 2.4 Hz, 1H), 7.43 (dd, J = 2.4, 5.6 Hz, 1H), 7.33-6.98 (m, 1H), 3.70 (tt, J = 3.6, 7.2 Hz, 1H), 1.16-1.09 (m, 2H), 1.07-0.99 (m, 2H) |
| 71 | 1-cyclopropyl-3-((2-methylpyridin-4-yl)oxy)-1H-pyrazolo[3,4-d]pyrimidin-4-amine | 282.12 | 283 | (DMSO-d6) δ = 8.38 (d, J = 6.0 Hz, 1H), 8.21 (s, 1H), 7.17 (s, 1H), 7.13 (d, J = 5.2 Hz, 1H), 3.72-3.62 (m, 1H), 2.45 (s, 3H), 1.10 (d, J = 3.2 Hz, 2H), 1.02 (d, J = 5.2 Hz, 2H) |
| 72 | 1-cyclopropyl-3-(pyrimidin-2-yloxy)-1H-pyrazolo[3,4-d]pyrimidin-4-amine | 269.1 | 270 | (DMSO-d6) δ = 9.45 (s, 1H), 9.16 (s, 1H), 8.67 (d, J = 4.8 Hz, 2H), 8.49 (s, 1H), 7.35 (t, J = 4.8 Hz, 1H), 7.39-7.32 (m, 1H), 3.88 (tt, J = 4.0, 7.2 Hz, 1H), 1.15-1.05 (m, 4H) |
| 73 | 1-cyclopropyl-3-((2-methoxypyridin-4-yl)oxy)-1H-pyrazolo[3,4-d]pyrimidin-4-amine | 298.12 | 299.1 | (METHANOL-d4) δ = 8.35 (s, 1H), 8.16 (d, J = 6.0 Hz, 1H), 7.12-7.11 (m, 1H), 6.96 (d, J = 2.0 Hz, 1H), 3.97 (s, 3H), 3.89-3.85 (m, 1H), 1.26-1.22 (m, 2H), 1.15-1.12 (m, 2H) |
| 74 | 1-cyclopropyl-3-((6-methoxypyridin-2-yl)oxy)-1H-pyrazolo[3,4-d]pyrimidin-4-amine | 298.1 | 299.1 | (DMSO-d6) δ = 8.48 (s, 1H), 8.09 (d, J = 8.0 Hz, 1H), 7.77-7.73 (m, 1H), 6.54 (d, J = 8.0 Hz, 1H), 3.83 (s, 3H), 3.53 (s, 1H), 1.11-0.94 (m, 4H) |
| 75 | 1-cyclopropyl-3-((5-(trifluoromethyl)pyridin-3-yl)oxy)-1H-pyrazolo[3,4-d]pyrimidin-4-amine | 336 | 337 | (METHANOL-d4) δ = 9.20 (s, 1H), 8.82 (s, 1H), 8.62 (s, 1H), 8.45 (s, 1H), 3.43-3.37 (m, 1H), 1.20-1.06 (m, 4H) |
| 76 | 2-((4-amino-1-cyclopropyl-1H-pyrazolo[3,4-d]pyrimidin-3-yl)oxy)isonicotinic acid | 312.1 | 313.1 | (METHANOL-d4) δ = 8.22-8.21 (m, 2H), 7.73 (s, 1H), 7.66 (d, J = 5.2 Hz, 1H), 3.65 (tt, J = 3.6, 7.2 Hz, 1H), 1.22-1.17 (m, 2H), 1.09-1.07 (m, 2H) |

TABLE 5-continued

Compounds Prepared by Method E

| Compound No. | IUPAC Name | MW | LC/MS Observed (M + H) | 1H NMR (400 MHz) |
|---|---|---|---|---|
| 77 | 1-cyclopropyl-3-((4-(trifluoromethyl)pyridin-2-yl)oxy)-1H-pyrazolo[3,4-d]pyrimidin-4-amine | 336.09 | 337 | (METHANOL-d4) δ = 8.41 (d, J = 5.2 Hz, 1H), 8.34 (s, 1H), 7.68 (s, 1H), 7.54 (d, J = 5.2 Hz, 1H), 3.88-3.83 (m, 1H), 1.26-1.20 (m, 2H), 1.14-1.13 (m, 2H) |
| 78 | 2-((4-amino-1-cyclopropyl-1H-pyrazolo[3,4-d]pyrimidin-3-yl)oxy)isonicotinonitrile | 293.1 | 294.1 | (DMSO-d6) δ = 8.36 (d, J = 5.2 Hz, 1H), 8.30 (s, 1H), 7.80 (s, 1H), 7.66-7.64 (m, 1H), 3.78-3.74 (m, 1H), 1.07-1.00 (m, 4H) |
| 79 | 1-cyclopropyl-3-((3,5-dichloropyridin-2-yl)oxy)-1H-pyrazolo[3,4-d]pyrimidin-4-amine | 336.02 | 337 | (METHANOL-d4) δ = 8.32 (s, 1H), 8.17 (d, J = 2.8 Hz, 1H), 8.11 (d, J = 2.0 Hz, 1H), 3.82 (tt, J = 3.6, 7.2 Hz, 1H), 1.22-1.18 (m, 2H), 1.12-1.08 (m, 2H) |
| 80 | 1-cyclopropyl-3-((5-(trifluoromethyl)pyridin-2-yl)oxy)-1H-pyrazolo[3,4-d]pyrimidin-4-amine | 336 | 337 | (DMSO-d6) δ 8.58 (s, 1H), 8.30-8.28 (m, 1H), 8.22-8.19 (m, 1H), 7.39 (d, J = 8.8 Hz, 1H), 3.75-3.70 (m, 1H), 1.10-1.05 (m, 2H), 1.04-1.00 (m, 2H) |
| 81 | 1-cyclopropyl-3-((6-(trifluoromethyl)pyrimidin-4-yl)oxy)-1H-pyrazolo[3,4-d]pyrimidin-4-amine | 337 | 338 | (DMSO-d6) δ = 9.34 (s, 1H), 8.41 (s, 1H), 8.39 (s, 1H), 8.35 (s, 1H), 7.42 (s, 1H), 3.51-3.46 (m, 1H), 0.97-0.92 (m, 2H), 0.87-0.84 (m, 2H) |
| 82 | 1-cyclopropyl-3-((4-fluoropyridin-2-yl)oxy)-1H-pyrazolo[3,4-d]pyrimidin-4-amine | 286.1 | 287.1 | (DMSO-d6) δ = 9.78 (s, 1H), 9.12 (s, 1H), 8.42 (s, 1H), 8.23 (d, J = 6.0 Hz, 1H), 7.38-7.37 (m, 1H), 7.22-7.18 (m, 1H), 3.81-3.75 (m, 1H), 1.15-1.12 (m, 2H), 1.09-1.06 (m, 2H) |
| 83 | 1-cyclopropyl-3((4-methylpyridin-2-yl)oxy)-1H-pyrazolo[3,4-d]pyrimidin-4-amine | 282.1 | 283.1 | (DMSO-d6) δ = 8.38 (s, 1H), 8.01-8.00 (m, 1H), 7.11-7.06 (m, 2H), 3.80-3.71 (m, 1H), 2.37 (s, 3H), 1.13-1.03 (m, 4H) |
| 84 | 1-cyclopropyl-3-((4-(trifluoromethyl)pyrimidin-2-yl)oxy)-1H-pyrazolo[3,4-d]pyrimidin-4-amine | 337 | 338 | (DMSO-d6) δ = 9.02 (d, J = 4.8, 1H), 8.34 (s, 1H), 7.89 (d, J = 4.8 Hz, 1H), 3.85-3.79 (m, 1H), 1.11-1.05 (m, 4H) |
| 85 | ethyl 2-((4-amino-1-cyclopropyl-1H-pyrazolo[3,4-d]pyrimidin-3-yl)oxy)isonicotinate | 340.1 | 341.1 | (DMSO-d6) δ = 8.34-8.33 (m, 2H), 7.64-7.63 (m, 2H), 4.40 (q, J = 7.2 Hz, 2H), 3.81-3.77 (m, 1H), 1.36 (t, J = 7.2 Hz, 3H), 1.09-1.04 (m, 4H) |
| 86 | (2-((4-amino-1-cyclopropyl-1H-pyrazolo[3,4-d]pyrimidin-3-yl)oxy)pyrimidin-4-yl)methanol | 298.1 | 299.1 | (METHANOL-d4) δ = 8.22 (s, 1H), 8.12 (d, J = 5.2 Hz, 1H), 7.37 (s, 1H), 7.21 (d, J = 5.2 Hz, 1H), 4.71 (s, 2H), 3.67-3.62 (m, 1H), 1.21-1.16 (m, 2H), 1.09-1.02 (m, 2H) |
| 87 | 1-cyclopropyl-3-((5-methylpyridin-2-yl)oxy)-1H-pyrazolo[3,4-d]pyrimidin-4-amine | 282.1 | 283.1 | (METHANOL-d4) δ = 8.34 (s, 1H), 8.05 (s, 1H), 7.81-7.79 (m, 1H), 7.34 (d, J = 8.4 Hz, 1H), 3.85-3.79 (m, 1H), 2.35 (s, 3H), 1.24-1.19 (m, 2H), 1.12-1.08 (m, 2H) |

TABLE 5-continued

Compounds Prepared by Method E

| Compound No. | IUPAC Name | MW | LC/MS Observed (M + H) | 1H NMR (400 MHz) |
|---|---|---|---|---|
| 88 | 1-cyclopropyl-3-((4-methoxypyridin-2-yl)oxy)-1H-pyrazolo[3,4-d]pyrimidin-4-amine | 298.1 | 299.1 | (METHANOL-d4) δ = 8.34 (s, 1H), 8.02 (d, J = 6.0 Hz, 1H), 7.00 (d, J = 2.0 Hz, 1H), 6.89-6.87 (m, 1H), 3.95 (s, 3H), 3.88-3.84 (m, 1H), 1.26-1.22 (m, 2H), 1.15-1.10 (m, 2H) |
| 89 | 3-((4-chloro-5-fluoropyridin-2-yl)oxy)-1-cyclopropyl-1H-pyrazolo[3,4-d]pyrimidin-4-amine | 320 | 321 | (METHANOL-d4) δ = 8.44 (d, J = 2.0 Hz, 1H), 8.34 (s, 1H), 7.64 (d, J = 5.6 Hz, 1H), 3.81-3.75 (m, 1H), 1.18-1.16 (m, 2H), 1.11-1.09 (m, 2H) |
| 90 | 3-((6-chloropyrimidin-4-yl)oxy)-1-cyclopropyl-1H-pyrazolo[3,4-d]pyrimidin-4-amine | 303 | 304 | (METHANOL-d4) δ = 8.62 (s, 1H), 8.35 (s, 1H), 7.52 (s, 1H), 3.91-3.86 (m, 1H), 1.26-1.23 (m, 2H), 1.17-1.14 (m, 2H) |
| 91 | 3-((2-chloropyrimidin-4-yl)oxy)-1-cyclopropyl-1H-pyrazolo[3,4-d]pyrimidin-4-amine | 303 | 304 | (DMSO-d6) δ = 8.72 (d, J = 6.4 Hz, 1H), 8.37 (s, 1H), 7.38 (d, J = 5.6 Hz, 1H), 3.86-3.80 (m, 1H), 1.11-1.09 (m, 2H), 1.08-1.06 (m, 2H) |
| 92 | 1-cyclopropyl-3-((5-(trifluoromethyl)pyridazin-3-yl)oxy)-1H-pyrazolo[3,4-d]pyrimidin-4-amine | 337 | 338 | (METHANOL-d4) δ = 9.42 (s, 1H), 8.38 (s, 1H), 8.12 (s, 1H), 3.92-3.86 (m, 1H), 1.28-1.22 (m, 2H), 1.18-1.13 (m, 2H) |
| 93 | 3-((6-chloropyridazin-4-yl)oxy)-1-cyclopropyl-1H-pyrazolo[3,4-d]pyrimidin-4-amine | 303 | 304 | (DMSO-d6) δ = 9.42 (d, J = 2.8 Hz, 1H), 8.36 (s, 1H), 7.93 (d, J = 2.4 Hz, 1H), 3.79-3.74 (m, 1H), 1.16-1.14 (m, 2H), 1.09-1.06 (m, 2H) |
| 94 | 1-cyclopropyl-3-((5-fluoropyridin-2-yl)oxy)-1H-pyrazolo[3,4-d]pyrimidin-4-amine | 286 | 287.1 | (DMSO-d6) δ = 8.32 (s, 1H), 8.17 (d, J = 2.8 Hz, 1H), 7.92-7.88 (m, 1H), 7.32-7.29 (m, 1H), 3.77-3.71 (m, 1H), 1.08-1.02 (m, 4H) |
| 95 | 1-cyclopropyl-3-((3-fluoropyridin-2-yl)oxy)-1H-pyrazolo[3,4-d]pyrimidin-4-amine | 286 | 287 | (DMSO-d6) δ = 8.36 (s, 1H), 7.96-7.89 (m, 2H), 7.31-7.29 (m, 1H), 3.79-3.74 (m, 1H), 1.10-1.03 (m, 4H) |
| 96 | 2-((4-amino-1-cyclopropyl-1H-pyrazolo[3,4-d]pyrimidin-3-yl)oxy)-5-fluoroisonicotinonitrile | 311 | 312 | (METHANOL-d4) δ = 8.77 (d, J = 2.4 Hz, 1H), 8.34 (s, 1H), 8.15 (d, J = 6.4 Hz, 1H), 3.81-3.75 (m, 1H), 1.18-1.17 (m, 2H), 1.11-1.10 (m, 2H) |
| 97 | 1-cyclopropyl-3-((6-(trifluoromethyl)pyridin-2-yl)oxy)-1H-pyrazolo[3,4-d]pyrimidin-4-amine | 336.09 | 337.1 | 1H NMR (100 MHz, DMSO-d6) δ = 8.33 (s, 1H), 8.20 (m, J = 9.2 Hz, 1H), 7.75 (d, J = 7.6 Hz, 1H), 7.54 (d, J = 8.4 Hz, 1H), 3.81-3.75 (m, 1H), 1.10-1.01 (m, 4H) |
| 98 | 1-cyclopropyl-3-((2-(trifluoromethyl)pyridin-4-yl)oxy)-1H-pyrazolo[3,4-d]pyrimidin-4-amine | 336.09 | 337.1 | 1H NMR (400 MHz, DMSO-d6) δ = 8.76 (d, J = 5.6 Hz, 1H), 8.34 (s, 1H), 7.98 (d, J = 2.4 Hz, 1H), 7.77-7.75 (m, 1H), 3.80-3.75 (m, 1H), 1.18-1.04 (m, 4H) |

Synthesis Method G: General Procedure Represented by the Preparation of 3-((1H-indol-3-yl)methyl)-1-cyclopropyl-1H-pyrazolo[3,4-d]pyrimidin-4-amine

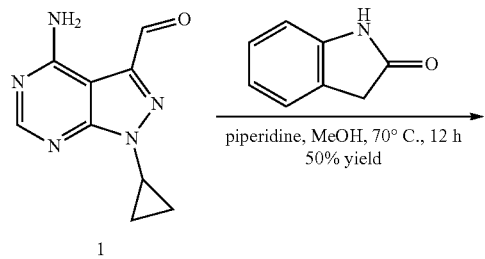

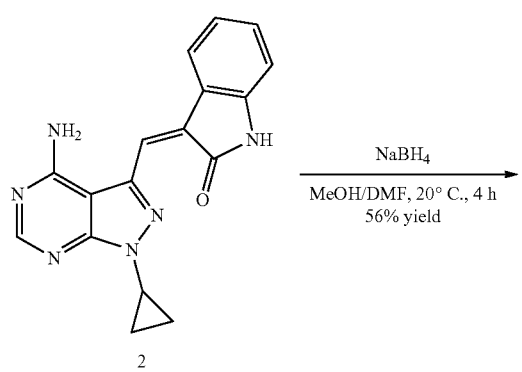

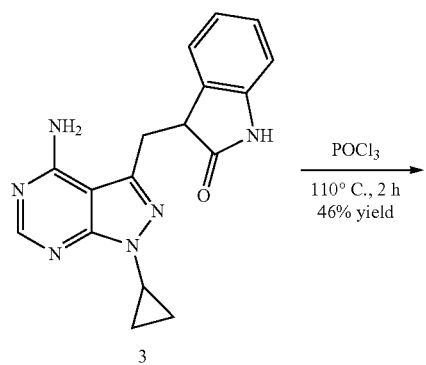

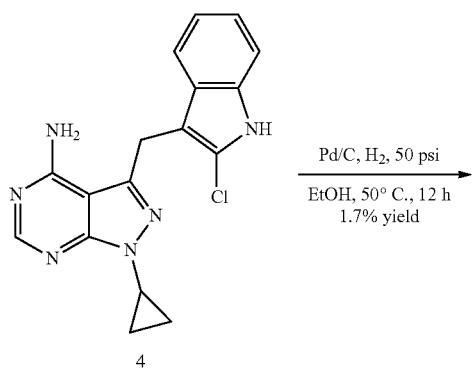

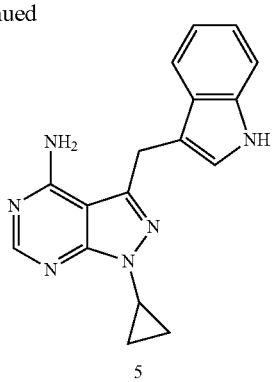

Step 1

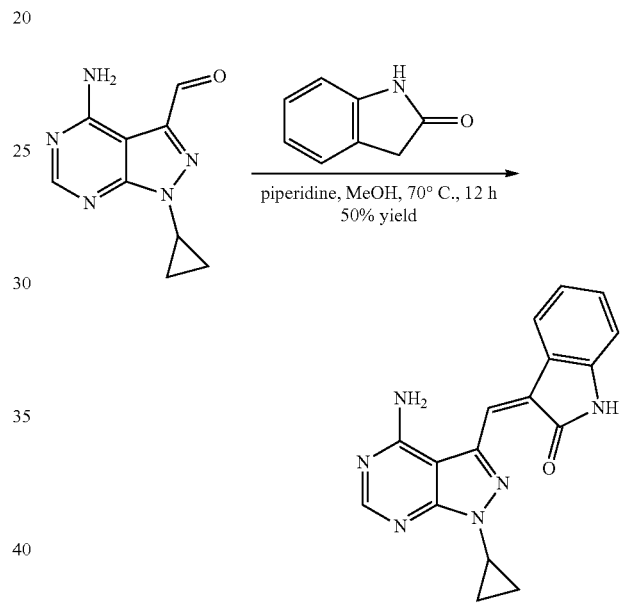

4-Amino-1-cyclopropyl-1H-pyrazolo[3,4-d]pyrimidine-3-carbaldehyde (100.0 mg, 492.1 μmol, 1.0 eq), indolin-2-one (65.5 mg, 492.1 μmol, 1.0 eq), piperidine (431.1 mg, 5.0 mmol, 0.5 mL, 10.2 eq) and MeOH (20.0 mL) were combined and degassed and purged with $N_2$ three times, and stirred at 70° C. for 12 h under $N_2$ atmosphere. The mixture was filtered and the filter cake was dried under reduced pressure to give 3-((4-amino-1-cyclopropyl-1H-pyrazolo[3,4-d]pyrimidin-3-yl)methylene)indolin-2-one (80.0 mg, 246.2 μmol, 50.0% yield, 98.7% purity) as a yellow solid without further purification. $^1$H NMR: (400 MHz, DMSO-$d_6$) δ=10.60 (s, 1H), 8.68 (d, J=7.6 Hz, 1H), 8.29 (s, 1H), 7.74 (s, 1H), 7.57 (s, 2H), 7.29 (t, J=7.6 Hz, 1H), 7.00 (t, J=7.6 Hz, 1H), 6.88 (d, J=7.6 Hz, 1H), 4.08 (tt, J=3.6, 7.6 Hz, 1H), 3.37 (s, 1H), 1.33-1.28 (m, 2H), 1.23-1.17 (m, 2H). LCMS: (M+H)$^+$: 319.1, Rt: 2.232 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and

Step 2

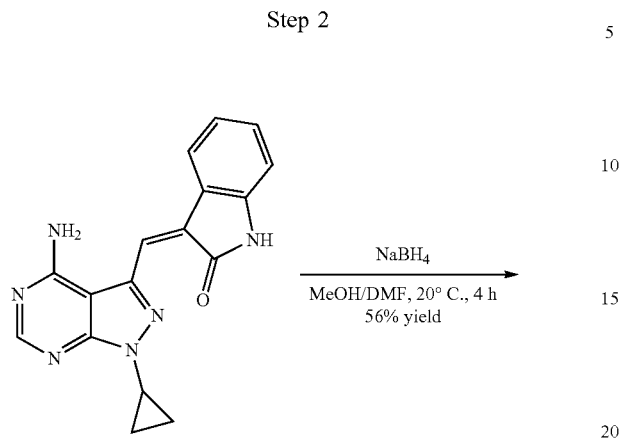

To a solution of 3-((4-amino-1-cyclopropyl-1H-pyrazolo[3,4-d]pyrimidin-3-yl)methylene)indolin-2-one (0.5 g, 1.5 mmol, 1.0 eq) in MeOH (10 mL) and DMF (5 mL) was added NaBH$_4$ (594.2 mg, 15.7 mmol, 10.0 eq). The mixture was stirred at 20° C. for 4 h, quenched with water (10 mL), filtered and the filter cake was dried under reduced pressure to give a residue, which was purified by prep-HPLC (condition: TFA) to give 3-((4-amino-1-cyclopropyl-1H-pyrazolo[3,4-d]pyrimidin-3-yl)methyl)indolin-2-one (0.3 g, 889.6 μmol, 56.6% yield, 95% purity) as a white solid. $^1$H NMR: (400 MHz, METHANOL-d$_4$) δ=8.27 (s, 1H), 7.22-7.16 (m, 1H), 7.10 (d, J=7.6 Hz, 1H), 6.97-6.91 (m, 1H), 6.89 (d, J=7.6 Hz, 1H), 3.97 (t, J=5.6 Hz, 1H), 3.91-3.84 (m, 1H), 3.76-3.68 (m, 1H), 3.56-3.47 (m, 1H), 1.16-1.08 (m, 1H), 1.07-0.99 (m, 3H). LCMS: (M+H)$^+$: 321.1, Rt: 2.205 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Step 3

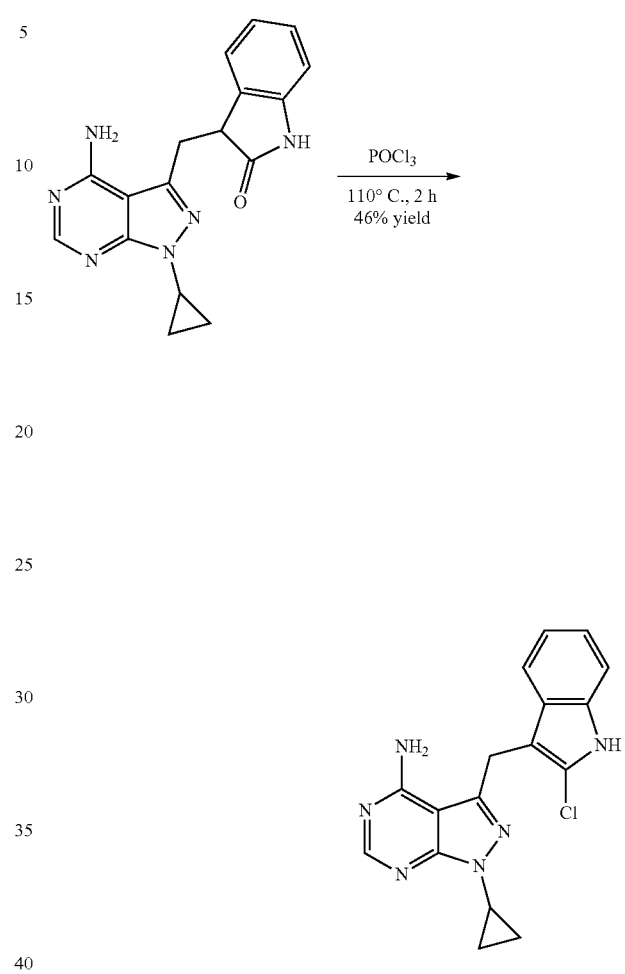

A mixture of 3-((4-amino-1-cyclopropyl-1H-pyrazolo[3,4-d]pyrimidin-3-yl)methyl)indolin-2-one (0.2 g, 624.3 μmol, 1.0 eq) in POCl$_3$ (8.2 g, 53.8 mmol, 5.0 mL, 86.1 eq) was degassed and purged with N$_2$ three times, stirred at 110° C. for 2 h under N$_2$ atmosphere and concentrated under reduced pressure. The residue was quenched with MeOH (2 mL) and purified by prep-HPLC (condition: TFA) to give 3-((2-chloro-1H-indol-3-yl)methyl)-1-cyclopropyl-1H-pyrazolo[3,4-d]pyrimidin-4-amine (0.1 g, 291.3 μmol, 46.6% yield, 98.7% purity) as a yellow solid. $^1$H NMR: (400 MHz, CDCl$_3$) δ=7.44-7.39 (m, 2H), 7.35 (t, J=7.2 Hz, 2H), 7.32-7.27 (m, 1H), 4.67 (s, 2H), 4.61 (s, 2H), 4.47 (s, 2H), 3.12-3.04 (m, 1H), 1.16-1.05 (m, 4H). LCMS: (M+H)$^+$: 339.1, Rt: 2.206 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Step 4

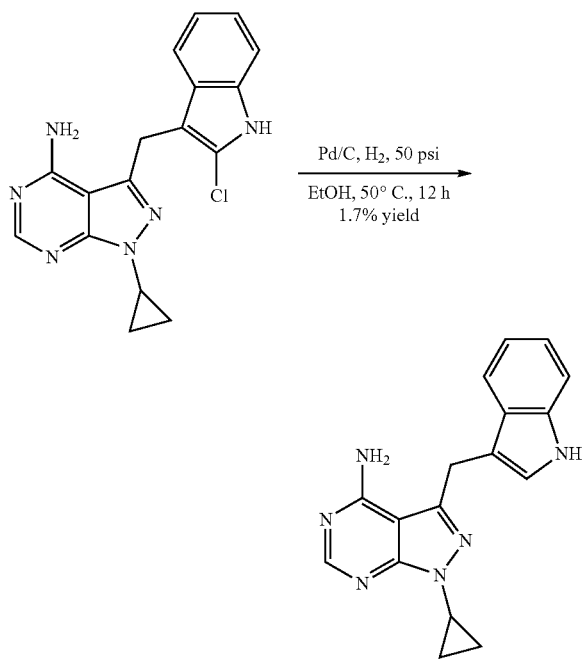

Pd/C, H₂, 50 psi
EtOH, 50° C., 12 h
1.7% yield

To a solution of 3-((2-chloro-H-indol-3-yl)methyl)-1-cyclopropyl-1H-pyrazolo[3,4-d]pyrimidin-4-amine (0.1 g, 295.1 μmol, 1.0 eq) in EtOH (10 mL) was added Pd/C (10%, 0.1 g). The suspension was degassed and purged with $H_2$ three times and stirred under $H_2$ (50 Psi) at 20° C. for 12 h. The mixture was filtered over celite and the filtrate concentrated under reduced pressure to give a residue, which was purified by prep-HPLC (neutral condition) to afford 3-((1H-indo-3-yl)methyl)-1-cyclopropyl-1H-pyrazolo[3,4-d]pyrimidin-4-amine (Compound 32) (1.7 mg, 5.0 μmol, 1.7% yield, 91% purity) as a white solid. $^1$H NMR: (400 MHz, METHANOL-d₄) δ=8.13 (s, 1H), 7.37 (dd, J=8.0, 12.0 Hz, 2H), 7.13-7.06 (m, 2H), 6.98-6.92 (m, 1H), 4.39 (s, 2H), 3.70 (tt, J=7.6 Hz, 1H), 1.31-1.22 (m, 2H), 1.19-1.10 (m, 2H). LCMS: (M+H)⁺: 305.1, Rt: 2.063 m. LC/MS (The gradient was 10-100% B in 3.4 min with a hold at 100% B for 0.45 m, 100-10% in 0.01 min, and then held at 310% B for 0.65 min (0.8 mL/min flow rate). Mobile phase was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 particles). Detection methods are diode array (DAD) and evaporative light scattering (ELSD) detection as well as positive electrospray ionization (MS).

The following compounds were prepared in a similar manner as described in method G using different starting materials.

TABLE 6

Compounds Prepared by Method E

| Compound No. | IUPAC Name | MW | LC/MS Observed (M + H) | 1H NMR (400 MHz) |
|---|---|---|---|---|
| 33 | (Z)-3-((4-amino-1-cyclopropyl-1H-pyrazolo[3,4-d]pyrimidin-3-yl)methylene)indolin-2-one | 318.33 | 319.1 | (DMSO-d6) δ = 10.60 (s, 1H), 8.68 (d, J = 7.6 Hz, 1H), 8.29 (s, 1H), 7.74 (s, 1H), 7.57 (s, 2H), 7.29 (t, J = 7.6 Hz, 1H), 7.00 (t, J = 7.6 Hz, 1H), 6.88 (d, J = 7.6 Hz, 1H), 4.08 (tt, J = 3.6, 7.6 Hz, 1H), 3.37 (s, 1H), 1.33-1.28 (m, 2H), 1.23-1.17 (m, 2H) |
| 34 | 3-((4-amino-1-cyclopropyl-1H-pyrazolo[3,4-d]pyrimidin-3-yl)methyl)indolin-2-one | 320.35 | 321.1 | (METHANOL-d4) δ = 8.27 (s, 1H), 7.22-7.16 (m, 1H), 7.10 (d, J = 7.6 Hz, 1H), 6.97-6.91 (m, 1H), 6.89 (d, J = 7.6 Hz, 1H), 3.97 (t, J = 5.6 Hz, 1H), 3.91-3.84 (m, 1H), 3.76-3.68 (m, 1H), 3.56-3.47 (m, 1H), 1.16-1.08 (m, 1H), 1.07-0.99 (m, 3H) |
| 35 | 3-((2-chloro-1H-indol-3-yl)methyl)-1-cyclopropyl-1H-pyrazolo[3,4-d]pyrimidin-4-amine | 337.79 | 339.1 | (CHLOROFORM-d) δ = 7.44-7.39 (m, 2H), 7.35 (t, J = 7.2 Hz, 2H), 7.32-7.27 (m, 1H), 4.67 (s, 2H), 4.61 (s, 2H), 4.47 (s, 2H), 3.12-3.04 (m, 1H), 1.16-1.05 (m, 4H) |
| 36 | 3-((1H-indol-3-yl)methyl)-1-cyclopropyl-1H-pyrazolo[3,4-d]pyrimidin-4-amine | 304.35 | 305.1 | (METHANOL-d4) δ = 8.13 (s, 1H), 7.37 (dd, J = 8.0, 12.0 Hz, 2H), 7.13-7.06 (m, 2H), 6.98-6.92 (m, 1H), 4.39 (s, 2H), 3.70 (tt, J = 3.6, 7.2 Hz, 1H), 1.31-1.22 (m, 2H), 1.19-1.10 (m, 2H) |

TABLE 6-continued

Compounds Prepared by Method E

| Compound No. | IUPAC Name | MW | LC/MS Observed (M + H) | 1H NMR (400 MHz) |
|---|---|---|---|---|
| 45 | 1-cyclopropyl-3-((5-fluoro-1H-indol-3-yl)methyl)-1H-pyrazolo[3,4-d]pyrimidin-4-amine | 321.33 | 323.1 | (DMSO-d6) δ = 10.98 (s, 1H), 8.29 (s, 1H), 7.34-7.30 (m, 2H), 7.24 (dd, J = 2.4, 10.4 Hz, 1H), 6.88 (dt, J = 2.4, 9.2 Hz, 1H), 4.37 (s, 2H), 3.84 (tt, J = 3.6, 7.2 Hz, 1H), 1.16-1.17 (m, 2H), 1.08 (dd, J = 4.8, 6.8 Hz, 2H) |
| 46 | (Z)-3-((4-amino-1-cyclopropyl-1H-pyrazolo[3,4-d]pyrimidin-3-yl)methylene)-5-fluoroindolin-2-one | 336.32 | 337.1 | (DMSO-d6) 5 = 8.64 (d, J = 10.0 Hz; 1H), 8.31 (s, 1H), 7.82-7.80 (m, 3H), 7.14 (t, J = 8.8 Hz, 1H, 6.84 (dd, J = 4.8, 8.0 Hz, 1H), 4.08 (s, 1H), 1.28-1.19 (m, 4H) |
| 47 | 3-((4-amino-1-cyclopropyl-1H-pyrazolo[3,4-d]pyrimidin-3-yl)methyl)-5-fluoroindolin-2-one | 338.34 | 339.1 | (DMSO-d6) δ = 10.48 (s, 1H), 8.29 (s, 1H), 6.95 (s, 2H), 6.79 (s, 1H), 3.93 (s, 1H), 3.82 (s, 1H), 3.63-3.60 (m, 1H), 3.49-3.43 (m, 1H), 0.97 (d, J = 7.6 Hz, 3H), 0.86 (s, 1H) |
| 48 | 3-((2-chloro-5-fluoro-1H-indol-3-yl)methyl)-1-cyclopropyl-1H-pyrazolo[3,4-d]pyrimidin-4-amine | 355.78 | 357 | (DMSO-d6) δ = 8.32-8.29 (m, 1H), 7.30-7.26 (m, 1H), 7.11 (d, J = 8.0 Hz, 1H), 6.97-6.93 (m, 1H), 4.37 (d, J = 4.0 Hz, 2H), 3.72-3.70 (m, 1H), 1.01-1.00 (m, 4H) |
| 49 | (Z)-3-((4-amino-1-cyclopropyl-1H-pyrazolo[3,4-d]pyrimidin-3-yl)methylene)-1,3-dihydro-2H-pyrrolo[2,3-b]pyridin-2-one | 319.32 | 320.1 | (DMSO-d6) δ = 11.22 (s, 1H), 8.93 (d, J = 7.2 Hz, 1H), 8.28 (s, 1H), 8.13-8.12 (m, 1H), 7.89 (s, 1H), 7.64 (s, 2H), 7.05 (dd, J = 5.2, 7.6 Hz, 1H), 4.06 (dt, J = 3.2, 7.2 Hz, 1H), 1.29-1.27 (m, 2H), 1.21-1.18 (m, 2H) |
| 50 | 3-((4-amino-1-cyclopropyl-1H-pyrazolo[3,4-d]pyrimidin-3-yl)methyl)-1,3-dihydro-2H-pyrrolo[2,3-b]pyridin-2-one | 321.34 | 322.1 | (METHANOL-d4) δ = 8.30 (s, 1H), 8.06 (dd, J = 1.6, 5.6 Hz, 1H), 7.54 (dd, J = 1.2, 7.6 Hz, 1H), 6.97 (dd, J = 5.6, 7.2 Hz, 1H), 3.91 (tt, J = 3.6, 7.2 Hz, 1H), 3.78-3.74 (m, 1H), 3.66-3.62 (m, 1H), 1.06-1.00 (m, 3H), 1.00-0.87 (m, 1H) |
| 51 | 3-((2-chloro-1H-pyrrolo[2,3-b]pyridin-3-yl)methyl)-1-cyclopropyl-1H-pyrazolo[3,4-d]pyrimidin-4-amine | 338.77 | 340.1 | (DMSO-d6) δ = 12.37 (s, 1H), 8.17 (dd, J = 1.2, 4.8 Hz, 1H), 8.14 (s, 1H), 7.65 (dd, J = 1.6, 8.0 Hz, 1H), 7.01 (dd, J = 4.8, 8.0 Hz, 1H), 4.37 (s, 2H), 3.65 (tt, J = 3.6, 7.2 Hz, 1H), 1.04-0.95 (m, 4H) |
| 99 | 1-cyclopropyl-3-((5-fluoro-1H-indol-3-yl)methyl)-1H-pyrazolo[3,4-d]pyrimidin-4-amine | 322.1 | 323.1 | (DMSO-d6) δ = 10.96 (s, 1H), 8.27 (s, 1H), 7.34-7.28 (m, 2H), 7.22 (dd, J = 2.4, 10.4 Hz, 1H), 6.87 (dt, J = 2.4, 9.2 Hz, 1H), 4.35 (s, 2H), 3.82 (tt, J = 3.6, 7.2 Hz, 1H), 1.17-1.11 (m, 2H), 1.08 (dd, J = 4.8, 6.8 Hz, 2H) |
| 100 | (Z)-3-((4-amino-1-cyclopropyl-1H-pyrazolo[3,4-d]pyrimidin-3-yl)methylene)-5-fluoroindolin-2-one | 336.1 | 337.1 | (DMSO-d6) δ = 8.64 (d, J = 10.0 Hz, 1H), 8.31 (s, 1H), 7.82-7.80 (m, 3H), 7.14 (t, J = 8.8 Hz, 1H), 6.84 (dd, J = 4.4, 8.0 Hz, 1H), 4.08 (s, 1H), 1.29-1.19 (m, 4H) |
| 101 | 3-((4-amino-1-cyclopropyl-1H-pyrazolo[3,4-d]pyrimidin-3-yl)methyl)-5-fluoroindolin-2-one | 338.1 | 339.1 | (DMSO-d6) δ = 10.48 (s, 1H), 8.29 (s, 1H), 6.95 (s, 2H), 6.79 (s, 1H), 3.93 (s, 1H), 3.82 (s, 1H), 3.64-3.60 (m, 1H), 3.49-3.43 (m, 1H), 0.98 (d, J = 7.6 Hz, 3H), 0.86 (s, 1H) |

TABLE 6-continued

Compounds Prepared by Method E

| Compound No. | IUPAC Name | MW | LC/MS Observed (M + H) | 1H NMR (400 MHz) |
|---|---|---|---|---|
| 102 | 3-((2-chloro-5-fluoro-1H-indol-3-yl)methyl)-1-cyclopropyl-1H-pyrazolo[3,4-d]pyrimidin-4-amine | 356.1 | 357 | (DMSO-d6) δ = 8.32-8.30 (m, 1H), 7.30-7.26 (m, 1H), 7.11 (d, J = 10.0 Hz, 1H), 6.97-6.94 (m, 1H), 4.37 (d, J = 2.0 Hz, 2H), 3.72-3.71 (m, 1H), 1.01-1.00 (m, 4H) |
| 103 | (Z)-3-((4-amino-1-cyclopropyl-1H-pyrazolo[3,4-d]pyrimidin-3-yl)methylene)-1,3-dihydro-2H-pyrrolo[2,3-b]pyridin-2-one | 319.1 | 320.1 | (DMSO-d6) δ = 11.22 (s, 1H), 8.93 (d, J = 7.2 Hz, 1H), 8.28 (s, 1H), 8.15-8.10 (m, 1H), 7.89 (s, 1H), 7.64 (s, 2H), 7.05 (dd, J = 5.2, 7.6 Hz, 1H), 4.06 (dt, J = 3.2, 7.2 Hz, 1H), 1.33-1.25 (m, 2H), 1.23-1.16 (m, 2H) |
| 104 | 3-((4-amino-1-cyclopropyl-1H-pyrazolo[3,4-d]pyrimidin-3-yl)methyl)-1,3-dihydro-2H-pyrrolo[2,3-b]pyridin-2-one | 321.1 | 322.1 | (METHANOL-d4) δ = 8.30 (s, 1H), 8.06 (dd, J = 1.6, 5.6 Hz, 1H), 7.54 (dd, J = 1.6, 7.2 Hz, 1H), 6.97 (dd, J = 5.2, 7.2 Hz, 1H), 3.91 (tt, J = 3.6, 7.2 Hz, 1H), 3.78-3.74 (m, 1H), 3.66-3.62 (m, 1H), 1.06-1.01 (m, 3H), 1.00-0.92 (m, 1H) |
| 105 | 3-((2-chloro-1H-pyrrolo[2,3-b]pyridin-3-yl)methyl)-1-cyclopropyl-1H-pyrazolo[3,4-d]pyrimidin-4-amine | 339.1 | 340.1 | (DMSO-d6) δ = 12.37 (s, 1H), 8.17 (dd, J = 1.6, 4.8 Hz, 1H), 8.14 (s, 1H), 7.65 (dd, J = 1.6, 8.0 Hz, 1H), 7.01 (dd, J = 4.4, 8.0 Hz, 1H), 4.37 (s, 2H), 3.65 (tt, J = 3.6, 7.2 Hz, 1H), 1.04-0.95 (m, 4H) |
| 106 | 3-((1H-pyrrolo[2,3-b]pyridin-3-yl)methyl)-1-cyclopropyl-1H-pyrazolo[3,4-d]pyrimidin-4-amine | 305.1 | 306.1 | (DMSO-d6) δ = 12.08 (s, 1H), 8.47 (s, 1H), 8.31 (d, J = 4.8 Hz, 1H), 8.21 (d, J = 7.6 Hz, 1H), 7.53 (s, 1H), 7.27-7.24 (m, 1H), 4.53 (s, 2H), 3.91-3.85 (m, 1H), 1.14-1.09 (m, 4H) |

Synthesis Method H: General Procedure Represented by the Preparation of 3-((4-chloropyridin-2-yl)oxy)-1-cyclobutyl-1H-pyrazolo[3,4-d]pyrimidin-4-amine

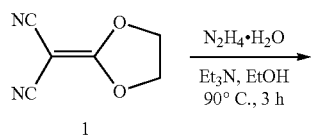
1

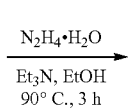
N₂H₄·H₂O
Et₃N, EtOH
90° C., 3 h

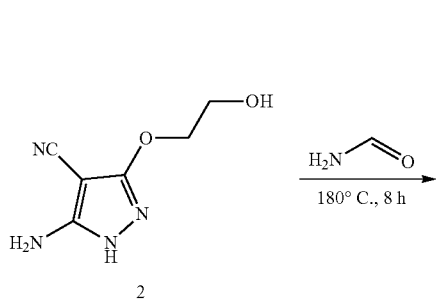
2

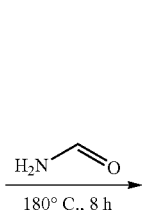
H₂N—CHO
180° C., 8 h

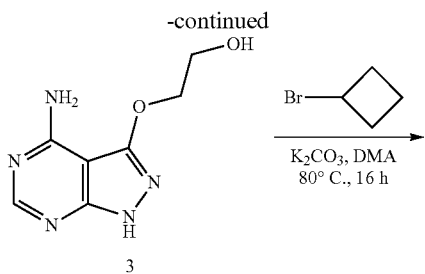
3

Br—cyclobutyl
K₂CO₃, DMA
80° C., 16 h

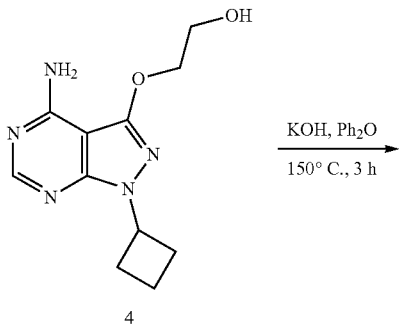
4

KOH, Ph₂O
150° C., 3 h

-continued

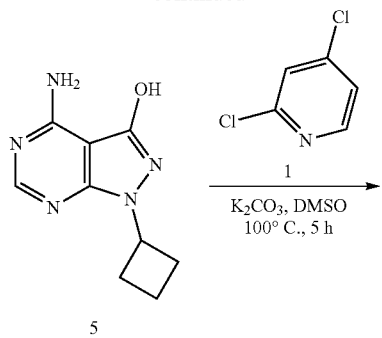

Step 2. Procedure for Preparation of 2-((4-amino-1H-pyrazolo[3,4-d]pyrimidin-3-yl)oxy)ethan-1-ol (3)

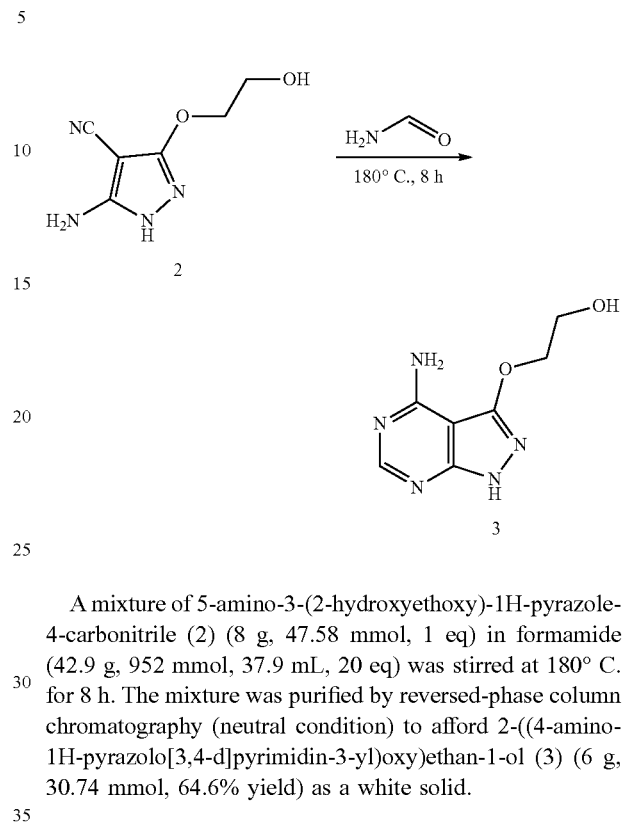

A mixture of 5-amino-3-(2-hydroxyethoxy)-1H-pyrazole-4-carbonitrile (2) (8 g, 47.58 mmol, 1 eq) in formamide (42.9 g, 952 mmol, 37.9 mL, 20 eq) was stirred at 180° C. for 8 h. The mixture was purified by reversed-phase column chromatography (neutral condition) to afford 2-((4-amino-1H-pyrazolo[3,4-d]pyrimidin-3-yl)oxy)ethan-1-ol (3) (6 g, 30.74 mmol, 64.6% yield) as a white solid.

Step 3. Procedure for Preparation of 2-((4-amino-1-cyclobutyl-H-pyrazolo[3,4-d]pyrimidin-3-yl)oxy)ethan-1-ol (4)

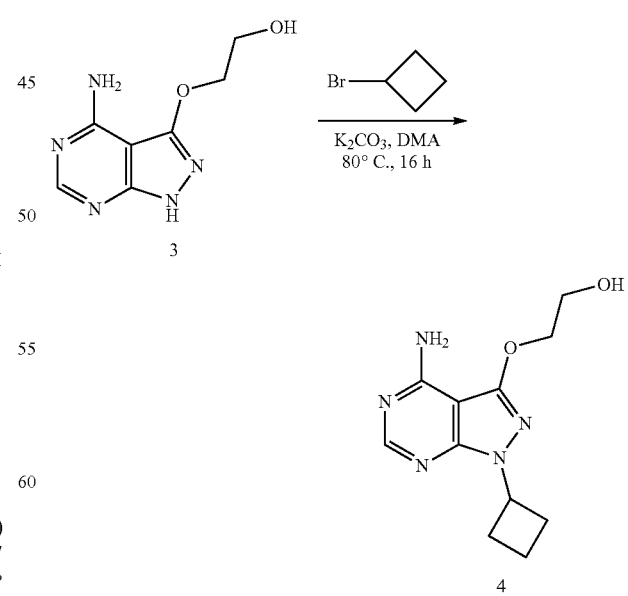

Step 1. Procedure for Preparation of 5-amino-3-(2-hydroxyethoxy)-1H-pyrazole-4-carbonitrile (2)

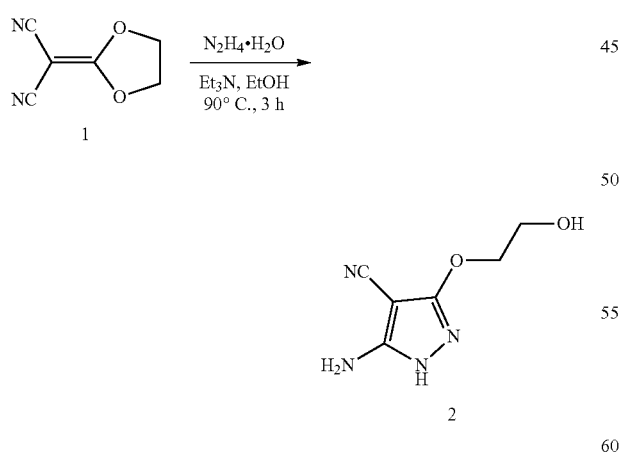

A mixture of 2-(1,3-dioxolan-2-ylidene)malononitrile (1) (10 g, 73.5 mmol, 1.00 eq) and N₂H₄·H₂O (7.51 g, 147 mmol, 7.29 mL, 2 eq) in EtOH (80 mL) was stirred at 90° C. for 3 h. The mixture was concentrated under reduced pressure to afford 5-amino-3-(2-hydroxyethoxy)-1H-pyrazole-4-carbonitrile (2) (10 g, crude) as a yellow solid.

To a solution of 2-((4-amino-1H-pyrazolo[3,4-d]pyrimidin-3-yl)oxy)ethan-1-ol (3) (5 g, 25.6 mmol, 1 eq) in DMA (1 mL) was added K₂CO₃ (8.85 g, 64.0 mmol, 2.5 eq) and bromocyclobutane (6.92 g, 51.2 mmol, 4.84 mL, 2 eq). The mixture was stirred at 80° C. for 16 h, filtered and the filtrate was concentrated under reduced pressure. The residue was purified by silica gel chromatography (Petroleum ether/(Ethyl acetate/EtOH=3/1)=1/O 1/1) to afford 2-((4-amino-1-cyclobutyl-1H-pyrazolo[3,4-d]pyrimidin-3-yl)oxy)ethan-1-ol (4) (3 g, 12.0 mmol, 47% yield) as a yellow solid.

Step 4. Procedure for Preparation of 4-amino-1-cyclobutyl-1H-pyrazolo[3,4-d]pyrimidin-3-ol (5)

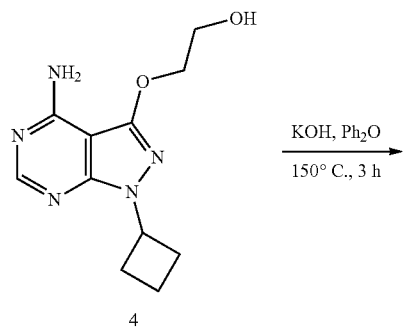

Two reactions were carried out in parallel. The mixture of 2-((4-amino-1-cyclobutyl-1H-pyrazolo[3,4-d]pyrimidin-3-yl)oxy)ethan-1-ol (4) (1 g, 4.01 mmol, 1 eq) and KOH (2.93 g, 52.2 mmol, 13 eq) in Ph₂O (10 mL) was stirred at 150° C. for 3 h. The reactions were combined for work up. Petroleum ether (15 mL) was added to the mixture, and the precipitate collected by filtration. The filter cake was collected, diluted with water and the pH was adjusted to between 5 and 6 using 1N HC. The mixture was filtered and the filter cake was dried under reduced pressure to afford 4-amino-1-cyclobutyl-1H-pyrazolo[3,4-d]pyrimidin-3-ol (5) (1.2 g, 5.85 mmol, 72.9% yield) as a light yellow solid. ¹H NMR: (400 MHz, DMSO-d₆) δ=8.02 (s, 1H), 5.11-5.02 (m, 1H), 2.58-2.53 (m, 2H), 2.26-2.24 (m, 2H), 1.78-1.71 (m, 2H).

Step 5. Procedure for Preparation of 3-((4-chloropyridin-2-yl)oxy)-1-cyclobutyl-1H-pyrazolo[3,4-d]pyrimidin-4-amine (6)

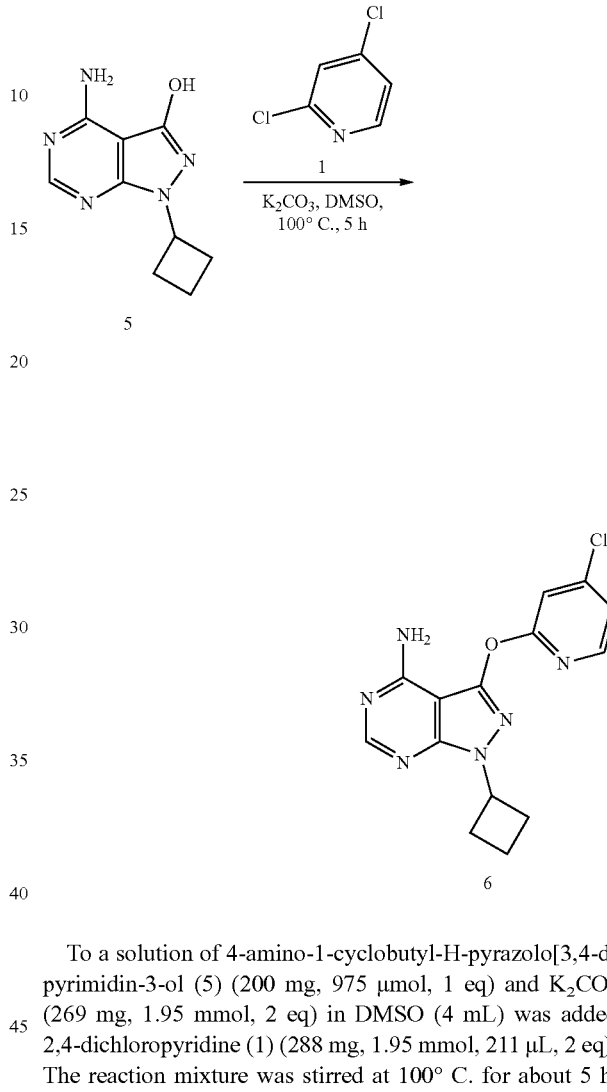

To a solution of 4-amino-1-cyclobutyl-H-pyrazolo[3,4-d]pyrimidin-3-ol (5) (200 mg, 975 μmol, 1 eq) and K₂CO₃ (269 mg, 1.95 mmol, 2 eq) in DMSO (4 mL) was added 2,4-dichloropyridine (1) (288 mg, 1.95 mmol, 211 μL, 2 eq). The reaction mixture was stirred at 100° C. for about 5 h, filtered, and the filtrate was collected, concentrated and purified by prep-HPLC (TFA condition) to afford 3-((4-chloropyridin-2-yl)oxy)-1-cyclobutyl-1H-pyrazolo[3,4-d]pyrimidin-4-amine (6; Compound 107) (51.7 mg, 120 μmol, 12.3% yield, 100% purity, TFA) as a white solid. LCMS: (M+H)⁺: 317.0, Rt: 2.62 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF₃CO₂H in water, mobile phase B was 0.018% CF₃CO₂H in CH₃CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS). ¹H NMR: (400 MHz, MeOD-d₄) δ=8.30 (s, 1H), 8.16 (d, J=5.2 Hz, 1H), 7.52 (s, 1H), 7.34 (d, J=5.6 Hz, 1H), 5.42-5.34 (m, 1H), 2.72-2.66 (m, 2H), 2.47-2.44 (m, 2H), 1.94-1.89 (m, 2H).

TABLE 7

| Compound No. | IUPAC Name | Expected MW (M) | LC/MS Observed (M + H) | 1H NMR (400 MHz) |
|---|---|---|---|---|
| 108 | 3-((4-chloro-5-fluoropyridin-2-yl)oxy)-1-cyclobutyl-1H-pyrazolo[3,4-d]pyrimidin-4-amine | 334 | 335 | (DMSO-d6) δ = 8.75 (s, 1H), 8.60 (d, J = 2.4 Hz, 1H), 8.36 (s, 1H), 8.21 (s, 1H), 7.58 (d, J = 6.0 Hz, 1H), 5.29-5.21 (m, 1H), 2.54-2.53 (m, 2H), 2.36-2.34 (m, 2H), 1.84-1.76 (m, 2H) |
| 109 | 1-cyclobutyl-3-((4-(trifluoromethyl)pyridin-2-yl)oxy)-1H-pyrazolo[3,4-d]pyrimidin-4-amine | 350.1 | 351.1 | (METHANOL-d4) δ = 8.42 (d, J = 5.2 Hz, 1H), 8.34 (s, 1H), 7.71 (s, 1H), 7.54 (d, J = 4.8 Hz, 1H), 5.44-5.35 (m, 1H), 2.70-2.65 (m, 2H), 2.47-2.44 (m, 2H), 1.93-1.88 (m, 2H) |
| 107 | 3-((4-chloropyridin-2-yl)oxy)-1-cyclobutyl-1H-pyrazolo[3,4-d]pyrimidin-4-amine | 316 | 317 | (METHANOL-d4) δ = 8.30 (s, 1H), 8.16 (d, J = 5.2 Hz, 1H), 7.52 (s, 1H), 7.34 (d, J = 5.6 Hz, 1H), 5.42-5.34 (m, 1H), 2.72-2.66 (m, 2H), 2.47-2.44 (m, 2H), 1.94-1.89 (m, 2H) |
| 111 | 2-((4-amino-1-cyclobutyl-1H-pyrazolo[3,4-d]pyrimidin-3-yl)oxy)isonicotinonitrile | 307.1 | 308.1 | (METHANOL-d4) δ = 8.38 (d, J = 4.8 Hz, 1H), 8.32 (s, 1H), 7.75 (s, 1H), 7.57 (d, J = 4.0 Hz, 1H), 5.43-5.35 (m, 1H), 2.70-2.65 (m, 2H), 2.46-2.42 (m, 2H), 1.94-1.89 (m, 2H) |
| 112 | 1-cyclobutyl-3-((4-methoxypyridin-2-yl)oxy)-1H-pyrazolo[3,4-d]pyrimidin-4-amine | 312.1 | 313.1 | (METHANOL-d4) δ = 8.31 (s, 1H), 8.04 (d, J = 6.0 Hz, 1H), 7.06 (d, J = 2.4 Hz, 1H), 6.90 (dd, J = 2.4, 6.0 Hz, 1H), 5.43-5.34 (m, 1H), 3.96 (s, 3H), 2.72-2.67 (m, 2H), 2.47-2.44 (m, 2H), 1.95-1.90 (m, 2H) |

79
Alternative Synthesis Method H: General Procedure Represented by the Preparation of (trans)-3-(4-amino-3-((4-(trifluoromethyl)pyridin-2-yl)oxy)-1H-pyrazolo[3,4-d]pyrimidin-1-yl)cyclobutan-1-ol
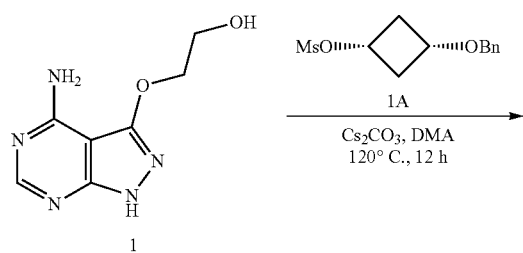
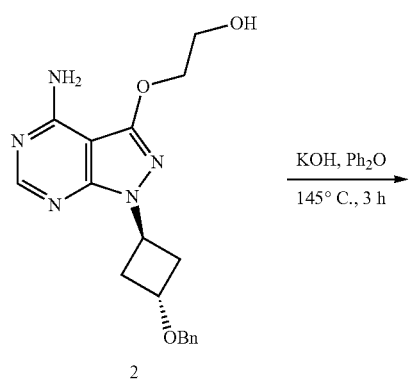
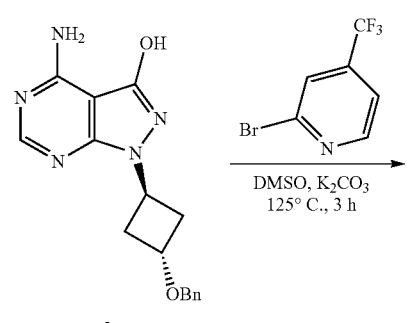
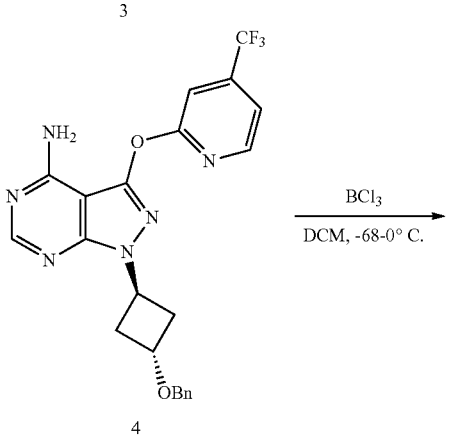
80
-continued
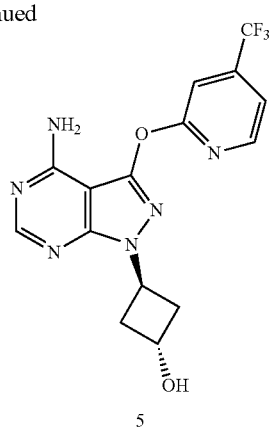
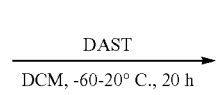
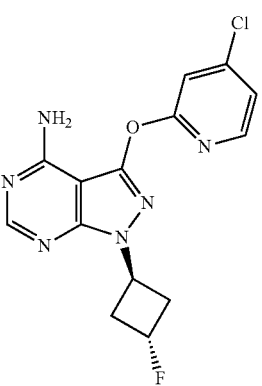
Step 1. Procedure for Preparation of 2-((4-amino-1-((trans)-3-(benzyloxy)cyclobutyl)-1H-pyrazolo[3,4-d]pyrimidin-3-yl)oxy)ethan-1-ol (2)
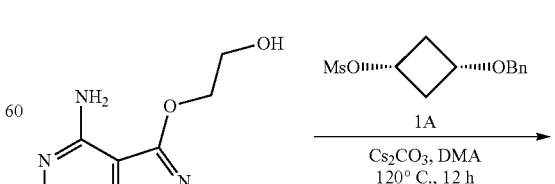

-continued

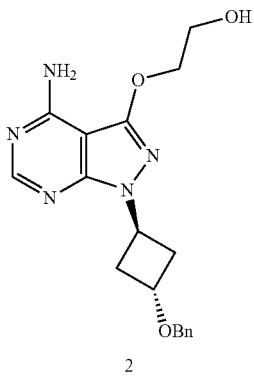

2

To a solution of 2-((4-amino-H-pyrazolo[3,4-d]pyrimidin-3-yl)oxy)ethan-1-ol (1) (5 g, 25.6 mmol, 1 eq) in DMA (250 mL) was added (cis)-3-(benzyloxy)cyclobutyl methanesulfonate (1A) (8.55 g, 33.3 mmol, 1.3 eq) and $Cs_2CO_3$ (25.1 g, 76.9 mmol, 3 eq) and then the mixture was stirred at 120° C. for about 12 h. The reaction mixture was filtered and the filtrate concentrated to provide crude product, which was purified by silica gel chromatography ($SiO_2$, Petroleum ether/Ethyl acetate=20/1 to 0/1) to give 2-((4-amino-1-((trans)-3-(benzyloxy)cyclobutyl)-1H-pyrazolo[3,4-d]pyrimidin-3-yl)oxy)ethan-1-ol (2) (3.2 g, 9.00 mmol, 35.1% yield) as a white solid.

Step 2. Procedure for Preparation of 4-amino-1-((1r,3r)-3-(benzyloxy)cyclobutyl)-1H-pyrazolo[3,4-d]pyrimidin-3-ol (3)

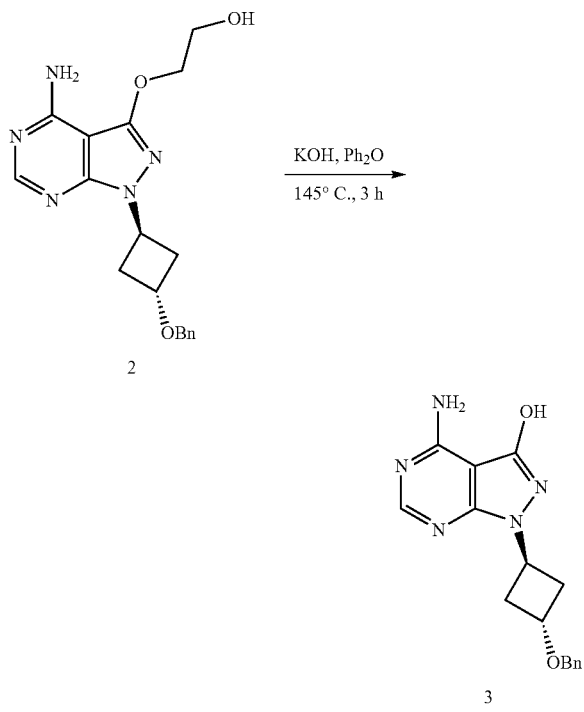

A mixture of 2-((4-amino-1-((trans)-3-(benzyloxy)cyclobutyl)-1H-pyrazolo[3,4-d]pyrimidin-3-yl)oxy)ethan-1-ol (2) (3.2 g, 9.00 mmol, 1 eq) and KOH (6.06 g, 108.06 mmol, 12 eq) in diphenyl ether (20 mL) was stirred at 145° C. for about 3 h. The reaction mixture was washed with petroleum ether (30 mL) and then the mixture was filtered. The filter cake was collected, dissolved in about 15 mL of water and the pH was adjusted to between 6 and 7 with hydrogen chloride. The precipitate was collected by filtration and the filter cake was dried under vacuum to give 4-amino-1-((trans)-3-(benzyloxy)cyclobutyl)-1H-pyrazolo[3,4-d]pyrimidin-3-ol (3) (2 g, 5.20 mmol, 57.8% yield) as a white solid. $^1$H NMR (400 MHz, METHANOL-d4) δ=8.10-8.03 (m, 1H), 7.40-7.24 (m, 5H), 4.53-4.39 (m, 3H), 3.77-3.62 (m, 1H), 2.75 (td, J=6.4, 13.2 Hz, 2H), 2.58-2.49 (m, 2H).

Step 3. Procedure for Preparation of 1-((trans)-3-(benzyloxy)cyclobutyl)-3-((4-(trifluoromethyl)pyridin-2-yl)oxy)-1H-pyrazolo[3,4-d]pyrimidin-4-amine (4)

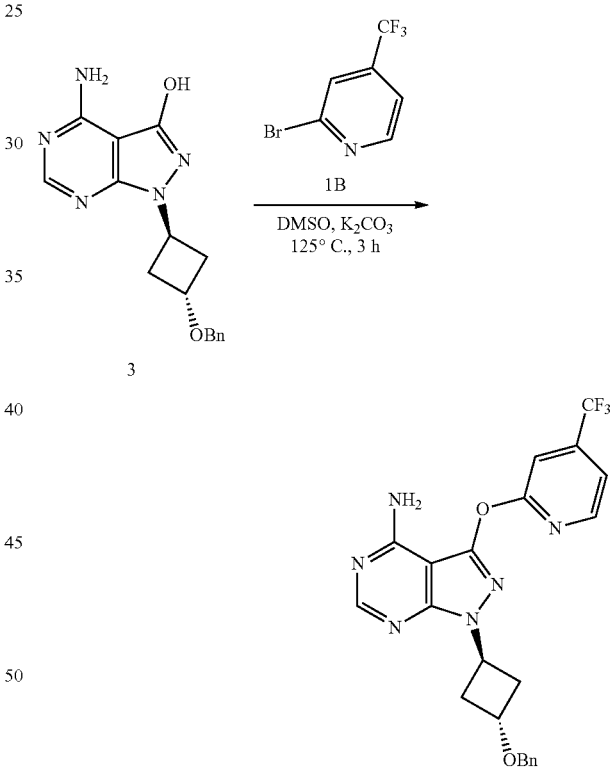

To a solution of 4-amino-1-((trans)-3-(benzyloxy)cyclobutyl)-1H-pyrazolo[3,4-d]pyrimidin-3-ol (3) (200 mg, 642 μmol, 1 eq) in DMSO (10 mL) was added 2-bromo-4-(trifluoromethyl)pyridine (1B) (233 mg, 1.28 mmol, 2 eq) and $K_2CO_3$ (178 mg, 1.28 mmol, 2 eq) and the mixture was stirred at 125° C. for about 3 h. The mixture was filtered and the filtrate was purified by prep-HPLC (TFA condition) to give 1-((trans)-3-(benzyloxy)cyclobutyl)-3-((4-(trifluoromethyl)pyridin-2-yl)oxy)-1H-pyrazolo[3,4-d]pyrimidin-4-amine (4) (150 mg, 263 μmol, 40.9% yield) as a white solid.

Step 4. Procedure for Preparation of (trans)-3-(4-amino-3-((4-(trifluoromethyl)pyridin-2-yl)oxy)-1H-pyrazolo[3,4-d]pyrimidin-1-yl)cyclobutan-1-ol (5)

Step 5. (Optional) Procedure for Preparation of 3-[(4-chloro-2-pyridyl)oxy]-1-(3-fluorocyclobutyl)pyrazolo[3,4-d]pyrimidin-4-amine (7)

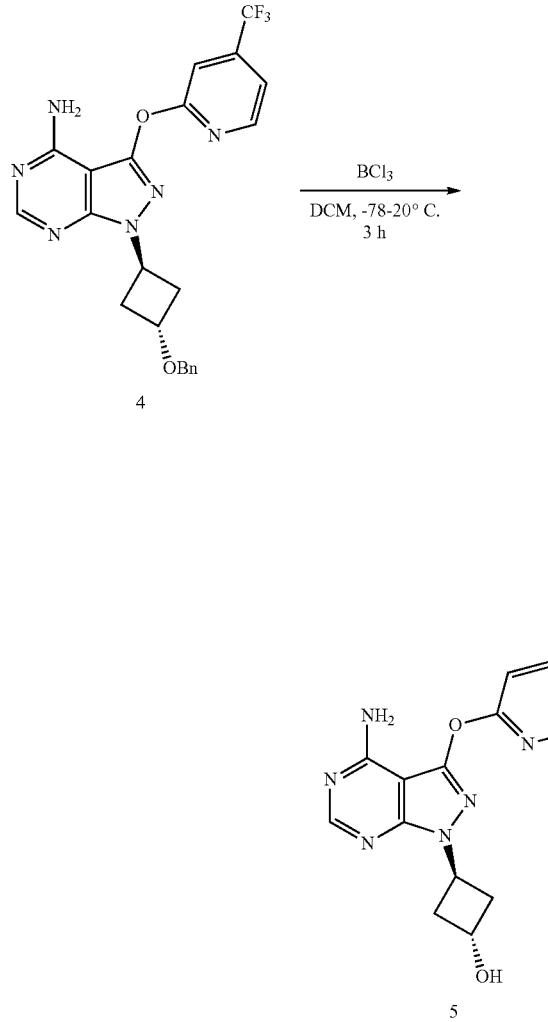

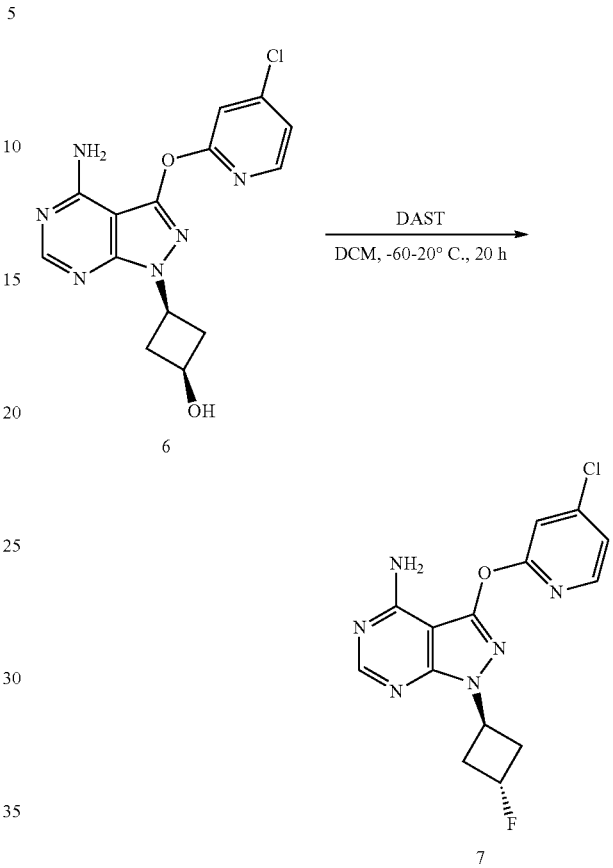

To a mixture of 1-((trans)-3-(benzyloxy)cyclobutyl)-3-((4-(trifluoromethyl)pyridin-2-yl)oxy)-1H-pyrazolo[3,4-d]pyrimidin-4-amine (4) (50 mg, 110 μmol, 1 eq) in DCM (2 mL) at −78° C. was added BCl₃ (1 M, 876 μL, 8 eq) dropwise. Once addition was complete the mixture was stirred at 20° C. for about 3 h. The reaction was quenched by adding methanol (10 mL) at −60° C. and then the pH was adjusted to 7 using NH₃.H₂O at 0° C. The mixture was filtered and the filtrate was concentrated under reduced pressure to give a residue, which was purified by prep-HPLC (TFA condition) to give (trans)-3-(4-amino-3-((4-(trifluoromethyl)pyridin-2-yl)oxy)-1H-pyrazolo[3,4-d]pyrimidin-1-yl)cyclobutan-1-ol (5; Compound 113) (30 mg, 55% yield, 96.6% purity, TFA) as a white solid. LCMS: (M+H)⁺: 367.0, Rt: 2.344 min. ¹H NMR: (400 MHz, METHANOL-d₄) δ=8.42 (d, J=5.2 Hz, 1H), 8.30 (s, 1H), 7.73 (s, 1H), 7.55 (d, J=5.2 Hz, 1H), 5.58-5.50 (m, 1H), 4.63-4.56 (m, 1H), 2.85-2.77 (m, 2H), 2.54-2.50 (m, 2H).

To convert the hydroxycycloalkyl to the fluoroalkyl, DAST may be used as follows. To the mixture of 3-[4-amino-3-[(4-chloro-2-pyridyl)oxy]pyrazolo[3,4-d]pyrimidin-1-yl]cyclobutanol (6) (150 mg, 335.75 umol, 1 eq, TFA) in DCM (5 mL) was added DAST (270.59 mg, 1.68 mmol, 221.80 uL, 5 eq) at −60° C. under nitrogen atmosphere. Then the mixture warmed to 20° C. slowly and stirred for 20 hrs. LCMS showed the reaction was completed. The mixture was poured into 7 mL of water, extracted with dichloromethane (3×10 mL). The combined organic layer was dried over anhydrous sodium sulfate and then concentrated to give the residue. The residue was purified by prep-HPLC (neutral condition) to afford 3-[(4-chloro-2-pyridyl)oxy]-1-(3-fluorocyclobutyl)pyrazolo[3,4-d]pyrimidin-4-amine (7) (60.6 mg, 177.42 umol, 52.84% yield, 98% purity) was obtained as a white solid. LCMS: (M+H)⁺: 335.0, Rt: 2.582 min.

LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF₃CO₂H in water, mobile phase B was 0.018% CF₃CO₂H in CH₃CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).).

¹H NMR: (400 MHz, DMSO-d6) δ=8.19 (s, 1H), 8.12 (d, J=5.6 Hz, 1H), 7.41 (d, J=1.6 Hz, 1H), 7.34 (dd, J=1.6, 5.6 Hz, 1H), 5.50-5.45 (m, 1.5H), 5.35-5.31 (m, 0.5H), 2.82-2.67 (m, 4H)

TABLE 8a

Compounds Prepared by Alternative Method H

| Compound No. | IUPAC Name | Expected MW (M) | LC/MS Observed (M + H) | 1H NMR (400 MHz) |
|---|---|---|---|---|
| 113 | (trans)-3-(4-amino-3-((4-(trifluoromethyl)pyridin-2-yl)oxy)-1H-pyrazolo[3,4-d]pyrimidin-1-yl)cyclobutan-1-ol | 366.1 | 367 | (METHANOL-d4) δ = 8.42 (d, J = 5.2 Hz, 1H), 8.30 (s, 1H), 7.73 (s, 1H), 7.55 (d, J = 5.2 Hz, 1H), 5.58-5.50 (m, 1H), 4.63-4.56 (m, 1H), 2.85-2.77 (m, 2H), 2.51 (ddd, J = 4.0, 8.8, 13.6 Hz, 2H) |
| 115 | 2-((4-amino-1-((trans)-3-hydroxycyclobutyl)-1H-pyrazolo[3,4-d]pyrimidin-3-yl)oxy)isonicotinonitrile | 323.2 | 324.2 | (METHANOL-d4) δ = 8.38 (dd, J = 0.8, 5.2 Hz, 1H), 8.30 (s, 1H), 7.77-7.74 (m, 1H), 7.57 (dd, J = 1.2, 5.2 Hz, 1H), 5.59-5.52 (m, 1H), 4.63-4.54 (m, 1H), 2.87-2.76 (m, 2H), 2.51 (ddd, J = 4.4, 8.8, 13.2 Hz, 2H) |
| 116 | (trans)-3-(4-amino-3-((4-chloropyridin-2-yl)oxy)-1H-pyrazolo[3,4-d]pyrimidin-1-yl)cyclobutan-1-ol | 332 | 333 | (METHANOL-d4) δ = 8.29 (s, 1H), 8.16 (d, J = 5.6 Hz, 1H), 7.53 (d, J = 1.6 Hz, 1H), 7.34 (dd, J = 1.6, 5.6 Hz, 1H), 5.57-5.50 (m, 1H), 4.64-4.57 (m, 1H), 2.83-2.78 (m, 2H), 2.55-2.50 (m, 2H) |
| 117 | (trans)-3-(4-amino-3-((2-chloropyridin-4-yl)oxy)-1H-pyrazolo[3,4-d]pyrimidin-1-yl)cyclobutan-1-ol | 332 | 333 | (METHANOL-d4) δ = 8.40 (d, J = 5.6 Hz, 1H), 8.30 (s, 1H), 7.64 (d, J = 2.0 Hz, 1H), 7.52 (dd, J = 2.4, 5.6 Hz, 1H), 5.53 (tt, J = 5.6, 8.4 Hz, 1H), 4.66-4.60 (m, 1H), 2.84-2.77 (m, 2H), 2.53 (ddd, J = 4.4, 8.8, 13.6 Hz, 2H) |
| 118 | (trans)-3-(4-amino-3-((4-methoxypyridin-2-yl)oxy)-1H-pyrazolo[3,4-d]pyrimidin-1-yl)cyclobutan-1-ol | 328.1 | 329.1 | (METHANOL-d4) δ = 8.29 (s, 1H), 8.04 (d, J = 6.0 Hz, 1H), 7.07 (d, J = 2.4 Hz, 1H), 6.89 (dd, J = 2.4, 5.6 Hz, 1H), 5.56-5.48 (m, 1H), 4.65-4.59 (m, 1H), 3.96 (s, 3H), 2.86-2.79 (m, 2H), 2.55-2.50 (m, 2H) |

TABLE 8b

Compounds Prepared by Alternative Method H, using (trans)-3-(benzyloxy) cyclobutyl methanesulfonate as the step 1 starting material to generate the (cis)-3-cyclobutyl alcohols

| Compound No. | IUPAC Name | Expected MW (M) | LC/MS Observed (M + H) | 1H NMR (400 MHz) |
|---|---|---|---|---|
| 119 | 2-((4-amino-1-((cis)-3-hydroxycyclobutyl)-1H-pyrazolo[3,4-d]pyrimidin-3-yl)oxy)isonicotinonitrile | 323.1 | 324.1 | (METHANOL-d4) δ = 8.40-8.38 (m, 1H), 8.31 (s, 1H), 7.80 (s, 1H), 7.60 (dd, J = 1.2, 5.2 Hz, 1H), 4.98-4.88 (m, 1H), 4.18-4.11 (m, 1H), 2.83-2.79 (m, 2H), 2.62-2.55 (m, 2H) |
| 120 | 2-((4-amino-1-((cis)-3-hydroxycyclobutyl)-1H-pyrazolo[3,4-d]pyrimidin-3-yl)oxy)isonicotinamide | 341.1 | 342.1 | (METHANOL-d4) δ = 8.34 (d, J = 5.2 Hz, 1H), 8.30 (s, 1H), 7.80 (s, 1H), 7.66 (d, J = 4.8 Hz, 1H), 4.97-4.95 (m, 1H), 4.14 (q, J = 7.2 Hz, 1H), 2.83-2.79 (m, 2H), 2.62-2.55 (m, 2H) |

Synthesis Method I: General Procedure Represented by the Preparation of 3-(3-chlorophenoxy)-1-cyclobutyl-1H-pyrazolo[3,4-d]pyrimidin-4-amine

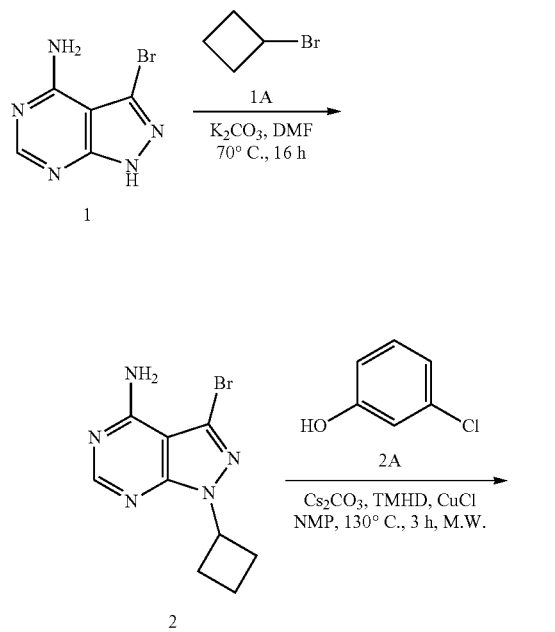

Step 1

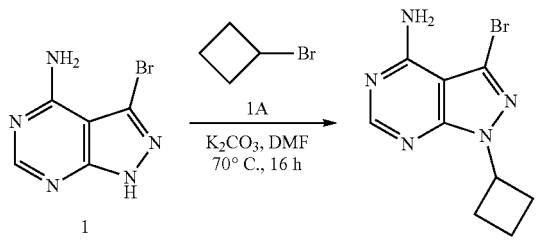

A mixture of 3-bromo-1H-pyrazolo[3,4-d]pyrimidin-4-amine (1) (4 g, 18.7 mmol, 1 eq), bromocyclobutane (1A) (5.05 g, 37.4 mmol, 3.53 mL, 2 eq) and $K_2CO_3$ (5.17 g, 37.4 mmol, 2 eq) in DMF (10 mL) was stirred at 70° C. for 16 h. The mixture was added into 100 mL $H_2O$, filtered and the collected solid was dried under reduced pressure to afford 3-bromo-1-cyclobutyl-1H-pyrazolo[3,4-d]pyrimidin-4-amine (2) (3.6 g, 13.4 mmol, 72% yield) as a yellow solid. $^1$H NMR: (400 MHz, DMSO-$d_6$) δ=8.15 (s, 1H), 7.38 (s, 2H), 5.19 (s, 1H), 2.46 (s, 2H), 2.31 (s, 2H), 1.78 (s, 2H).

Step 2

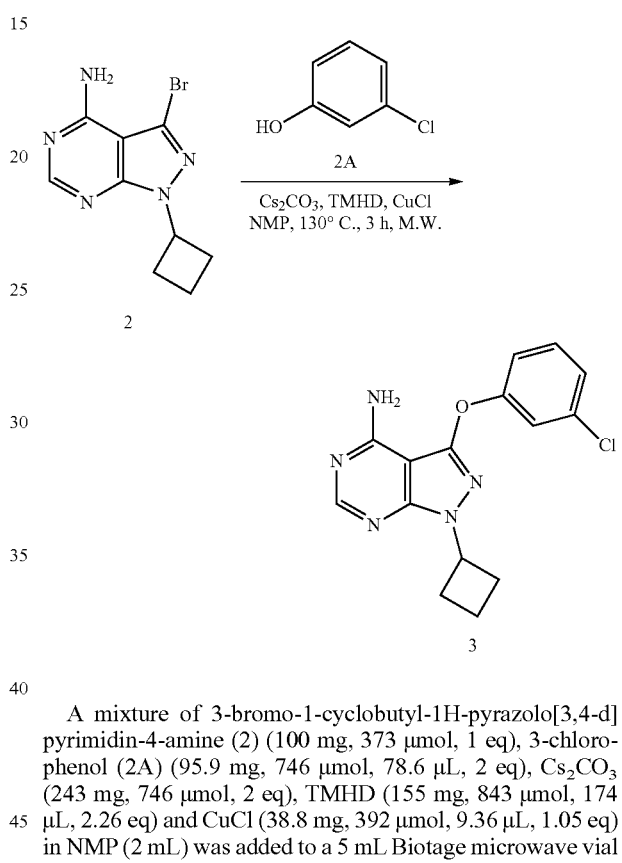

A mixture of 3-bromo-1-cyclobutyl-1H-pyrazolo[3,4-d]pyrimidin-4-amine (2) (100 mg, 373 μmol, 1 eq), 3-chlorophenol (2A) (95.9 mg, 746 μmol, 78.6 μL, 2 eq), $Cs_2CO_3$ (243 mg, 746 μmol, 2 eq), TMHD (155 mg, 843 μmol, 174 μL, 2.26 eq) and CuCl (38.8 mg, 392 μmol, 9.36 μL, 1.05 eq) in NMP (2 mL) was added to a 5 mL Biotage microwave vial with a Teflon coated stirring bar under nitrogen atmosphere. The vial was sealed and heated at 130° C. for 3 h in a microwave reactor. The mixture was filtered and the filtrate was concentrated under reduced pressure. The resulting residue was purified by prep-HPLC (TFA condition) to afford 3-(3-chlorophenoxy)-1-cyclobutyl-1H-pyrazolo[3,4-d]pyrimidin-4-amine (3; Compound 121) (14.6 mg, 34.0 μmol, 9.1% yield) as a white solid. LCMS: (M+H)$^+$: 316.0, Rt: 2.586 min. LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS). $^1$H NMR: (400 MHz, MeOD-$d_4$) δ=8.28 (s, 1H), 7.52 (s, 1H), 7.47-7.40 (m, 2H), 7.29 (d, J=8.0 Hz, 1H), 5.36-5.27 (m, 1H), 2.67-2.62 (m, 2H), 2.41 (s, 2H), 1.93-1.86 (m, 2H).

TABLE 9

Compounds Prepared by Method I

| Compound No. | IUPAC Name | Expected MW (M) | LC/MS Observed (M + H) | 1H NMR (400 MHz) |
|---|---|---|---|---|
| 121 | 3-(3-chlorophenoxy)-1-cyclobutyl-1H-pyrazolo[3,4-d]pyrimidin-4-amine | 315.09 | 316 | (METHANOL-d4) δ = 8.28 (s, 1H), 7.52 (s, 1H), 7.47-7.40 (m, 2H), 7.29 (d, J = 8.0 Hz, 1H), 5.36-5.27 (m, 1H), 2.67-2.62 (m, 2H), 2.41 (s, 2H), 1.93-1.86 (m, 2H) |
| 123 | 1-cyclobutyl-3-((5-methoxypyridin-3-yl)oxy)-1H-pyrazolo[3,4-d]pyrimidin-4-amine | 312.13 | 313.1 | (METHANOL-d4) δ = 8.35 (s, 1H), 8.21 (s, 1H), 8.16 (s, 1H), 7.63 (t, J = 2.0 Hz, 1H), 5.27 (q, J = 8.4 Hz, 1H), 3.92 (s, 3H), 2.70-2.57 (m, 2H), 2.46-2.35 (m, 2H), 1.92-1.82 (m, 2H) |

Synthesis Method J: General Procedure Represented by the Preparation of (trans)-3-(4-Amino-3-(3-chlorobenzyl)-1H-pyrazolo[3,4-d]pyrimidin-1-yl)cyclobutan-1-ol

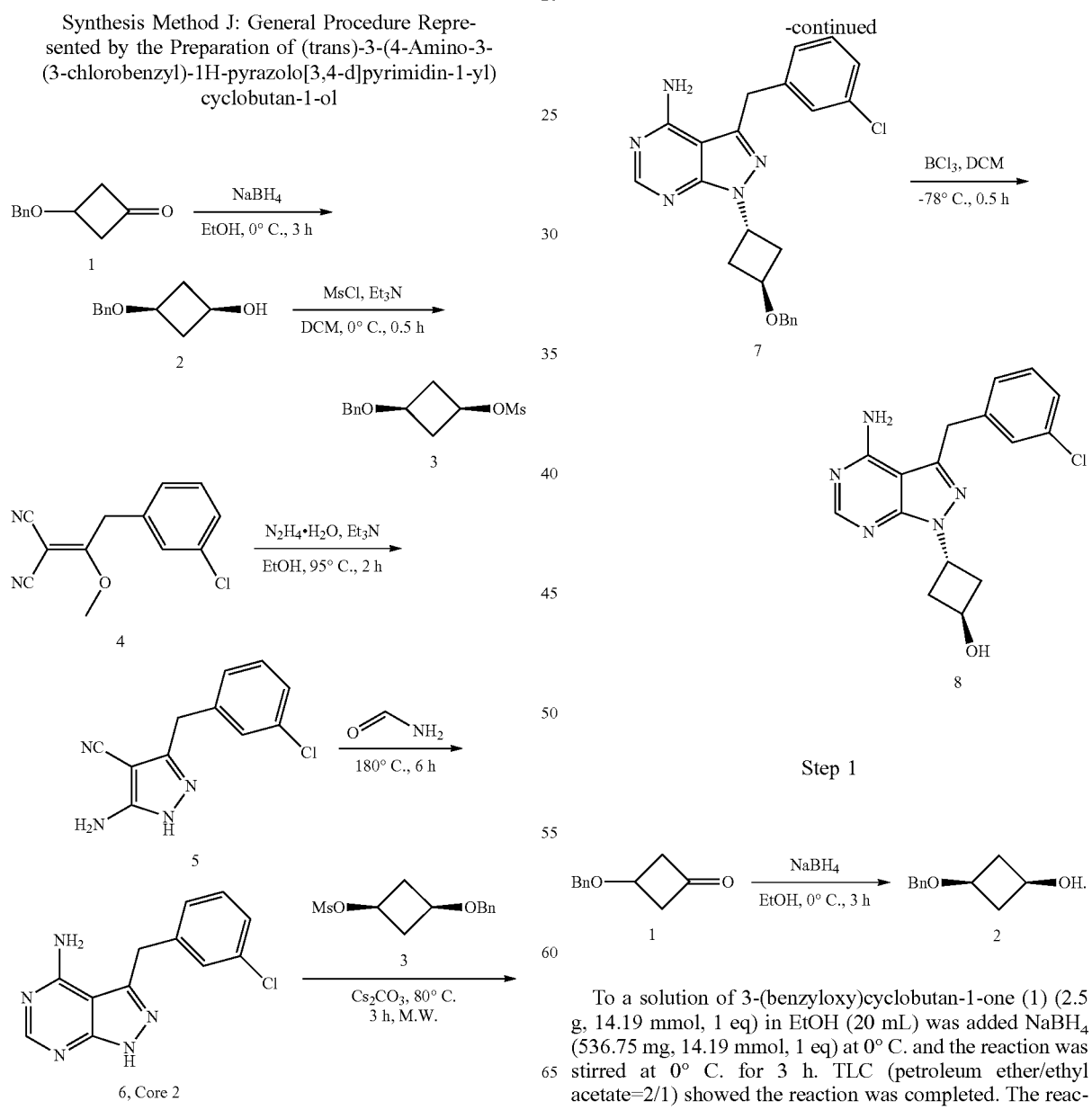

Step 1

To a solution of 3-(benzyloxy)cyclobutan-1-one (1) (2.5 g, 14.19 mmol, 1 eq) in EtOH (20 mL) was added NaBH$_4$ (536.75 mg, 14.19 mmol, 1 eq) at 0° C. and the reaction was stirred at 0° C. for 3 h. TLC (petroleum ether/ethyl acetate=2/1) showed the reaction was completed. The reaction was quenched by the addition of water (50 mL). The resulting mixture was extracted with Ethyl acetate (50 mL×3). The organic phase was dried over Na₂SO₄, filtered and concentrated under reduced pressure to give (cis)-3-(benzyloxy)cyclobutan-1-ol (2) (2.5 g, crude) as yellow oil.

Step 2

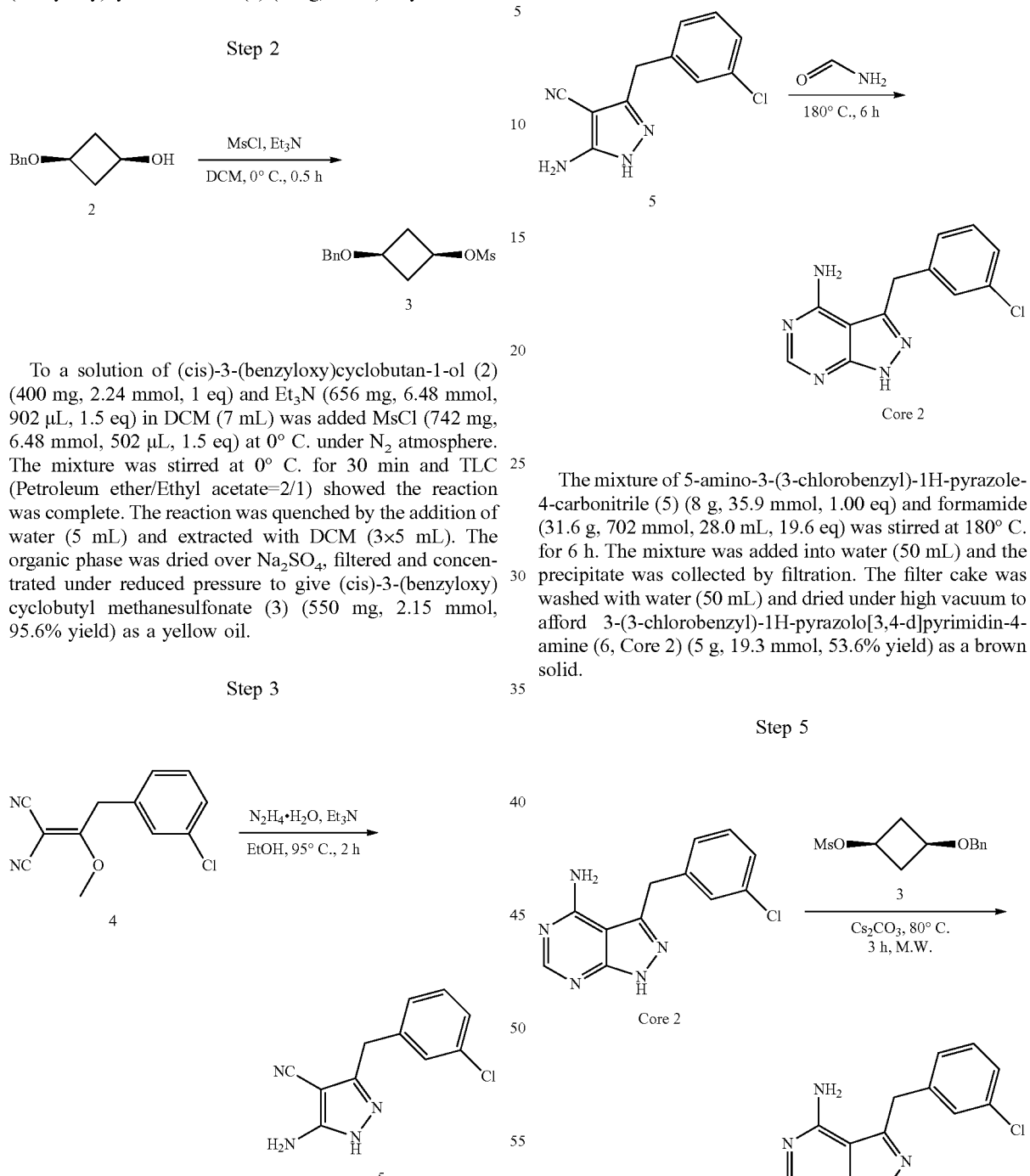

To a solution of (cis)-3-(benzyloxy)cyclobutan-1-ol (2) (400 mg, 2.24 mmol, 1 eq) and Et₃N (656 mg, 6.48 mmol, 902 μL, 1.5 eq) in DCM (7 mL) was added MsCl (742 mg, 6.48 mmol, 502 μL, 1.5 eq) at 0° C. under N₂ atmosphere. The mixture was stirred at 0° C. for 30 min and TLC (Petroleum ether/Ethyl acetate=2/1) showed the reaction was complete. The reaction was quenched by the addition of water (5 mL) and extracted with DCM (3×5 mL). The organic phase was dried over Na₂SO₄, filtered and concentrated under reduced pressure to give (cis)-3-(benzyloxy) cyclobutyl methanesulfonate (3) (550 mg, 2.15 mmol, 95.6% yield) as a yellow oil.

Step 3

A mixture of 2-(2-(3-chlorophenyl)-1-methoxyethylidene)malononitrile (4) (7.53 g, 32.4 mmol, 1.00 eq), Et₃N (13.1 g, 130 mmol, 18.03 mL, 4.00 eq) and N₂H₄·H₂O (1.78 g, 35.6 mmol, 1.73 mL, 1.1 eq) in EtOH (70 mL) was stirred at 95° C. for 2 h. The mixture was concentrated under reduced pressure to give 5-amino-3-(3-chlorobenzyl)-1H-pyrazole-4-carbonitrile (5) (8 g, crude) as a brown solid which was used to the next step without further purification.

Step 4

The mixture of 5-amino-3-(3-chlorobenzyl)-1H-pyrazole-4-carbonitrile (5) (8 g, 35.9 mmol, 1.00 eq) and formamide (31.6 g, 702 mmol, 28.0 mL, 19.6 eq) was stirred at 180° C. for 6 h. The mixture was added into water (50 mL) and the precipitate was collected by filtration. The filter cake was washed with water (50 mL) and dried under high vacuum to afford 3-(3-chlorobenzyl)-1H-pyrazolo[3,4-d]pyrimidin-4-amine (6, Core 2) (5 g, 19.3 mmol, 53.6% yield) as a brown solid.

Step 5

The mixture of 3-(3-chlorobenzyl)-1H-pyrazolo[3,4-d]pyrimidin-4-amine (7, Core_2) (500 mg, 1.93 mmol, 1 eq), (cis)-3-(benzyloxy)cyclobutyl methanesulfonate (3) (543 mg, 2.12 mmol, 1.1 eq) and $Cs_2CO_3$ (1.25 g, 3.85 mmol, 2 eq) in DMF (2 mL) was stirred at 80° C. for 3 h in a microwave reactor. The mixture was filtered and the filtrate was concentrated under reduced pressure. The resulting residue was purified by prep-HPLC (neutral condition) to give 1-((trans)-3-(benzyloxy)cyclobutyl)-3-(3-chlorobenzyl)-1H-pyrazolo[3,4-d]pyrimidin-4-amine (7) (200 mg, 428.67 μmol, 22.26% yield, 90% purity) as a white solid.

Step 6

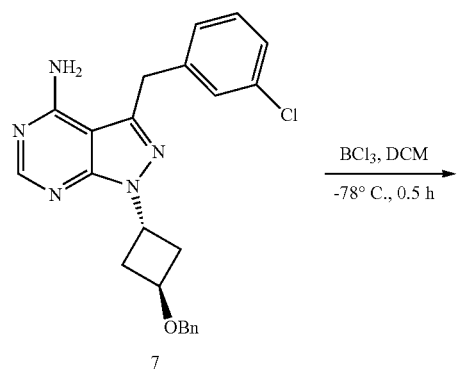

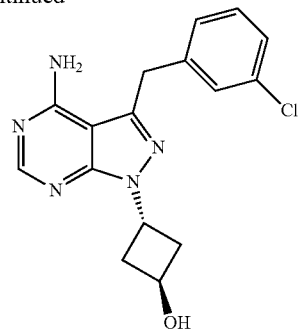

To a solution of 1-((trans)-3-(benzyloxy)cyclobutyl)-3-(3-chlorobenzyl)-1H-pyrazolo[3,4-d]pyrimidin-4-amine (7) (100 mg, 238 μmol, 1 eq) in DCM (8 mL) was added trichloroborane (1 M, 1.43 mL, 6 eq) drop-wise at −78° C. under $N_2$ atmosphere. The mixture was stirred at −78° C. for 30 min and quenched with MeOH (4 mL) at −78° C. The pH was adjusted to 7 by addition of $NH_3.H_2O$ at 0° C. The mixture was filtered and the filtrate concentrated under reduced pressure to give a residue. The residue was purified by prep-HPLC (neutral condition) to give (trans)-3-(4-amino-3-(3-chlorobenzyl)-1H-pyrazolo[3,4-d]pyrimidin-1-yl)cyclobutan-1-ol (8; Compound 124) 20 mg, 60.2 μmol, 25.3% yield, 99.2% purity) as a white solid. LC/MS $(M+H)^+$: 330.0, Rt: 2.330 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS). $^1H$ NMR: (400 MHz, METHANOL-$d_4$) δ=8.13 (s, 1H), 7.29-7.23 (m, 3H), 7.17-7.15 (m, 1H), 5.49-5.41 (m, 1H), 4.71-4.65 (m, 1H), 4.38 (s, 2H), 2.90-2.84 (m, 2H), 2.54-2.48 (m, 2H).

TABLE 10

Compounds Prepared by Method J

| Compound No. | IUPAC Name | Expected MW (M) | LC/MS Observed (M + H) | 1H NMR (400 MHz) |
|---|---|---|---|---|
| 124 | (trans)-3-(4-amino-3-(3-chlorobenzyl)-1H-pyrazolo[3,4-d]pyrimidin-1-yl)cyclobutan-1-ol | 329.1 | 330 | (METHANOL-d4) δ = 8.13 (s, 1H), 7.29-7.23 (m, 3H), 7.17-7.15 (m, 1H), 5.49-5.41 (m, 1H), 4.71-4.65 (m, 1H), 4.38 (s, 2H), 2.90-2.84 (m, 2H), 2.54-2.48 (m, 2H) |
| 125 | (trans)-3-(4-amino-3-(3-(trifluoromethyl)benzyl)-1H-pyrazolo[3,4-d]pyrimidin-1-yl)cyclobutan-1-ol | 363.1 | 364.1 | (METHANOL-d4) δ = 8.27 (s, 1H), 7.65 (s, 1H), 7.56-7.48 (m, 3H), 5.56-5.49 (m, 1H), 4.69-4.63 (m, 1H), 4.54 (s, 2H), 2.85-2.81 (m, 2H), 2.55-2.51 (m, 2H) |
| 126 | 3-((4-amino-1-((trans)-3-hydroxycyclobutyl)-1H-pyrazolo[3,4-d]pyrimidin-3-yl)methyl)benzonitrile | 320.1 | 321.1 | (METHANOL-d4) δ = 8.14 (s, 1H), 7.65 (s, 1H), 7.59 (d, J = 7.6 Hz, 1H), 7.57-7.52 (m, 1H), 7.51-7.45 (m, 1H), 5.52-5.40 (m, |

TABLE 10-continued

Compounds Prepared by Method J

| Compound No. | IUPAC Name | Expected MW (M) | LC/MS Observed (M + H) | 1H NMR (400 MHz) |
|---|---|---|---|---|
| | | | | 1H), 4.72-4.63 (m, 1H), 4.46 (s, 2H), 2.92-2.81 (m, 2H), 2.54-2.48 (m, 2H) |
| 127 | (trans)-3-(4-amino-3-(3-bromobenzyl)-1H-pyrazolo[3,4-d]pyrimidin-1-yl)cyclobutan-1-ol | 376.0/375.0 | 374.0/376.0 | (METHANOL-d4) δ = 8.29 (s, 1H), 7.48 (s, 1H), 7.43-7.37 (m, 1H), 7.24 (d, J = 4.8 Hz, 2H), 5.55 (tt, J = 5.6, 8.4 Hz, 1H), 4.71-4.66 (m, 1H), 4.45 (s, 2H), 2.88-2.82 (m, 2H), 2.57-2.50 (m, 2H) |
| 128 | (trans)-3-(4-amino-3-(3-fluorobenzyl)-1H-pyrazolo[3,4-d]pyrimidin-1-yl)cyclobutan-1-ol | 313.13 | 314.2 | (CDCl$_3$) δ = 8.14 (s, 1H), 7.43-7.37 (m, 1H), 7.09-7.04 (m, 2H), 6.88 (d, J = 9.2 Hz, 1H), 5.66-5.59 (m, 1H), 4.92-4.86 (m, 1H), 4.36 (s, 2H), 3.04-2.97 (m, 2H), 2.67-2.62 (m, 2H) |
| 129 | 3-((4-amino-1-((trans)-3-hydroxycyclobutyl)-1H-pyrazolo[3,4-d]pyrimidin-3-yl)methyl)benzamide | 338.1 | 339.1 | (METHANOL-d4) δ = 8.27 (s, 1H), 7.76-7.73 (m, 2H), 7.47-7.40 (m, 2H), 5.60-5.50 (m, 1H), 4.72-4.66 (m, 1H), 4.52 (s, 2H), 2.89-2.86 (m, 2H), 2.58-2.50 (m, 2H) |

Synthesis Method K: General Procedure Represented by the Preparation of (cis)-3-(4-amino-3-(3-chlorobenzyl)-1H-pyrazolo[3,4-d]pyrimidin-1-yl)cyclobutan-1-ol

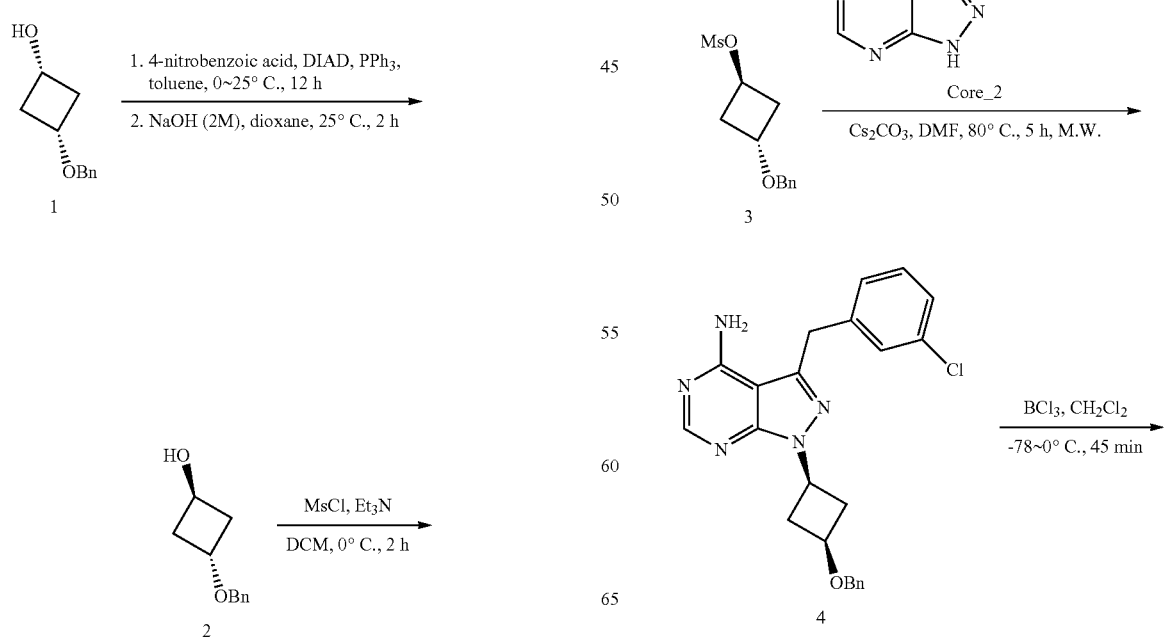

-continued

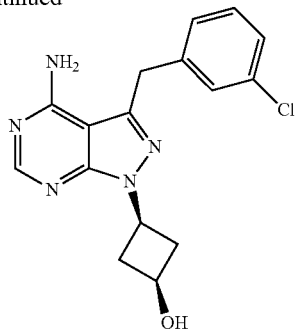

TRC-002927-NX-1

Step 1

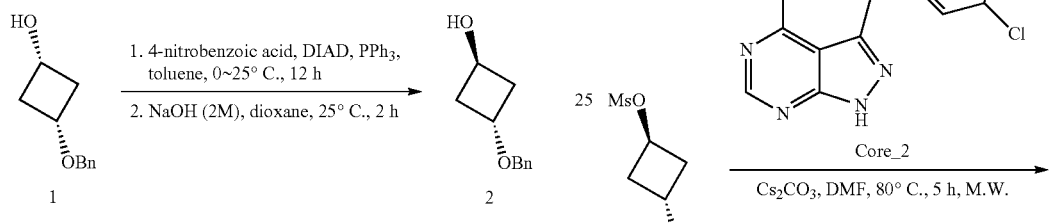

To a solution of (cis)-3-(benzyloxy)cyclobutan-1-ol (1) (1 g, 5.61 mmol, 1 eq), 4-nitrobenzoic acid (938 mg, 5.61 mmol, 1 eq) and PPh$_3$ (1.47 g, 5.61 mmol, 1 eq) in toluene (20 mL) at 0° C. was added DIAD (1.13 g, 5.61 mmol, 1.09 mL, 1 eq). The reaction was then stirred at 25° C. for 12 h, quenched with H$_2$O (50 mL), extracted with ethyl acetate (2×50 mL), dried (Na$_2$SO$_4$), filtered and concentrated under reduced pressure. The residue was purified by column chromatography (petroleum ether/ethyl acetate=5/1) to give the intermediate (1.7 g). The intermediate was dissolved in dioxane (8 mL) and NaOH (2 M, 2.81 mL, 1 eq), stirred at 25° C. for 2 h, quenched with H$_2$O (5 mL) and extracted with ethyl acetate (2×5 mL). The combined organic layers were dried (Na$_2$SO$_4$), filtered and concentrated under reduced pressure. The residue was purified by column chromatography (SiO$_2$, petroleum ether/ethyl acetate=3/1) to give (trans)-3-(benzyloxy)cyclobutan-1-ol (2) (0.6 g, 3.37 mmol, 60% yield) as colorless oil. $^1$H NMR: (400 MHz, CDCl$_3$) δ7.38-7.27 (m, 5H), 4.56 (tt, J=4.4, 6.8 Hz, 1H), 4.42 (s, 2H), 4.29 (tt, J=4.4, 6.8 Hz, 1H), 2.42-2.33 (m, 2H), 2.24-2.15 (m, 2H).

Step 2

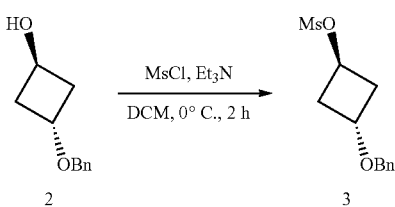

To a solution of (trans)-3-(benzyloxy)cyclobutan-1-ol (2) (1.0 g, 5.61 mmol, 1 eq) and Et$_3$N (1.14 g, 11.2 mmol, 1.56 mL, 2 eq) in dichloromethane (10 mL) was added MsCl (964 mg, 8.42 mmol, 651 μL, 1.5 eq) at 0° C. under nitrogen atmosphere. Then the mixture was stirred at 0° C. for about 2 h. The reaction mixture was poured into H$_2$O (10 mL) slowly, and then extracted with dichloromethane (3×10 mL). The combined organic layers were dried over Na$_2$SO$_4$, filtered and concentrated under reduced pressure to give (trans)-3-(benzyloxy)cyclobutyl methanesulfonate (3) (1.21 g, crude) as a yellow oil which was used to the next step directly.

Step 3

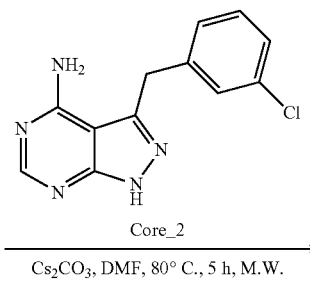

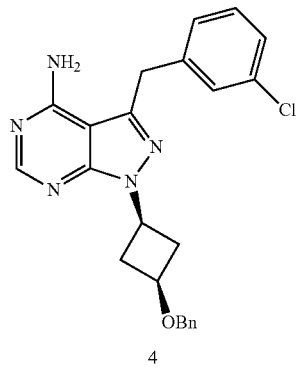

A mixture of (trans)-3-(benzyloxy)cyclobutyl methanesulfonate (3) (1.21 g, crude), 3-(3-chlorobenzyl)-1H-pyrazolo-[3,4-d]pyrimidin-4-amine (1 g, 3.85 mmol, 1 eq), Cs$_2$CO$_3$ (2.51 g, 7.70 mmol, 2 eq) and N,N-dimethylformamide (10 mL) was heated at 80° C. for 3 h under microwave irradiation. The mixture was filtered and the filtrate concentrated under reduced pressure. The resulting residue was purified by prep-HPLC (neutral condition) to give 1-((cis)-3-(benzyloxy)cyclobutyl)-3-(3-chlorobenzyl)-1H-pyrazolo-[3,4-d]-pyrimidin-4-amine (4) (1.5 g, 3.22 mmol, 42% yield, 90% purity) as a yellow solid. $^1$H NMR: (400 MHz, CDCl$_3$) δ=8.27 (s, 1H), 7.41-7.36 (m, 7H), 7.30-7.27 (m, 1H), 7.22-7.12 (m, 1H), 5.07 (s, 2H), 5.00-4.92 (m, 1H), 4.54 (s, 2H), 4.32 (s, 2H), 4.06-3.98 (m, 1H), 2.88-2.84 (m, 4H).

Step 4

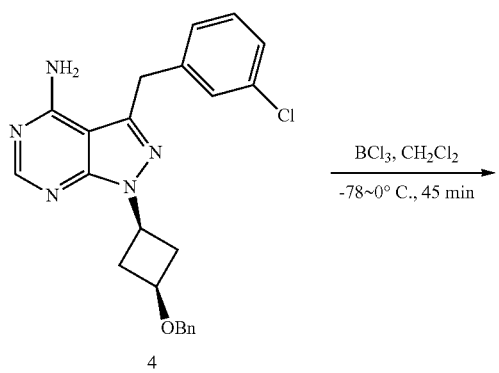

To a solution of 1-((cis)-3-(benzyloxy)cyclobutyl)-3-(3-chlorobenzyl)-1H-pyrazolo-[3,4-d]-pyrimidin-4-amine (4) (35 mg, 83 μmol, 1 eq) in dichloromethane (5 mL) was added $BCl_3$ (1 M, 834 μL, 10 eq) at −78° C. under nitrogen atmosphere. The mixture was warmed to 0° C. for 45 min and quenched with MeOH (5 mL) at −78° C., warmed to 0° C. and the pH adjusted to 7 using 33% $NH_3.H_2O$. The mixture was filtered and the filtrate was concentrated under reduced pressure to give a residue that was purified by prep-HPLC (neutral condition) to give (cis)-3-(4-amino-3-(3-chlorobenzyl)-1H-pyrazolo[3,4-d]pyrimidin-1-yl)cyclobutan-1-ol (Compound 130)(3.7 mg, 11.1 μmol, 6.67% yield, 99% purity) as a white solid. LCMS: $(M+H)^+$: 330.1, Rt: 2.253 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% $CF_3CO_2H$ in water, mobile phase was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS). $^1$H NMR: (400 MHz, MeOD-d$_4$) δ 8.15 (s, 1H), 7.31-7.25 (m, 2H), 7.25-7.20 (m, 1H), 7.17 (d, J=7.6 Hz, 1H), 4.85-4.79 (m, 1H), 4.39 (s, 2H), 4.23-4.12 (m, 1H), 2.85-2.82 (m, 2H), 2.70-2.67 (m, 2H).

TABLE 11

Compounds Prepared by Method K

| Compound No. | IUPAC Name | Expected MW (M) | LC/MS Observed (M + H) | 1H NMR (400 MHz) |
|---|---|---|---|---|
| 130 | (cis)-3-(4-amino-3-(3-chlorobenzyl)-1H-pyrazolo[3,4-d]pyrimidin-1-yl)cyclobutan-1-ol | 329.1 | 330.1 | (METHANOL-d4) δ = 8.15 (s, 1H), 7.31-7.25 (m, 2H), 7.25-7.20 (m, 1H), 7.17 (d, J = 7.6 Hz, 1H), 4.85-4.79 (m, 1H), 4.39 (s, 2H), 4.23-4.12 (m, 1H), 2.85-2.82 (m, 2H), 2.70-2.67 (m, 2H) |
| 131 | (cis)-3-(4-amino-3-(3-bromobenzyl)-1H-pyrazolo[3,4-d]pyrimidin-1-yl)cyclobutan-1-ol | 373/375 | 374/376 | (METHANOL-d4) δ = 8.28 (s, 1H), 7.46 (s, 1H), 7.43-7.37 (m, 1H), 7.23 (d, J = 4.8 Hz, 2H), 5.02-4.92 (m, 1H), 4.44 (s, 2H), 4.24-4.12 (m, 1H), 2.89-2.79 (m, 2H), 2.74-2.62 (m, 2H) |
| 132 | (cis)-3-(4-amino-3-(3-fluorobenzyl)-1H-pyrazolo[3,4-d]pyrimidin-1-yl)cyclobutan-1-ol | 313.1 | 314.1 | (METHANOL-d4) δ = 8.28 (s, 1H), 7.35-7.30 (m, 1H), 7.08 (d, J = 7.2 Hz, 1H), 7.02-6.98 (m, 2H), 5.00-4.94 (m, 1H), 4.46 (s, 2H), 4.22-4.15 (m, 1H), 2.86-2.83 (m, 2H), 2.69-2.66 (m, 2H) |
| 133 | (cis)-3-(4-amino-3-(3-(trifluoromethyl)benzyl)-1H-pyrazolo[3,4-d]pyrimidin-1-yl)cyclobutan-1-ol | 364.1 | 364.2 | (METHANOL-d4) δ = 8.18 (s, 1H), 7.61 (s, 1H), 7.55-7.47 (m, 3H), 4.92-4.89 (m, 1H), 4.50 (s, 2H), 4.22-4.13 (m, 1H), 2.88-2.81 (m, 2H), 2.68-2.65 (m, 2H) |

TABLE 11-continued

Compounds Prepared by Method K

| Compound No. | IUPAC Name | Expected MW (M) | LC/MS Observed (M + H) | 1H NMR (400 MHz) |
|---|---|---|---|---|
| 134 | 3-((4-amino-1-((cis)-3-hydroxycyclobutyl)-1H-pyrazolo[3,4-d]pyrimidin-3-yl)methyl)benzonitrile | 320.1 | 321.1 | (ACETONITRILE-d3) δ = 8.18 (s, 1H), 7.61 (s, 2H), 7.54-7.52 (m, 1H), 7.49-7.45 (m, 1H), 5.72 (s, 2H), 4.90-4.82 (m, 1H), 4.38 (s, 2H), 4.17-4.10 (m, 1H), 3.47 (d, J = 6.4 Hz, 1H), 2.82-2.77 (m, 2H), 2.56 (q, J = 8.8 Hz, 2H) |

Synthesis Method L: General Procedure Represented by the Preparation of 3-(3-chlorobenzyl)-1-((cis)-3-fluorocyclobutyl)-1H-pyrazolo[3,4-d]pyrimidin-4-amine

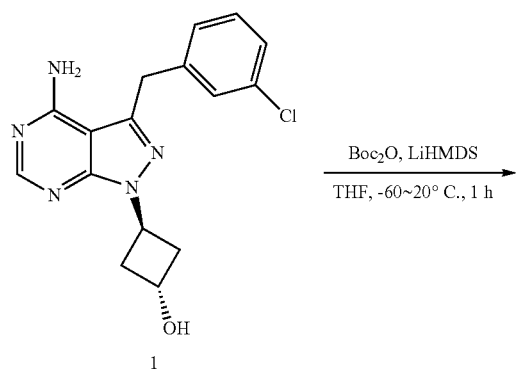

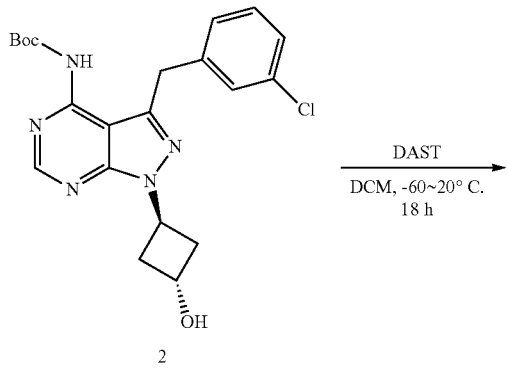

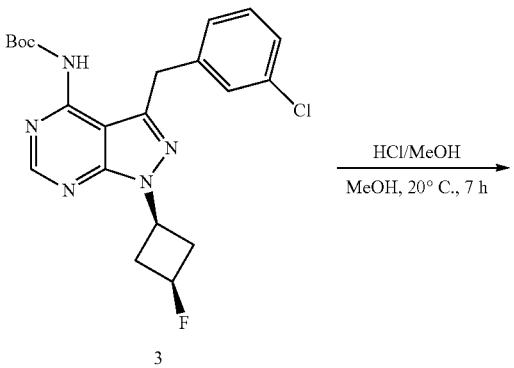

Step 1

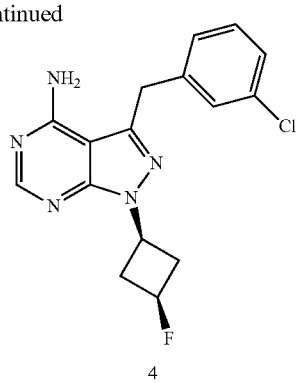

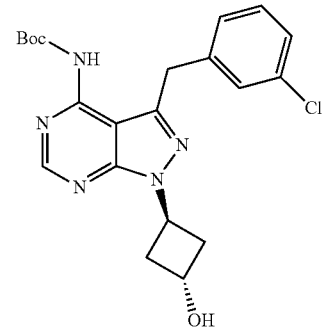

To a solution of (trans)-3-(4-amino-3-(3-chlorobenzyl)-1H-pyrazolo[3,4-d]pyrimidin-1-yl)cyclobutan-1-ol (1) (200 mg, 606 µmol, 1 eq) in tetrahydrofuran (5 mL) was added LiHMDS (1 M, 1.33 mL, 2.2 eq) dropwise at −60° C. under nitrogen atmosphere. The resulting mixture was stirred at −60° C. for 30 min, then Boc$_2$O (172 mg, 788 µmol, 181 µL, 1.3 eq) was added and the reaction mixture was warmed slowly to 20° C. and stirred for 1 h and then quenched by pouring into H$_2$O (10 mL). The mixture was extracted with ethyl acetate (3×10 mL) and the combined organic phase was dried (Na$_2$SO$_4$), concentrated under reduced pressure and purified by prep-TLC (petroleum ether/ethyl acetate=1/1) to give tert-butyl (3-(3-chlorobenzyl)-1-((trans)-3-hydroxycyclobutyl)-1H-pyrazolo[3,4-d]pyrimidin-4-yl)carbamate (2) (0.08 g, 149 µmol, 24.6% yield, 80% purity) as a white solid. $^1$H NMR: (400 MHz, DMSO-d$_6$) δ=9.91 (s, 1H), 8.61 (s, 1H), 7.29-7.22 (m, 3H), 7.05-7.01 (m, 1H), 5.51-5.45 (m, 1H), 5.27-5.24 (m, 1H), 4.56-4.52 (m, 1H), 4.41 (s, 2H), 2.79-2.74 (m, 2H), 2.46-2.40 (m, 2H), 1.46 (s, 9H).

Step 2

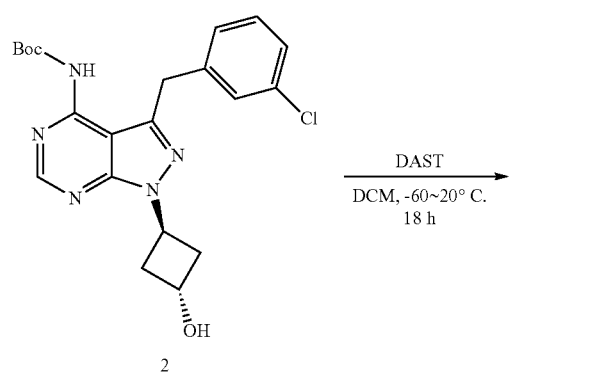

To a solution of tert-butyl (3-(3-chlorobenzyl)-1-((trans)-3-hydroxycyclobutyl)-1H-pyrazolo-[3,4-d]pyrimidin-4-yl)carbamate (2) (50 mg, 116 µmol, 1 eq) in DCM (3 mL) was added DAST (93.7 mg, 582 µmol, 76.8 µL, 5 eq) dropwise at −60° C. under nitrogen atmosphere. The mixture was slowly warmed to 20° C. and stirred for about 18 h. The reaction mixture was poured into 5 mL of water, extracted with DCM (3×5 mL), dried (sodium sulfate) and concentrated under reduced pressure to give tert-butyl (3-(3-chlorobenzyl)-1-((cis)-3-fluorocyclobutyl)-1H-pyrazolo-[3,4-d]pyrimidin-4-yl)carbamate (3) (50 mg, crude) as a black red solid which was used for next step directly.

Step 3

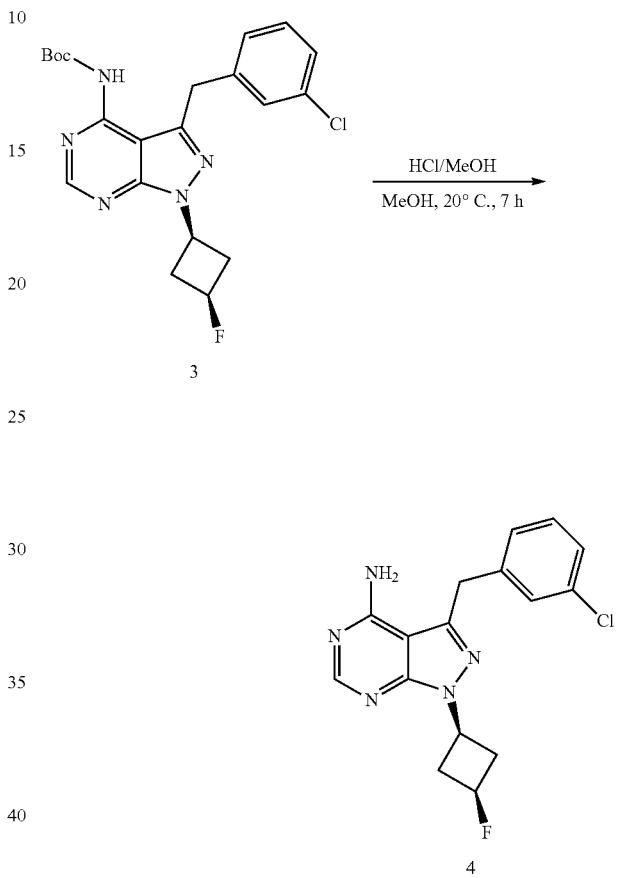

To a solution of tert-butyl (3-(3-chlorobenzyl)-1-((cis)-3-fluorocyclobutyl)-1H-pyrazolo-[3,4-d]pyrimidin-4-yl)carbamate (3) (50 mg, crude) in methanol (3 mL) was added HCl/MeOH (4 M, 5 mL) at 20° C. The mixture was stirred at 20° C. for about 7 h, concentrated under reduced pressure and the remaining residue dissolved in mL of DMSO and purified by prep-HPLC (basic condition) to give 3-(3-chlorobenzyl)-1-((cis)-3-fluorocyclobutyl)-1H-pyrazolo[3,4-d]pyrimidin-4-amine (4; Compound 135) (4.8 mg, 14.2 µmol, 12.2% yield, 97.8% purity) as a gray solid. LCMS: (M+H)$^+$: 332.0, Rt: 2.318 min. LC/MS (The gradient was 10-100% B in 3.4 min with hold at 100% B for 0.45 m, 100-10% Bin 0.01 min, and then held at 10% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 m particles). Detection methods are diode array (DAD) and evaporative light scattering (ELSD) detection as well as positive electrospray ionization (MS). $^1$H NMR: (400 MHz, CD3CN) δ=8.21 (s, 1H), 7.35-7.28 (m, 3H), 7.21 (d, J=6.8 Hz, 1H), 5.78 (s, 2H), 5.13-4.89 (m, 2H), 4.36 (s, 2H), 3.02-2.88 ((m, 4H).

TABLE 12

Compounds Prepared by Method L

| Compound No. | IUPAC Name | Expected MW (M) | LC/MS Observed (M + H) | 1H NMR (400 MHz) |
|---|---|---|---|---|
| 135 | 3-(3-chlorobenzyl)-1-((cis)-3-fluorocyclobutyl)-1H-pyrazolo[3,4-d]pyrimidin-4-amine | 331.1 | 332 | (ACETONITRILE-d3) δ = 8.21 (s, 1H), 7.35-7.28 (m, 3H), 7.21 (d, J = 6.8 Hz, 1H), 5.78 (s, 2H), 5.13-5.09 (m, 0.5H) 4.99-4.89 (m, 1.5H), 4.36 (s, 2H), 3.02-2.88 (m, 4H) |
| 136 | 3-(3-chlorobenzyl)-1-((trans)-3-fluorocyclobutyl)-1H-pyrazolo[3,4-d]pyrimidin-4-amine | 331.1 | 332 | (ACETONITRILE-d3) δ = 8.18 (s, 1H), 7.32-7.25 (m, 3H), 7.18 (d, J = 7.2 Hz, 1H), 5.68 (s, 2H), 5.56-5.51 (m, 1.5H), 5.50-5.42 (m, 0.5H) 4.32 (s, 2H), 2.95-2.89 (m, 2H), 2.84-2.76 (m, 2H) |
| 137 | 1-((Trans)-3-fluorocyclobutyl)-3-((4-(trifluoromethyl)pyridin-2-yl)oxy)-1H-pyrazolo[3,4-d]pyrimidin-4-amine | 368.1 | 369 | (ACETONITRILE-d3) δ = 8.36 (d, J = 5.2 Hz, 1H), 8.23 (s, 1H), 7.56 (s, 1H), 7.46 (d, J = 5.2 Hz, 1H), 6.01 (s, 2H), 5.56-5.51 (m, 1H), 5.47-5.45 (m, 0.5H), 5.33-5.31 (m, 0.5H), 2.88-2.75 (m, 4H) |
| 138 | 2-((4-amino-1-((trans)-3-fluorocyclobutyl)-1H-pyrazolo[3,4-d]pyrimidin-3-yl)oxy)isonicotinonitrile | 325.1 | 326 | (METHANOL-d4) δ = 8.38 (d, J = 4.4 Hz, 1H), 8.30 (s, 1H), 7.74 (s, 1H), 7.56 (dd, J = 1.2, 5.2 Hz, 1H), 5.64-5.60 (m, 1H), 5.44-5.43 (m, 0.5H), 5.30-5.27 (m, 0.5H), 2.95-2.81 (m, 4H) |
| 139 | 1-((trans)-3-fluorocyclobutyl)-3-(3-(trifluoromethyl)benzyl)-1H-pyrazolo[3,4-d]pyrimidin-4-amine | 365.3 | 366.1 | (ACETONITRILE-d3) δ = 8.21 (s, 1H), 7.64 (s, 1H), 7.59-7.58 (m, 1H), 7.52 (d, J = 4.4 Hz, 2H), 5.78 (s, 2H), 5.59-5.52 (m, 1H), 5.47-5.39 (m, 1H), 4.43 (s, 2H), 2.98-2.81 (m, 4H) |

Synthesis Method M: General Procedure Represented by the Preparation of 3-(4-amino-3-(3-chlorobenzyl)-1H-pyrazolo[3,4-d]pyrimidin-1-yl)cyclobutan-1-one

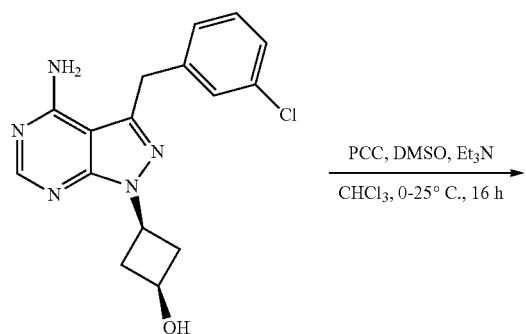

PCC, DMSO, Et₃N
CHCl₃, 0-25° C., 16 h

-continued

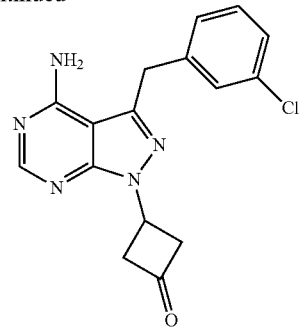

(Cis)-3-(4-amino-3-(3-chlorobenzyl)-1H-pyrazolo[3,4-d]pyrimidin-1-yl)-cyclobutan-1-ol (74.3 mg, 225 μmol, 1 eq, TFA), DMSO (194 mg, 2.48 mmol, 194 μL, 11 eq), Et₃N (137 mg, 1.35 mmol, 188 μL, 6 eq) and CHCl₃ (10 mL) were combined followed by the addition of PCC (194 mg, 901p mol, 4 eq) at 0° C. The mixture was stirred at 25° C. for 16 h, filtered and the filtrate concentrated under reduced pressure to give a residue which was purified by prep-HPLC (neutral condition) to give 3-(4-amino-3-(3-chlorobenzyl)-1H-pyrazolo[3,4-d]pyrimidin-1-yl)cyclobutan-1-one (Compound 140) (11.6 mg, 34.6 µmol, 15.4% yield, 97.8% purity) as a white solid. LCMS: (M+H)$^+$: 328. 1, RT: 2.151 min LC/MS (The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 µm particles). Detection methods are diode array (DAD) and evaporative light scattering (ELSD) detection as well as positive electrospray ionization (MS). $^1$H NMR: (400 MHz, DMSO-d$_6$) δ=8.15 (s, 1H), 7.35 (s, 1H), 7.30-7.22 (m, 2H), 7.16 (d, J=6.8 Hz, 1H), 5.50 (t, J=6.4 Hz, 1H), 4.38 (s, 2H), 3.61 (d, J=6.8 Hz, 4H).

TABLE 13

Compounds Prepared by Method M

| Compound No. | IUPAC Name | Expected MW (M) | LC/MS Observed (M + H) | 1H NMR (400 MHz) |
|---|---|---|---|---|
| 140 | 3-(4-amino-3-(3-chlorobenzyl)-1H-pyrazolo[3,4-d]pyrimidin-1-yl)cyclobutan-1-one | 327 | 328.1 | (DMSO-d6) δ = 8.15 (s, 1H), 7.35 (s, 1H), 7.30-7.22 (m, 2H), 7.16 (d, J = 6.8 Hz, 1H), 5.50 (t, J = 6.4 Hz, 1H), 4.38 (s, 2H), 3.61 (d, J = 6.8 Hz, 4H) |
| 141 | 3-(4-amino-3-((4-(trifluoromethyl)pyridin-2-yl)oxy)-1H-pyrazolo[3,4-d]pyrimidin-1-yl)cyclobutan-1-one | 364.1 | 365.1 | (ACETONITRILE-d3) δ = 8.40 (d, J = 5.2 Hz, 1H), 8.30 (s, 1H), 7.61 (s, 1H), 7.52 (d, J = 5.2 Hz, 1H), 5.61 (q, J = 7.2 Hz, 1H), 3.62 (d, J = 7.2 Hz, 4H) |
| 142 | 2-((4-amino-1-(3-oxocyclobutyl)-1H-pyrazolo[3,4-d]pyrimidin-3-yl)oxy)isonicotinonitrile | 321.1 | 322.1 | (ACETONITRILE-d3) δ = 10.61 (s, 1H), 8.37 (d, J = 5.2 Hz, 1H), 8.30 (s, 1H), 7.66 (s, 1H), 7.54 (d, J = 5.2 Hz, 1H), 7.15 (s, 1H), 5.61 (q, J = 7.2 Hz, 1H), 3.62 (d, J = 6.8 Hz, 4H) |
| 143 | 3-(4-amino-3-((4-chloropyridin-2-yl)oxy)-1H-pyrazolo[3,4-d]pyrimidin-1-yl)cyclobutan-1-one | 330 | 331 | (ACETONITRILE-d3) δ = 8.28 (s, 1H), 8.12 (d, J = 5.6 Hz, 1H), 7.38 (d, J= 1.6 Hz, 1H), 7.29 (dd, J = 1.6, 5.6 Hz, 1H), 5.63-5.55 (m, 1H), 3.62-3.60 (m, 4H) |
| 144 | 3-(4-amino-3-((2-chloropyridin-4-yl)oxy)-1H-pyrazolo[3,4-d]pyrimidin-1-yl)cyclobutan-1-one | 330 | 331 | (ACETONITRILE-d3) δ = 8.39 (d, J = 5.6 Hz, 1H), 8.29 (s, 1H), 7.48 (d, J = 1.6 Hz, 1H), 7.43 (dd, J = 2.4, 6.0 Hz, 1H), 5.62-5.55 (m, 1H), 3.66-3.61 (m, 4H) |

Synthesis Method N General Procedure Represented by the Preparation of 1-cyclopropyl-3-((4-(tetrahydro-2H-pyran-4-yl)pyridin-2-yl)oxy)-1H-pyrazolo[3,4-d]pyrimidin-4-amine Synthetic Scheme 15 Representing Method N

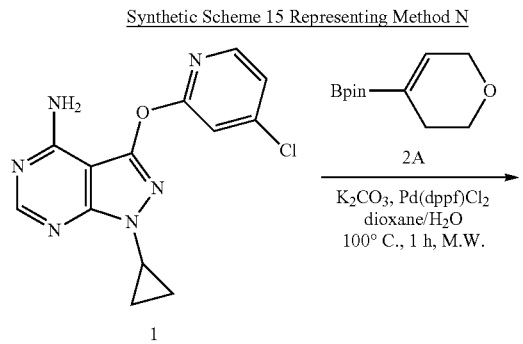

Step 1

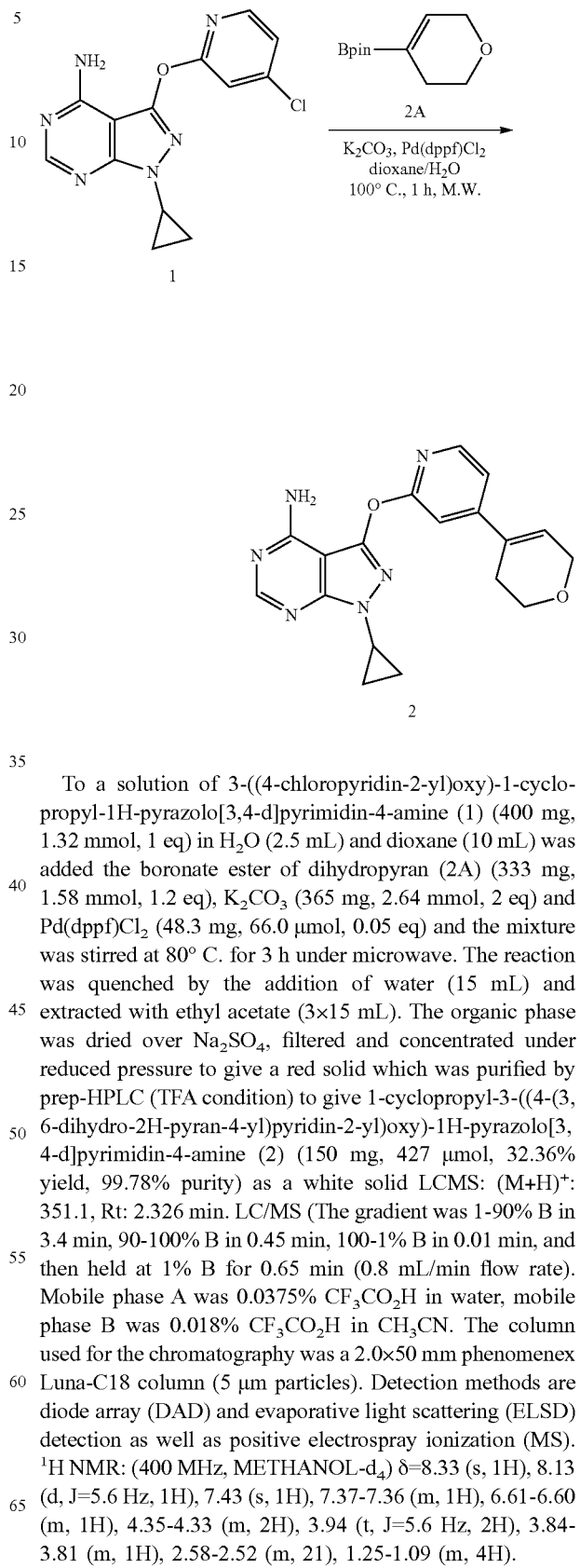

To a solution of 3-((4-chloropyridin-2-yl)oxy)-1-cyclopropyl-1H-pyrazolo[3,4-d]pyrimidin-4-amine (1) (400 mg, 1.32 mmol, 1 eq) in H$_2$O (2.5 mL) and dioxane (10 mL) was added the boronate ester of dihydropyran (2A) (333 mg, 1.58 mmol, 1.2 eq), K$_2$CO$_3$ (365 mg, 2.64 mmol, 2 eq) and Pd(dppf)Cl$_2$ (48.3 mg, 66.0 μmol, 0.05 eq) and the mixture was stirred at 80° C. for 3 h under microwave. The reaction was quenched by the addition of water (15 mL) and extracted with ethyl acetate (3×15 mL). The organic phase was dried over Na$_2$SO$_4$, filtered and concentrated under reduced pressure to give a red solid which was purified by prep-HPLC (TFA condition) to give 1-cyclopropyl-3-((4-(3,6-dihydro-2H-pyran-4-yl)pyridin-2-yl)oxy)-1H-pyrazolo[3,4-d]pyrimidin-4-amine (2) (150 mg, 427 μmol, 32.36% yield, 99.78% purity) as a white solid LCMS: (M+H)$^+$: 351.1, Rt: 2.326 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS). $^1$H NMR: (400 MHz, METHANOL-d$_4$) δ=8.33 (s, 1H), 8.13 (d, J=5.6 Hz, 1H), 7.43 (s, 1H), 7.37-7.36 (m, 1H), 6.61-6.60 (m, 1H), 4.35-4.33 (m, 2H), 3.94 (t, J=5.6 Hz, 2H), 3.84-3.81 (m, 1H), 2.58-2.52 (m, 21), 1.25-1.09 (m, 4H).

Step 2

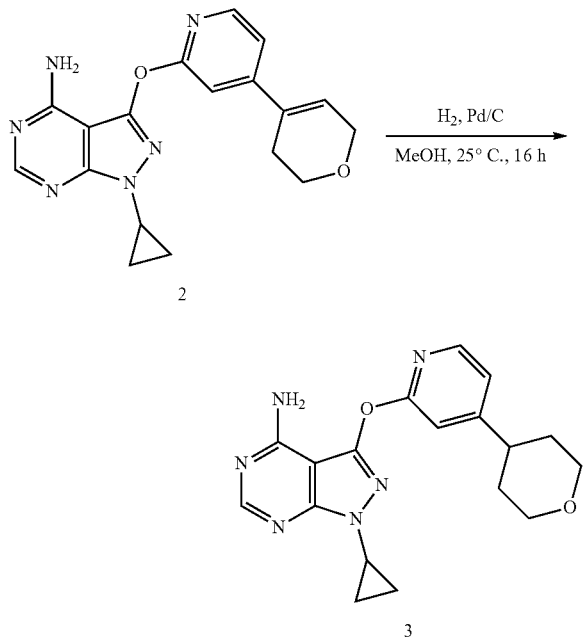

To a solution of 1-cyclopropyl-3-((4-(3,6-dihydro-2H-pyran-4-yl)pyridin-2-yl)oxy)-1H-pyrazolo[3,4-d]pyrimidin-4-amine (2) (100 mg, 215 μmol, 1 eq, TFA) in MeOH (20 mL) was added Pd/C (20 mg, 10% purity). The suspension was degassed under vacuum and purged with H₂ several times. The mixture was stirred under H₂ (15 psi) at 25° C. for 16 h, filtered and the filtrate concentrated in vacuum. The residue was purified by prep-HPLC (neutral condition) to give 1-cyclopropyl-3-((4-(tetrahydro-2H-pyran-4-yl)pyridin-2-yl)oxy)-1H-pyrazolo[3,4-d]pyrimidin-4-amine (3; Compound 145) (38.4 mg, 107 μmol, 49.6% yield, 98% purity) as a white solid. LCMS: (M+H)⁺: 353.1, Rt: 2.308 min. LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF₃CO₂H in water, mobile phase B was 0.018% CF₃CO₂H in CH₃CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS). ¹H NMR: (400 MHz, DMSO-d₆) δ=8.19 (s, 1H), 8.04 (d, J=5.2 Hz, 1H), 7.12 (d, J=5.2 Hz, 1H), 7.09 (s, 1H), 3.98-3.94 (m, 2H), 3.73-3.65 (m, 1H), 3.47-3.42 (m, 2H), 2.89-2.85 (m, 1H), 1.77-1.67 (m, 4H), 1.06-0.99 (m, 4H).

TABLE 14

| | Compounds Prepared by Method N | | | |
|---|---|---|---|---|
| Compound No. | IUPAC Name | Expected MW (M) | LC/MS Observed (M + H) | 1H NMR (400 MHz) |
| 146 | 1-cyclopropyl-3-((2-(tetrahydro-2H-pyran-4-yl)pyridin-4-yl)oxy)-1H-pyrazolo[3,4-d]pyrimidin-4-amine | 352.1 | 353.1 | (DMSO-d6) δ = 8.45 (d, J = 6.0 Hz, 1H), 8.21 (s, 1H), 7.25 (d, J = 2.4 Hz, 1H), 7.20-7.18 (m, 1H), 3.95-3.93 (m, 2H), 3.71-3.69 (m, 1H), 3.46-3.40 (m, 2H), 2.94-2.91 (m, 1H), 1.77-1.72 (m, 4H), 1.12-1.01 (m, 4H) |

Synthesis Method O General Procedure Represented by the Preparation of 7-cyclobutyl-5-(pyridin-2-ylmethyl)-7H-pyrrolo[2,3-d]pyrimidin-4-amine

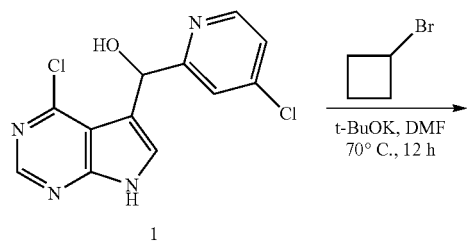

1

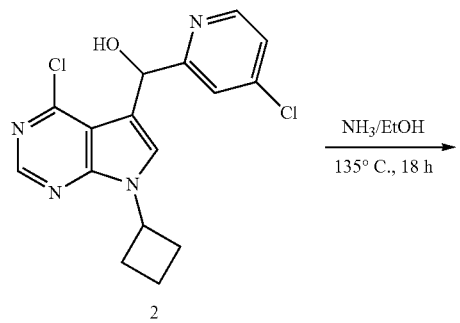

2

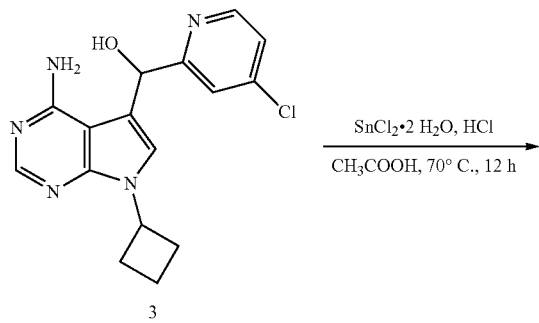

3

Step 1. Procedure for Preparation of (4-chloro-7-cyclobutyl-7H-pyrrolo[2,3-d]pyrimidin-5-yl)(4-chloropyridin-2-yl)methanol (2)

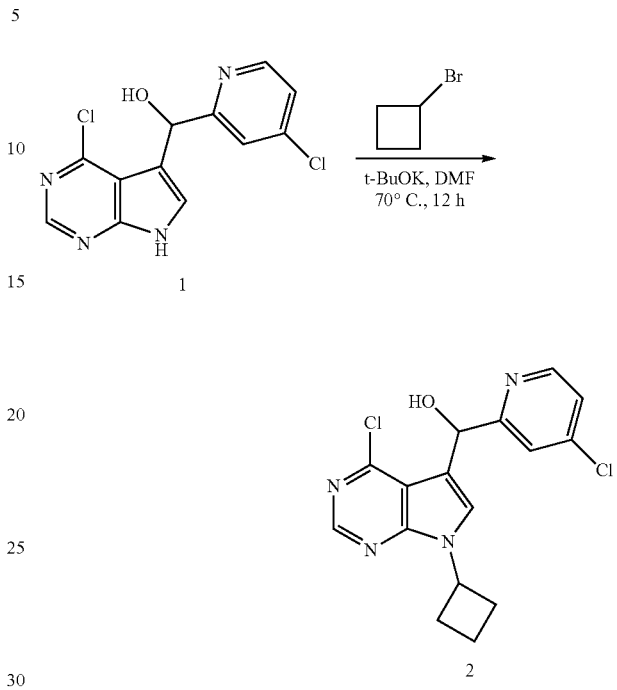

A mixture of (4-chloro-7H-pyrrolo[2,3-d]pyrimidin-5-yl)(4-chloropyridin-2-yl)methanol (1) (1.0 g, 3.39 mmol, 1 eq), bromocyclobutane (915 mg, 6.78 mmol, 2 eq), t-BuOK. (760 mg, 6.78 mmol, 2 eq) and DMF (5 mL) was stirred at 70° C. for 12 h. The reaction mixture was partitioned between water (200 mL) and EtOAc (100 mL) and the organic phase was separated. The aqueous phase was extracted with EtOAc (3×60 mL) and the combined organic phases were washed with brine, dried over Na$_2$SO$_4$ (2 g) and concentrated under reduced pressure. The product was purified by column chromatography (SiO$_2$, Petroleum ether/Ethyl acetate=50/1 to 1/1) to give (4-chloro-7-cyclobutyl-7H-pyrrolo[2,3-d]pyrimidin-5-yl)(4-chloropyridin-2-yl)methanol (2) (800 mg, 33.8% yield) as a yellow solid

Step 2. Procedure for Preparation of (4-amino-7-cyclobutyl-7H-pyrrolo[2,3-d]pyrimidin-5-yl)(4-chloropyridin-2-yl)methanol (3)

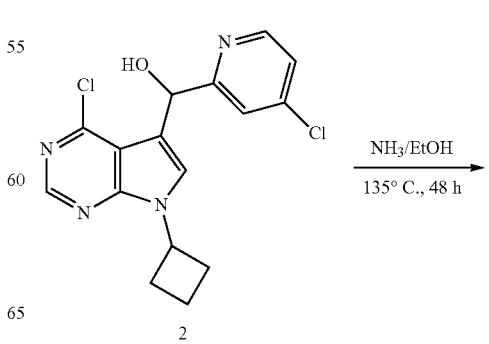

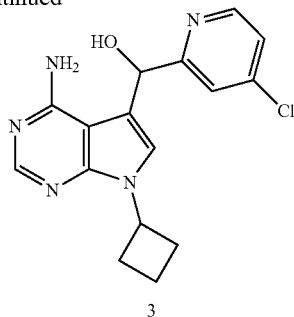

3

A mixture of (4-chloro-7-cyclobutyl-7H-pyrrolo[2,3-d]pyrimidin-5-yl)(4-chloropyridin-2-yl)methanol (2) (300 mg, 859.07 μmol, 1 eq) and NH₃/EtOH (2 M, 5 mL) was stirred at 135° C. for 48 h in sealed tube. LCMS showed the reaction was completed. The reaction was concentrated to afford the crude product. The crude product was purified by prep-HPLC (neutral condition) to give (4-amino-7-cyclobutyl-7H-pyrrolo[2,3-d]pyrimidin-5-yl)(4-chloropyridin-2-yl)methanol (3) (36.5 mg, 12.9% yield) as a light yellow solid. LCMS: (M+H)⁺: 330.0, Rt: 2.493 min. ¹H NMR: (400 MHz, METHANOL-d₄) δ=8.43 (d, J=5.2 Hz, 1H), 8.05 (s, 1H), 7.68 (d, J=2.0 Hz, 1H), 7.36 (dd, J=2.0, 5.6 Hz, 1H), 7.26 (s, 1H), 6.05 (s, 1H), 5.12 (q, J=8.8 Hz, 1H), 2.50-2.43 (m, 4H), 1.94-1.86 (m, 2H).

Step 3. Procedure for Preparation of 5-((4-chloropyridin-2-yl)methyl)-7-cyclobutyl-7H-pyrrolo[2,3-d]pyrimidin-4-amine (4)

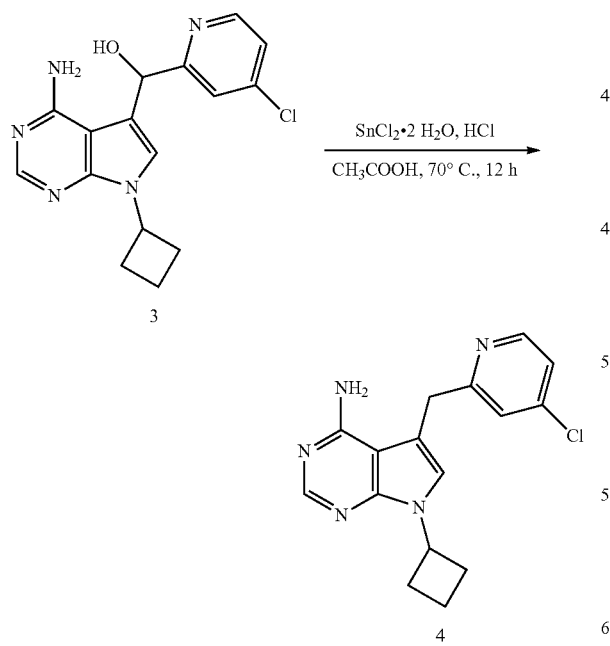

To a solution of (4-amino-7-cyclobutyl-7H-pyrrolo[2,3-d]pyrimidin-5-yl)(4-chloropyridin-2-yl)methanol (3) (10 mg, 30.3 μmol, 1 eq) in CH₃COOH (2 mL) was added SnCl₂·2H₂O (54.7 mg, 243 μmol, 8 eq) and HCl (598 μg, 6.06 μmol, 0.59 μL, 37% purity, 0.2 eq). The mixture was stirred at 70° C. for 12 h and concentrated to afford the crude product, which was purified by prep-HPLC (HCl condition) to give 5-((4-chloropyridin-2-yl)methyl)-7-cyclobutyl-7H-pyrrolo[2,3-d]pyrimidin-4-amine (4; Compound 147) (2.8 mg, 4.20% yield) as a light yellow solid. LCMS: (M+H)⁺: 314.1, Rt: 2.777 min. ¹H NMR: (400 MHz, MeOD-d₄) δ=8.73 (d, J=6.0 Hz, 1H), 8.29 (s, 1H), 7.92 (d, J=6.0 Hz, 1H), 7.89 (s, 1H), 7.68 (s, 1H), 5.29 (q, J=8.8 Hz, 1H), 4.70 (s, 2H), 2.64-2.48 (m, 4H), 1.99-1.90 (m, 2H).

Alternative Method O: General Procedure Represented by the Preparation of 7-cyclobutyl-5-(pyridin-2-ylmethyl)-7H-pyrrolo[2,3-d]pyrimidin-4-amine

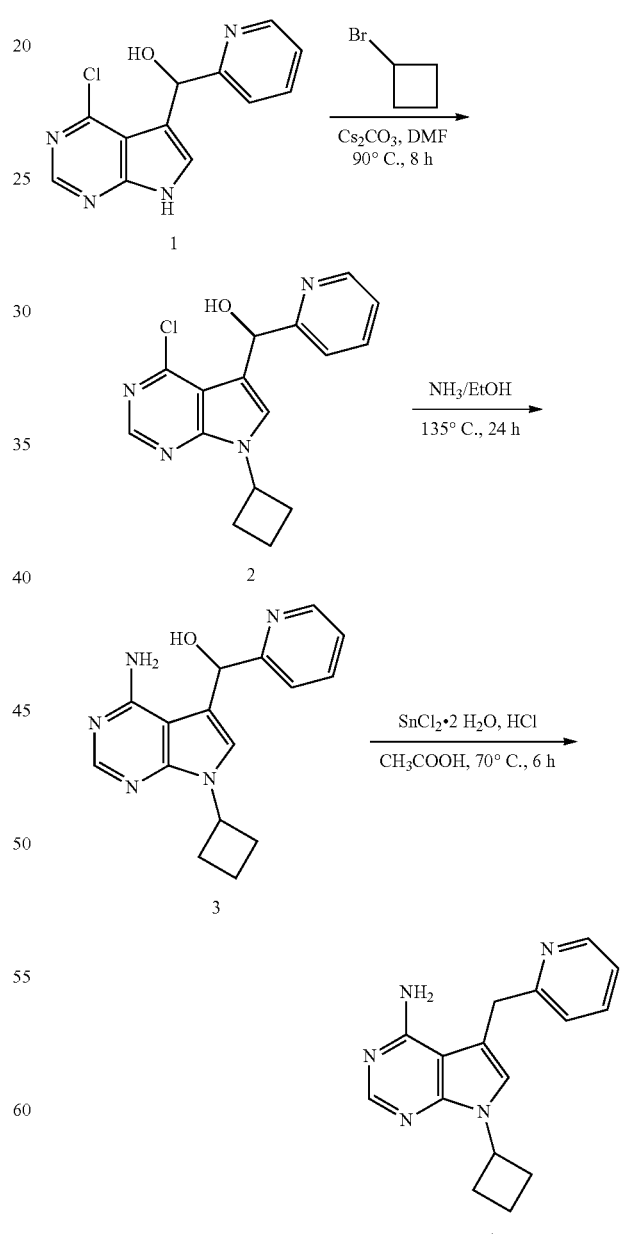

Step 1. Procedure for Preparation of (4-chloro-7-cyclobutyl-7H-pyrrolo[2,3-d]pyrimidin-5-yl)(pyridin-2-yl)methanol (2)

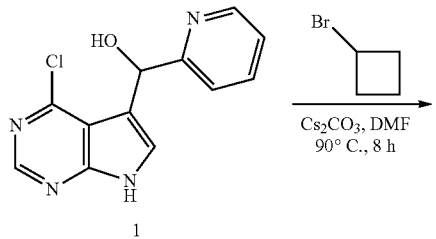

1

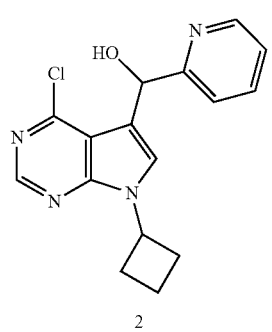

2

A mixture of (4-chloro-7H-pyrrolo[2,3-d]pyrimidin-5-yl)(pyridin-2-yl)methanol (1) (1 g, 3.84 mmol, 1 eq), bromocyclobutane (1.04 g, 7.67 mmol, 724 μL, 2 eq), Cs$_2$CO$_3$ (2.50 g, 7.67 mmol, 2 eq) and DMF (10 mL) was stirred at 90° C. for 8 h. The reaction mixture was partitioned between water (200 mL) and Ethyl acetate (100 mL). The organic phase was separated and the aqueous phase was washed with 3×60 mL of EtOAc. The combined organic phases were washed with brine, dried over Na$_2$SO$_4$ (2 g), and concentrated under reduced pressure. The residue was purified by column chromatography (SiO$_2$, Petroleum ether/Ethyl acetate=50/1 to 1/1) to give (4-chloro-7-cyclobutyl-7H-pyrrolo[2,3-d]pyrimidin-5-yl)(pyridin-2-yl)methanol (2) (500 mg, 20.7% yield) as a yellow solid.

Step 2. Procedure for Preparation of (4-amino-7-cyclobutyl-7H-pyrrolo[2,3-d]pyrimidin-S-yl)(pyridin-2-yl)methanol (3)

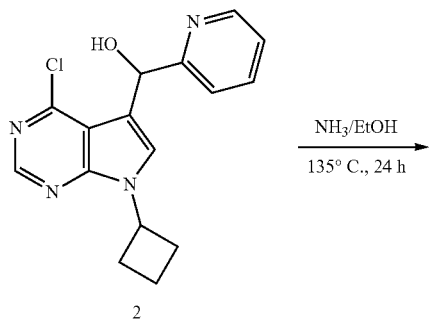

2

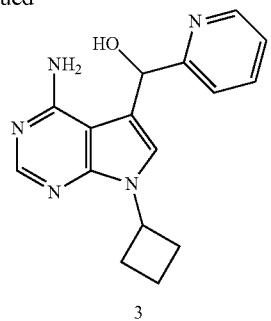

3

A mixture of (4-chloro-7-cyclobutyl-7H-pyrrolo[2,3-d]pyrimidin-5-yl)(pyridin-2-yl)methanol (2) (250 mg, 794 μmol, 1 eq) and NH$_3$/EtOH (2 M, 3 mL) was stirred at 135° C. for 24 h in a sealed tube. The reaction mixture was concentrated and the crude product purified by prep-HPLC (neutral condition) to give (4-amino-7-cyclobutyl-7H-pyrrolo[2,3-d]pyrimidin-5-yl)(pyridin-2-yl)methanol (3) (23 mg, 9.51% yield, 97% purity) as a light yellow solid. LCMS: (M+H)$^+$: 296.1, Rt: 2.227 min. $^1$H NMR: (400 MHz, METHANOL-d$_4$) δ=8.50 (d, J=4.8 Hz, 1H), 8.04 (s, 1H), 7.87-7.81 (m, 1H), 7.63 (d, J=8.0 Hz, 1H), 7.31 (dd, J=4.8, 6.4 Hz, 1H), 7.18 (s, 1H), 6.05 (s, 1H), 5.12 (q, J=8.8 Hz, 1H), 2.49-2.42 (m, 4H), 1.93-1.84 (m, 2H).

Step 3. Procedure for Preparation of 7-cyclobutyl-5-(pyridin-2-ylmethyl)-7H-pyrrolo[2,3-d]pyrimidin-4-amine (4)

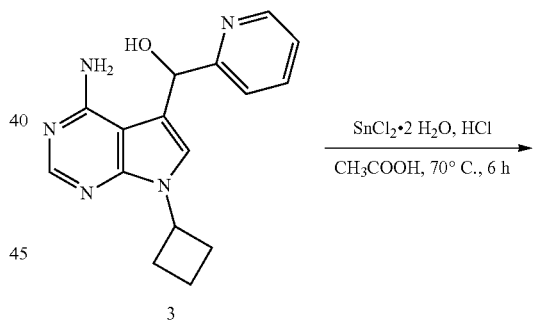

3

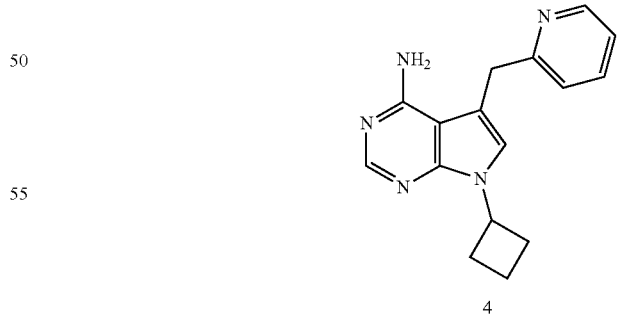

4

To a solution of (4-amino-7-cyclobutyl-7H-pyrrolo[2,3-d]pyrimidin-5-yl)(pyridin-2-yl)methanol (3) (10 mg, 33.9 μmol, 1 eq) in CH$_3$COOH (2 mL) was added SnCl$_2$·2H$_2$O (61.1 mg, 271 μmol, 8 eq) and HCl (667 μg, 6.77 μmol, 0.65 μL, 37% purity, 0.2 eq). The mixture was stirred at 70° C. for 12 h and concentrated to afford the crude product, which was purified by prep-HPLC (HCl condition) to give 7-cyclobutyl-5-(pyridin-2-ylmethyl)-7H-pyrrolo[2,3-d]pyrimidin-4-amine (4; Compound 148) (2.8 mg, 14.8% yield) as a light yellow solid. LCMS: (M+H)+: 280.1, Rt: 2.517 min. $^1$H NMR: (400 MHz, MeOD-$d_4$) δ=8.81 (d, J=5.6 Hz, 1H), 8.55 (t, J=7.6 Hz, 1H), 8.31 (s, 1H), 7.98 (t, J=6.8 Hz, 1H), 7.84 (d, J=8.0 Hz, 1H), 7.65 (s, 1H), 5.36-5.25 (m, 1H), 4.82 (s, 2H), 2.63-2.49 (m, 4H), 1.94 (tt, J=5.2, 9.6 Hz, 2H).

Synthesis Method P: General Procedure Represented by the Preparation of 1-cyclopropyl-3-((4-methoxypyridin-2-yl)methyl)-1H-pyrazolo[3,4-d]pyrimidin-4-amine

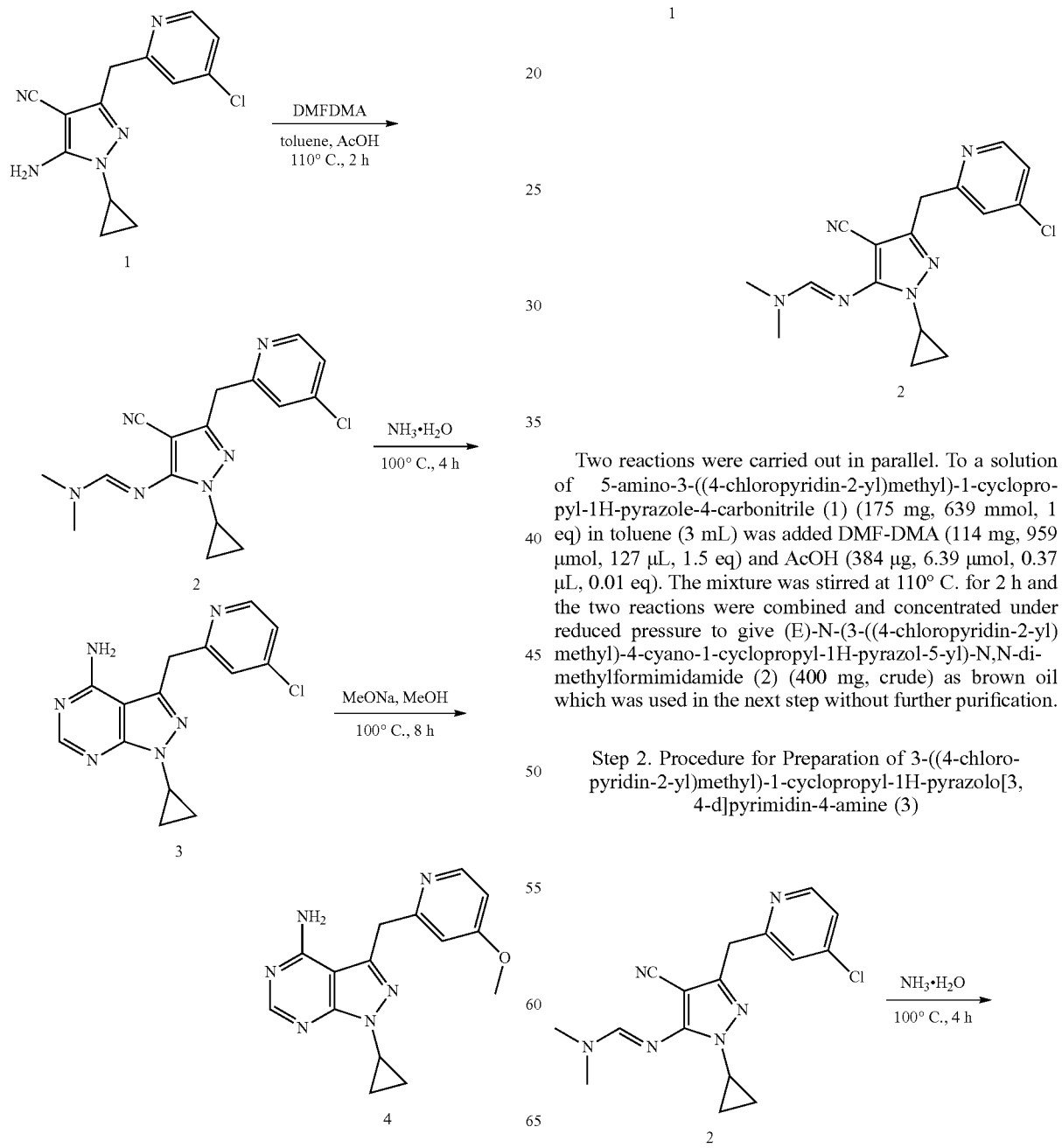

Step 1. Procedure for Preparation of (E)-N'-(3-((4-chloropyridin-2-yl)methyl)-4-cyano-1-cyclopropyl-1H-pyrazol-5-yl)-N,N-dimethylformimidamide (2)

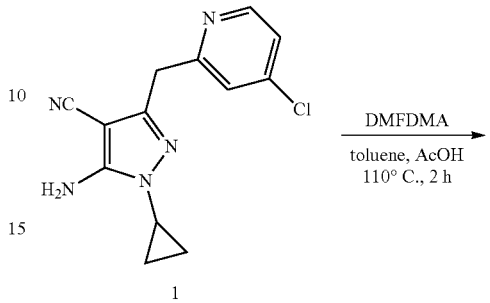

Two reactions were carried out in parallel. To a solution of 5-amino-3-((4-chloropyridin-2-yl)methyl)-1-cyclopropyl-1H-pyrazole-4-carbonitrile (1) (175 mg, 639 mmol, 1 eq) in toluene (3 mL) was added DMF-DMA (114 mg, 959 μmol, 127 μL, 1.5 eq) and AcOH (384 μg, 6.39 μmol, 0.37 μL, 0.01 eq). The mixture was stirred at 110° C. for 2 h and the two reactions were combined and concentrated under reduced pressure to give (E)-N-(3-((4-chloropyridin-2-yl)methyl)-4-cyano-1-cyclopropyl-1H-pyrazol-5-yl)-N,N-dimethylformimidamide (2) (400 mg, crude) as brown oil which was used in the next step without further purification.

Step 2. Procedure for Preparation of 3-((4-chloropyridin-2-yl)methyl)-1-cyclopropyl-1H-pyrazolo[3,4-d]pyrimidin-4-amine (3)

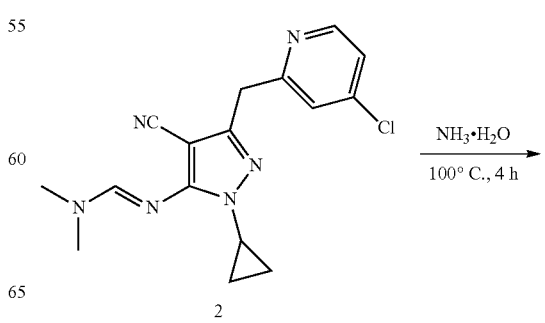

-continued

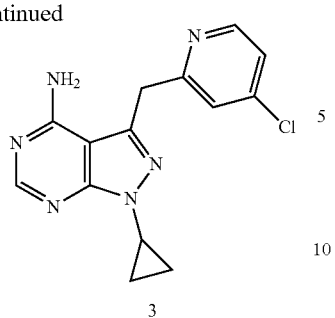

3

A mixture of (E)-N-(3-((4-chloropyridin-2-yl)methyl)-4-cyano-1-cyclopropyl-1H-pyrazol-5-yl)-N,N-dimethylformimidamide (2) (400 mg, 1.22 mmol, 1 eq) in NH$_3$.H$_2$O (6 mL) was stirred at 100° C. for 4 h. The mixture was concentrated under reduced pressure to give a residue which was purified by prep-HPLC (neutral condition) to give 3-((4-chloropyridin-2-yl)methyl)-1-cyclopropyl-1H-pyrazolo[3,4-d]pyrimidin-4-amine (3) (60 mg, 200 µmol, 16.4% yield) as a yellow solid.

Step 3. Procedure for Preparation of 3-((4-chloropyridin-2-yl)methyl)-1-cyclopropyl-1H-pyrazolo[3,4-d]pyrimidin-4-amine (4)

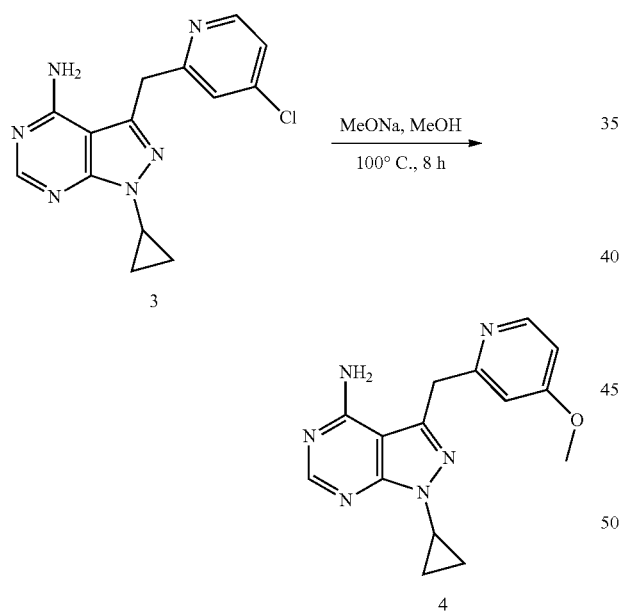

The mixture of 3-((4-chloropyridin-2-yl)methyl)-1-cyclopropyl-1H-pyrazolo[3,4-d]pyrimidin-4-amine (3) (50 mg, 166.25 µmol, 1 eq) and NaOMe (44.91 mg, 831.27 µmol, 5 eq) in MeOH (8 mL) was stirred at 100° C. for about 8 h in 30 mL sealed tube. LCMS showed the reaction was completed. The mixture was filtered and the filtrate was purified by prep-HPLC (neutral condition) to give 3-((4-chloropyridin-2-yl)methyl)-1-cyclopropyl-1H-pyrazolo[3,4-d]pyrimidin-4-amine (4; Compound 149) (7 mg, 23.6 µmol, 14.2% yield) as a white solid. LCMS: 1 (M+H)$^+$: 297.1, Rt: 2.086 min. $^1$H NMR: (400 MHz, METHANOL-d$_4$) δ=8.33 (d, J=6.0 Hz, 1H), 8.12 (s, 1H), 7.05 (d, J=2.4 Hz, 1H), 6.89 (dd, J=2.4, 6.0 Hz, 1H), 4.71 (s, 2H), 3.97 (tt, J=3.6, 7.2 Hz, 1H), 3.88 (s, 3H), 1.35-1.30 (m, 2H), 1.26-1.19 (m, 2H).

Synthesis Method Q: General Procedure Represented by the Preparation of 1-((trans)-3-fluorocyclobutyl)-3-(3-fluorophenoxy)-1H-pyrazolo[3,4-d]pyrimidin-4-amine

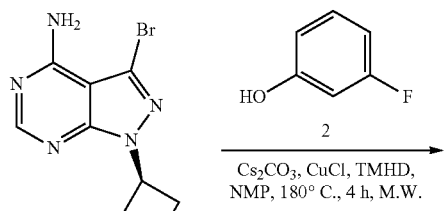

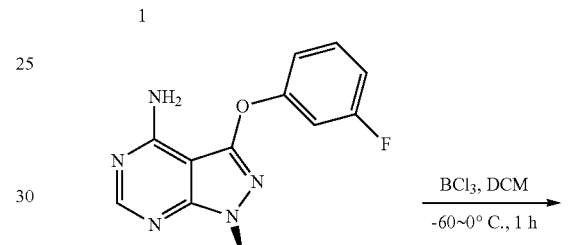

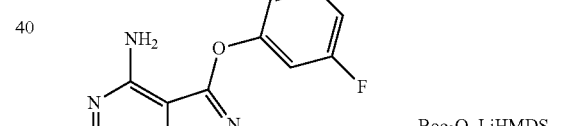

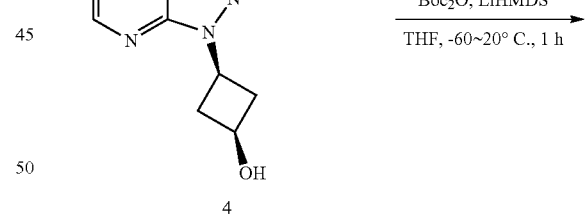

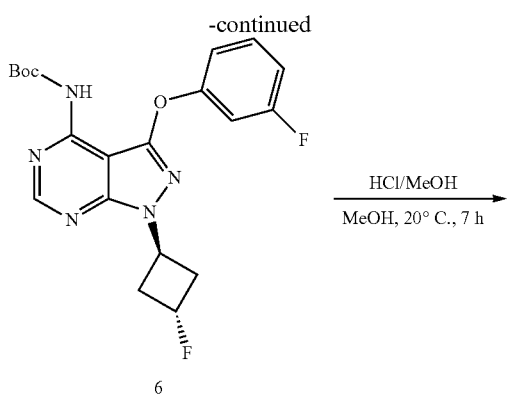

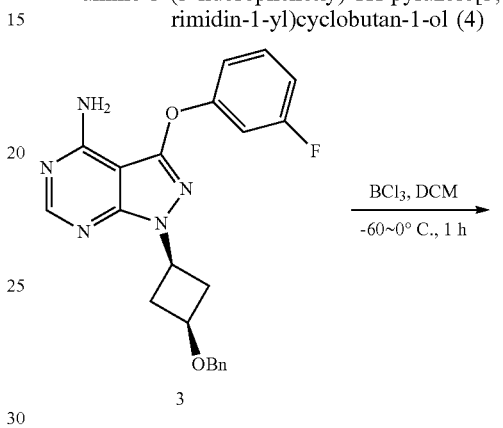

μL, 2 eq), CS$_2$CO$_3$ (348.25 mg, 1.07 mmol, 2 eq), TMHD (222.57 mg, 1.21 mmol, 248.69 μL, 2.26 eq) and CuCl (55.55 mg, 561.15 μmol, 13.42 μL, 1.05 eq) in NMP (2 mL) was added to a 5 mL Biotage microwave vial with a Teflon coated stirring bar under N$_2$. The vial was sealed and heated at 180° C. for 4 h under microwave irradiation. LCMS showed the reaction was completed. The reaction mixture was filtered and the filtrate was purified by prep-HPLC (TFA condition) to give 1-((1s,3s)-3-(benzyloxy)cyclobutyl)-3-(3-fluorophenoxy)-1H-pyrazolo[3,4-d]pyrimidin-4-amine (3) (0.1 g, 192.51 μmol, 12.01% yield, TFA) as a light yellow solid.

Step 2. Procedure for the Preparation of (cis)-3-(4-amino-3-(3-fluorophenoxy)-1H-pyrazolo[3,4-d]pyrimidin-1-yl)cyclobutan-1-ol (4)

Step 1. Procedure for Preparation of 1-((cis)-3-(benzyloxy)cyclobutyl)-3-(3-fluorophenoxy)-1H-pyrazolo[3,4-d]pyrimidin-4-amine

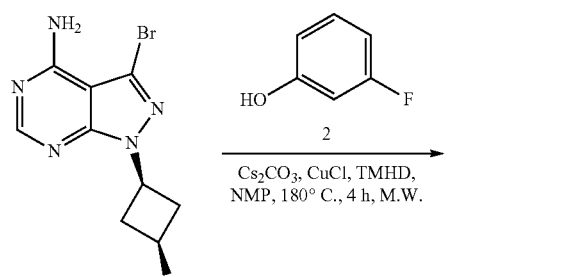

Three reactions were carried out in parallel. A mixture of 1 (0.2 g, 534.42 μmol, 1 eq), 2 (119.82 mg, 1.07 mmol, 98.21

To a mixture of 1-((cis)-3-(benzyloxy)cyclobutyl)-3-(3-fluorophenoxy)-1H-pyrazolo[3,4-d]pyrimidin-4-amine (3) (95 mg, 183 mol, 1 eq, TFA) in DCM (3 mL) was added BCl$_3$ (1 M, 1.83 mL, 10 eq) dropwise at −60° C. The mixture was slowly warmed to 0° C. and stirred for about 1 h. The reaction mixture was quenched by addition of 2 mL of methanol at −60° C., then purified by prep-HPLC (TFA condition) to give (cis)-3-(4-amino-3-(3-fluorophenoxy)-1H-pyrazolo[3,4-d]pyrimidin-1-yl)cyclobutan-1-ol (4; Compound 150) (16.2 mg, 36.7 μmol, 20.1% yield, 97.3% purity, TFA) as a white solid. LCMS: (M+H)$^+$: 316.1, Rt: 2.184 min. LC/MS method: The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS). $^1$H NMR: (400 MHz, ACETONITRILE-d$_3$) δ=10.91 (s, 1H), 8.21 (s, 1H), 7.48-7.46 (m, 1H), 7.26-7.23 (m, 2H), 7.04 (t, J=7.6 Hz, 1H), 4.81-4.78 (m, 1H), 4.10-4.03 (m, 1H), 2.76-2.73 (m, 2H), 2.44-2.41 (m, 2H).

Trans-3-fluorocyclobutyl analogs were produced from (cis)-3-hydroxycyclobutyl compound 4 in Synthesis Method Q in an analogous manner as described in Synthesis Method L, by protecting the amino group with Boc (Boc₂O, LiHMDS), fluorinating with DAST and then deprotection of the amino group.

TABLE 15

Compounds Prepared by Method Q

| Compound No. | IUPAC Name | Expected MW (M) | LC/MS Observed (M + H) | 1H NMR (400 MHz) |
|---|---|---|---|---|
| 151 | (cis)-3-(4-amino-3-(3-(trifluoromethyl)phenoxy)-1H-pyrazolo[3,4-d]pyrimidin-1-yl)cyclobutan-1-ol | 365.1 | 366.1 | 1H NMR (400MHz, METHANOL-d4) δ = 8.29 (s, 1H), 7.79-7.73 (m, 2H), 7.67 (t, J = 8.0 Hz, 1H), 7.61-7.57 (m, 1H), 4.94-4.89 (m, 1H), 4.15-4.07 (m, 1H), 2.81-2.73 (m, 2H), 2.53-2.50 (m, 2H) |
| 152 | (cis)-3-(4-amino-3-(3-chlorophenoxy)-1H-pyrazolo[3,4-d]pyrimidin-1-yl)cyclobutan-1-ol | 331 | 332.1 | 1H NMR (400MHz, ACETONITRILE-d3) δ = 10.58 (s, 1H), 8.22 (s, 1H), 7.50-7.48 (m, 1H), 7.46 (d, J= 8.0 Hz, 1H), 7.39 (d, J = 7.2 Hz, 1H), 7.32 (d, J = 8.0 Hz, 1H), 7.16 (s, 1H), 4.87-4.79 (m, 1H), 4.12-4.04 (m, 1H), 2.77-2.74 (m, 2H), 2.45-2.42 (m, 2H) |
| 153 | (cis)-3-(4-amino-3-(3-fluorophenoxy)-1H-pyrazolo[3,4-d]pyrimidin-1-yl)cyclobutan-1-ol | 315.1 | 316.1 | 1H NMR (400MHz, ACETONITRILE-d3) δ = 10.91 (s, 1H), 8.21 (s, 1H), 7.48-7.46 (m, 1H), 7.26-7.23 (m, 2H), 7.04 (t, J = 7.6 Hz, 1H), 4.81-4.78 (m, 1H), 4.10-4.03 (m, 1H), 2.76-2.73 (m, 2H), 2.44-2.41 (m, 2H) |

Synthesis Method R: Synthetic Route for the Preparation of (trans)-3-(4-amino-3-((5-fluoro-H-indol-3-yl)(hydroxy)methyl)-1H-pyrazolo[3,4-d]pyrimidin-1-yl)cyclobutan-1-ol (7)

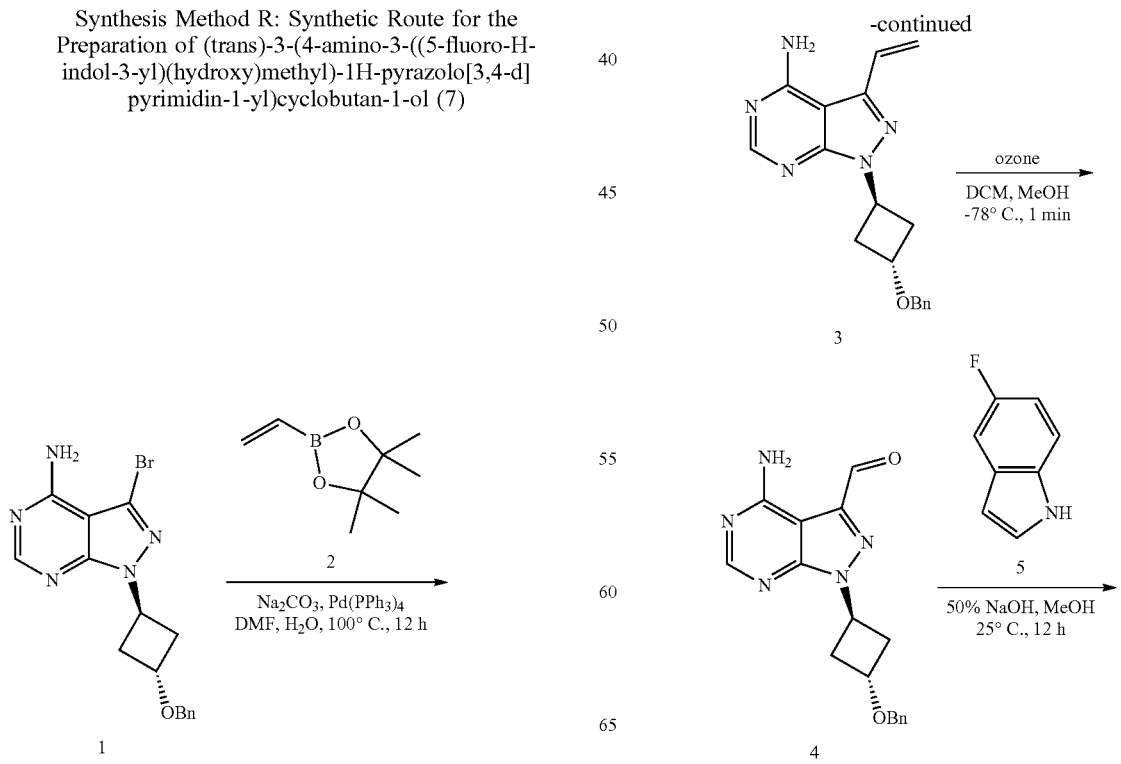

-continued

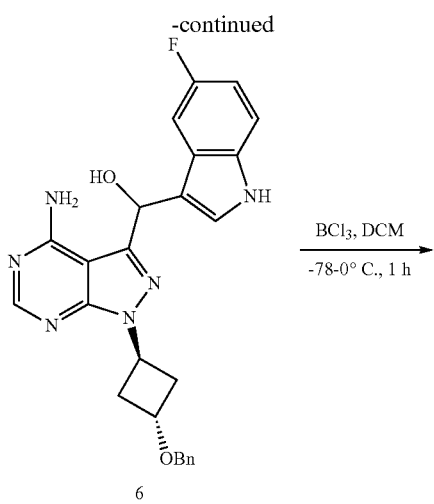

Step 1. Procedure for Preparation of 1-((trans)-3-(benzyloxy)cyclobutyl)-3-vinyl-1H-pyrazolo[3,4-d]pyrimidin-4-amine (3)

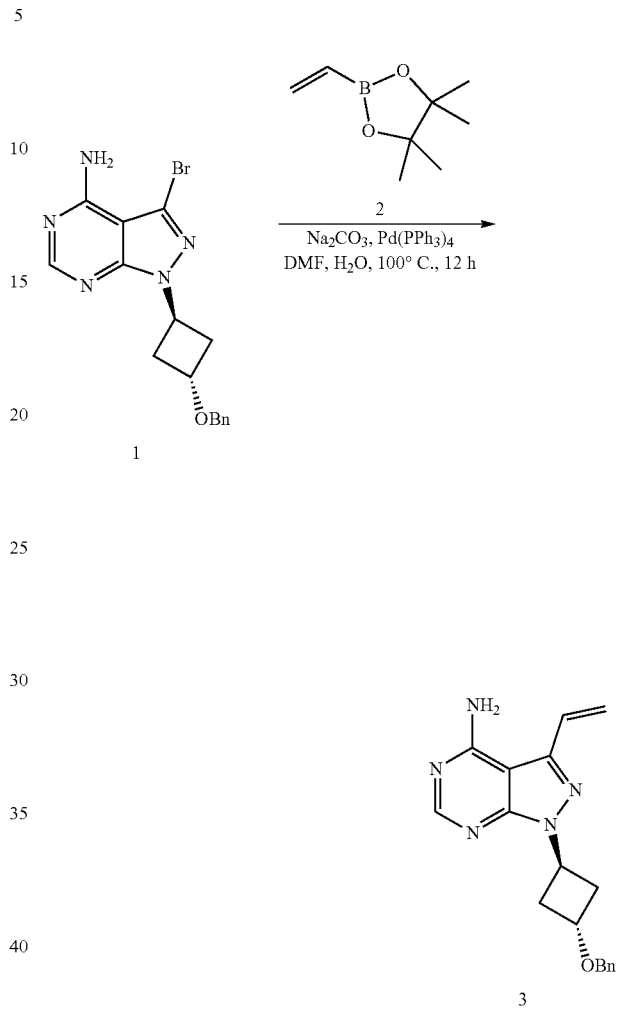

Two round-bottom flasks were each charged with 1-((trans)-3-(benzyloxy)cyclobutyl)-3-bromo-1H-pyrazolo[3,4-d]pyrimidin-4-amine (1) (1.25 g, 3.34 mmol, 1 eq), 4,4,5,5-tetramethyl-2-vinyl-1,3,2-dioxaborolane (2) (1.03 g, 6.68 mmol, 1.13 mL, 2 eq), Na$_2$CO$_3$ (708 mg, 6.68 mmol, 2 eq), H$_2$O (5 mL) and DMF (15 mL). Each flask was filled with N$_2$ and evacuated (3×), and then N$_2$ gas was bubbled through the mixture for about 5 minutes. Pd(PPh$_3$)$_4$ (193 mg, 167 µmol, 0.05 eq) was added to both mixtures, and the flasks were maintained under N$_2$. The mixtures were heated to about 100° C. for about 12 h. Both batches were combined and filtered through celite and the filtrate was partitioned between ethyl acetate (50 mL) and water (100 mL), and then the aqueous phase was further extracted with ethyl acetate (3×50 mL). The combined organic layers were washed with brine (200 mL), dried over Na$_2$SO$_4$, filtered and concentrated under reduced pressure to give a residue. The residue was purified by column chromatography (SiO$_2$, Petroleum ether/Ethyl acetate=3/1) to afford 1-((1r,3r)-3-(benzyloxy)cyclobutyl)-3-vinyl-1H-pyrazolo[3,4-d]pyrimidin-4-amine (3) (2.1 g, 5.55 mmol, 83.1% yield, 85% purity) as a yellow solid.

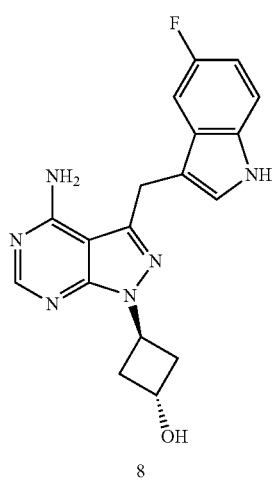

Step 2. Procedure for Preparation of 4-amino-1-((trans)-3-(benzyloxy)cyclobutyl)-1H-pyrazolo[3,4-d]pyrimidine-3-carbaldehyde (4)

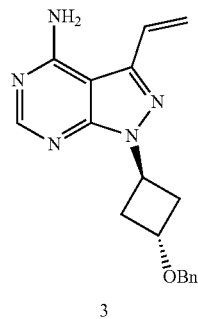

ozone
DCM, MeOH,
-78° C., 1 min

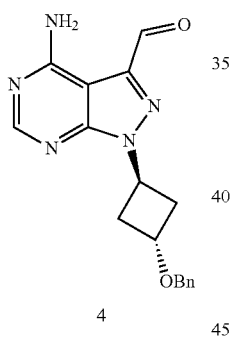

Ozone was bubbled into a solution of 1-((1r,3r)-3-(benzyloxy)cyclobutyl)-3-vinyl-1H-pyrazolo[3,4-d]pyrimidin-4-amine (3) (500 mg, 1.56 mmol, 1 eq) in DCM (10 mL) and MeOH (10 mL) at −78° C. for 1 min. After excess $O_3$ was purged with $O_2$, $Me_2S$ (4.23 g, 68.08 mmol, 5.00 mL, 43.76 eq) was added at −78° C. and warmed to 25° C. and stirred at 25° C. for 12 h. The 3 batches were combined together and the mixture was concentrated under reduced pressure to give a residue which was purified by column chromatography ($SiO_2$, Petroleum ether/Ethyl acetate=3/1) to give 4-amino-1-((trans)-3-(benzyloxy)cyclobutyl)-1H-pyrazolo[3,4-d]pyrimidine-3-carbaldehyde (4) (800 mg, 2.38 mmol, 50.9% yield, 96% purity) as a yellow solid. $^1$H NMR: (400 MHz, DMSO-$d_6$) δ=10.00 (s, 1H), 8.31 (s, 1H), 8.26 (s, 1H), 7.50 (s, 1H), 7.40-7.36 (m, 4H), 7.34-7.28 (m, 1H), 5.51 (m, 1H), 4.54-4.46 (m, 3H), 2.87-2.76 (m, 2H), 2.72-2.60 (m, 3H).

Step 3. Procedure for Preparation of (4-amino-1-((trans)-3-(benzyloxy)cyclobutyl)-1H-pyrazolo[3,4-d]pyrimidin-3-yl)(5-fluoro-1H-indol-3-yl)methanol (6)

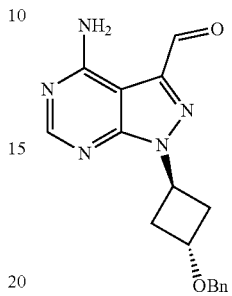

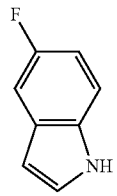

5
50% NaOH, MeOH,
25° C., 12 h

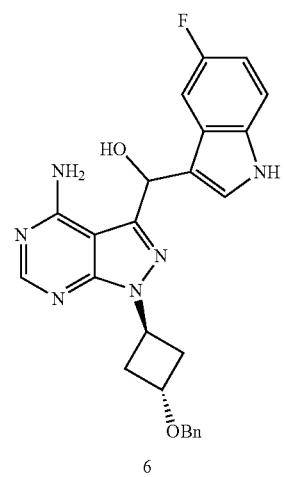

To a solution of 4-amino-1-((trans)-3-(benzyloxy)cyclobutyl)-1H-pyrazolo[3,4-d]pyrimidine-3-carbaldehyde (4) (400 mg, 1.24 mmol, 1 eq) and 5-fluoro-1H-indole (5) (167 mg, 1.24 mmol, 1 eq) in MeOH (20 mL) was added NaOH (247 mg, 3.09 mmol, 50% purity, 2.5 eq) in one portion at 25° C. for 12 h. The mixture was filtered and the filtrate was concentrated under reduced pressure to give a residue that was purified by column chromatography ($SiO_2$, Petroleum ether/EtOAc: going from 50/1 to 0/1) to give (4-amino-1-((trans)-3-(benzyloxy)cyclobutyl)-1H-pyrazolo[3,4-d]pyrimidin-3-yl)(5-fluoro-1H-indol-3-yl)methanol (6) (260 mg, 329 μmol, 13.3% yield) as a green solid.

Step 4. Procedure for Preparation of (trans)-3-(4-amino-3-((5-fluoro-1H-indol-3-yl)(hydroxy)methyl)-1H-pyrazolo[3,4-d]pyrimidin-1-yl)cyclobutan-1-ol

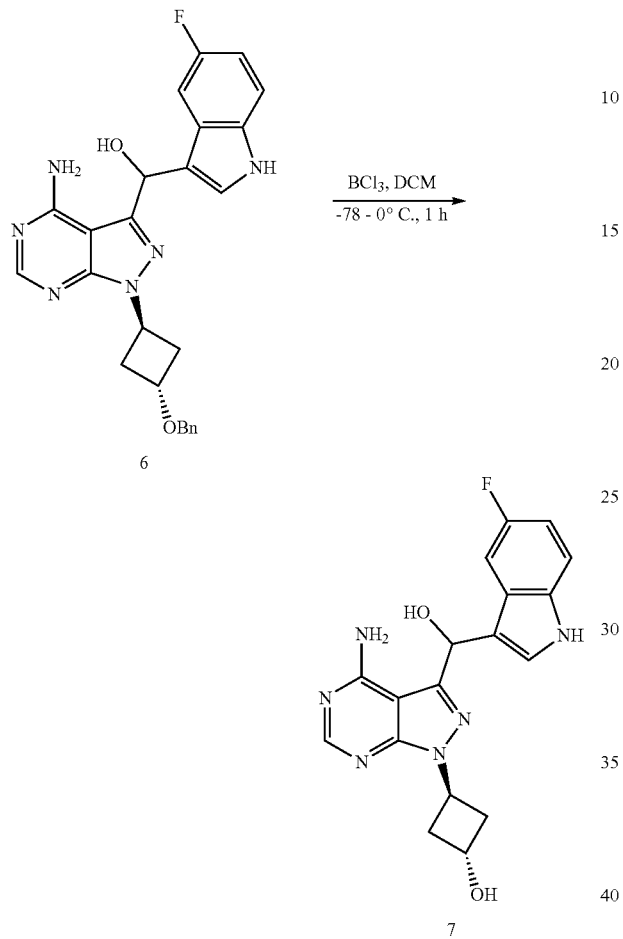

To a solution of (4-amino-1-((trans)-3-(benzyloxy)cyclobutyl)-1H-pyrazolo[3,4-d]pyrimidin-3-yl)(5-fluoro-1H-indol-3-yl)methanol (6) (50 mg, 109 µmol, 1 eq) in DCM (2 mL) was added BCl₃ (1 M, 1.09 mL, 10 eq) drop-wise at −78° C. and then warmed to 0° C. and stirred at 0° C. for 1 h. The reaction was quenched by addition of 2 mL of saturated NaHCO₃ at 0° C., and then the resulting mixture was extracted with DCM (3×3 mL). The organic phase was washed with brine (3 mL) and dried over Na₂SO₄, filtered and concentrated under reduced pressure to a residue that was purified by prep-HPLC (neutral condition) to give (trans)-3-(4-amino-3-((5-fluoro-1H-indol-3-yl)(hydroxy)methyl)-1H-pyrazolo[3,4-d]pyrimidin-1-yl)cyclobutan-1-ol (1 mg, 2.70 µmol, 2.48% yield, 99.6% purity) as a yellow solid. LCMS: (M+H)⁺: 369.1, Rt: 2.187 min. (The gradient was 5-90% B in 3.4 min, 90-100% B in 0.45 min, 100-5% B in 0.01 min, and then held at 5% B for 0.65 min (0.8 mL/min flow rate). Mobile phase A was 10 mM NH₄HCO₃, mobile phase B was HPLC grade CH₃CN. The column used for the chromatography is a 2.1×50 mm Xbridge Shield RPC18 column (5 µm particles). Detection methods are diode array (DAD) and evaporative light scattering (ELSD) detection as well as positive electrospray ionization (MS). ¹H NMR: (400 MHz, ACETONITRILE-d₃) δ=9.35 (s, 1H), 8.16 (s, 1H), 7.40-7.31 (m, 2H), 7.16 (d, J=2.0 Hz, 1H), 6.91 (dt, J=2.4, 9.2 Hz, 1H), 6.35 (s, 1H), 5.47-5.38 (m, 1H), 4.85 (s, 1H), 4.70-4.61 (m, 1H), 3.35 (d, J=5.2 Hz, 1H), 2.87-2.71 (m, 2H), 2.50-2.40 (m, 2H).

Step 5. Procedure for Preparation of (trans)-3-(4-amino-3-((5-fluoro-1H-indol-3-yl)methyl)-1H-pyrazolo[3,4-d]pyrimidin-1-yl)cyclobutan-1-ol

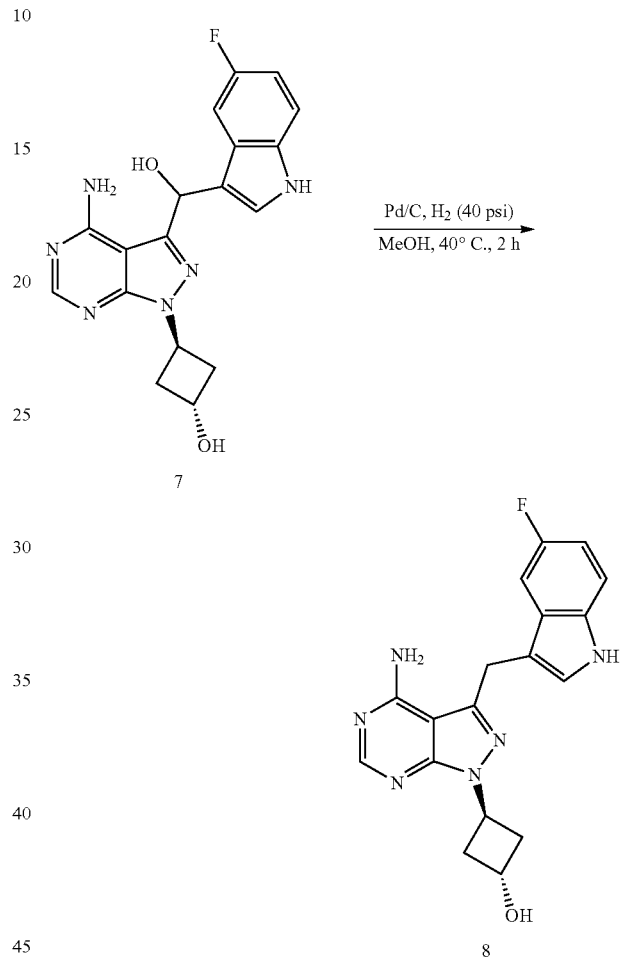

To a solution of (4-amino-1-((trans)-3-(benzyloxy)cyclobutyl)-1H-pyrazolo[3,4-d]pyrimidin-3-yl)(5-fluoro-1H-indol-3-yl)methanol (7) (50 mg, 109 µmol, 1 eq) in MeOH (10 mL) was added Pd/C (100 mg) under argon atmosphere. The suspension was degassed and purged with H₂ for 3 times. The mixture was stirred under H₂ (40 Psi) at 40° C. for 2 h. The two batches of mixture were cooled to 25° C., combined and filtered through celite. The filtrate was concentrated under reduced pressure and the residue purified by prep-HPLC (neutral conditions) to give (trans)-3-(4-amino-3-((5-fluoro-1H-indol-3-yl)methyl)-1H-pyrazolo[3,4-d]pyrimidin-1-yl)cyclobutan-1-ol (8; Compound 154) (16.8 mg, 47.6 µmol, 21.8% yield, 99.8% purity) as a white solid. LCMS: (M+H)⁺: 353.1, Rt: 2.344 min. LC/MS Method: The gradient was 5-90% B in 3.4 min, 90-100% B in 0.45 min, 100-5% B in 0.01 min, and then held at 5% B for 0.65 min (0.8 mL/min flow rate. Mobile phase A was 10 mM NH₄HCO₃, mobile phase B was HPLC grade CH₃CN. The column used for the chromatography is a 2.1×50 mm Xbridge Shield RPC18 column (5 µm particles). Detection methods are diode array (DAD) and evaporative light scattering (ELSD) detection as well as positive electrospray ionization (MS). $^1$H NMR: (400 MHz, ACETONITRILE-$d_3$) δ=9.27 (s, 1H), 8.12 (s, 1H), 7.40-7.36 (m, 1H), 7.20 (s, 1H), 7.15 (d, J=10.4 Hz, 1H), 6.92 (t, J=9.2 Hz, 1H), 5.59 (s, 2H); 5.46-5.42 (m, 1H), 4.70-4.67 (m, 1H), 4.36 (s, 2H), 3.27 (s, 1H), 2.87-2.82 (m, 2H), 2.50-2.46 (m, 2H).

Synthesis Method S: General Procedure Represented by the Preparation of 3-[4-amino-5-[(3-fluorophenyl)methyl]pyrrolo[2,3-d]pyrimidin-7-yl]cyclobutanol (6)

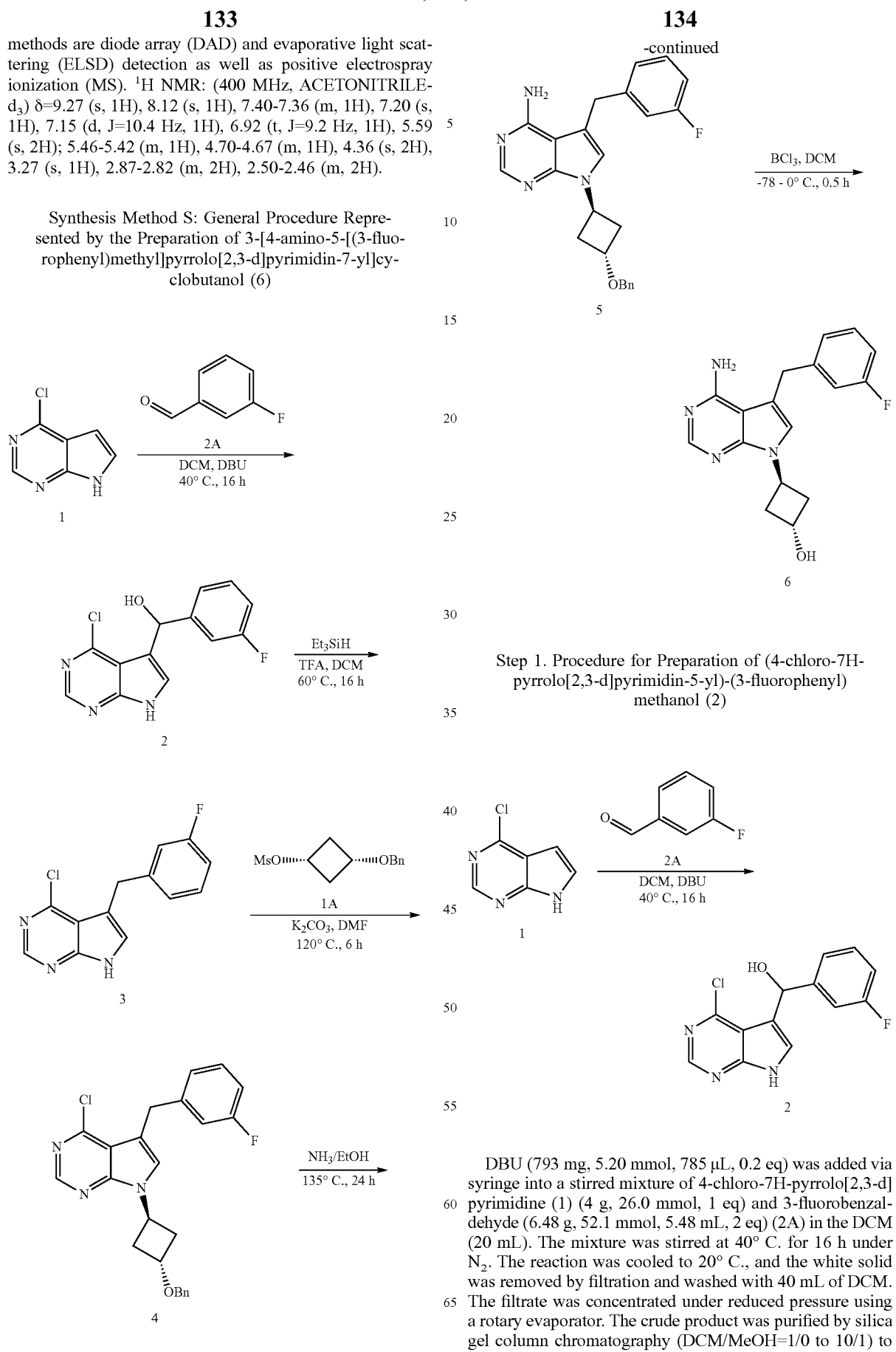

Step 1. Procedure for Preparation of (4-chloro-7H-pyrrolo[2,3-d]pyrimidin-5-yl)-(3-fluorophenyl)methanol (2)

DBU (793 mg, 5.20 mmol, 785 µL, 0.2 eq) was added via syringe into a stirred mixture of 4-chloro-7H-pyrrolo[2,3-d]pyrimidine (1) (4 g, 26.0 mmol, 1 eq) and 3-fluorobenzaldehyde (6.48 g, 52.1 mmol, 5.48 mL, 2 eq) (2A) in the DCM (20 mL). The mixture was stirred at 40° C. for 16 h under $N_2$. The reaction was cooled to 20° C., and the white solid was removed by filtration and washed with 40 mL of DCM. The filtrate was concentrated under reduced pressure using a rotary evaporator. The crude product was purified by silica gel column chromatography (DCM/MeOH=1/0 to 10/1) to afford (4-chloro-7H-pyrrolo[2,3-d]pyrimidin-5-yl)-(3-fluorophenyl)methanol (2) (1.2 g, 4.32 mmol, 16.6% yield) as a yellow solid.

Step 2. Procedure for Preparation of 4-chloro-5-[(3-fluorophenyl)methyl]-7H-pyrrolo[2,3-d]pyrimidine (3)

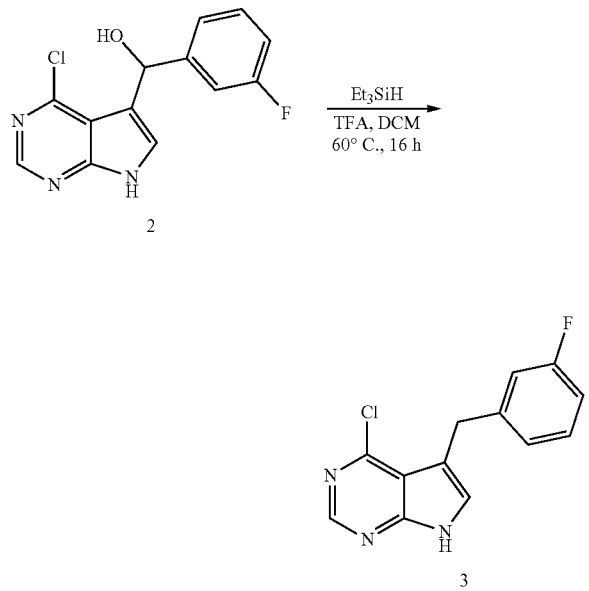

A suspension of (4-chloro-7H-pyrrolo[2,3-d]pyrimidin-5-yl)-(3-fluorophenyl)methanol (500 mg, 1.80 mmol, 1 eq) (2) in DCM (5 mL) was treated sequentially with triethylsilane (628 mg, 5.40 mmol, 863 µL, 3 eq) and TFA (411 mg, 3.60 mmol, 267 µL, 2 eq) and stirred at 60° C. for 16 h. The reaction was quenched by addition of 10 mL of water, and then extracted by diethyl ether (3×10 mL). The organic phase was concentrated and the crude product was purified by silica gel column chromatography (DCM/MeOH=I/O to 10/1) to afford 4-chloro-5-[(3-fluorophenyl)methyl]-7H-pyrrolo[2,3-d]pyrimidine (3) (300 mg, 1.15 mmol, 63.67% yield) as a white solid.

Step 3. Procedure for Preparation of 7-(3-benzyloxycyclobutyl)-4-chloro-5-[(3-fluorophenyl)methyl]pyrrolo[2,3-d]pyrimidine (4)

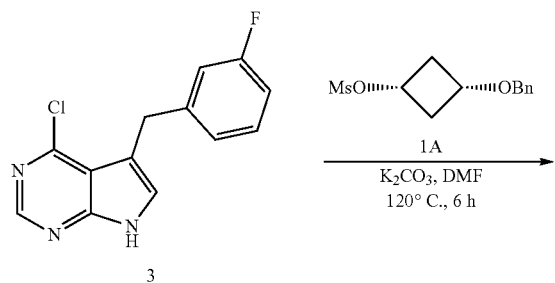

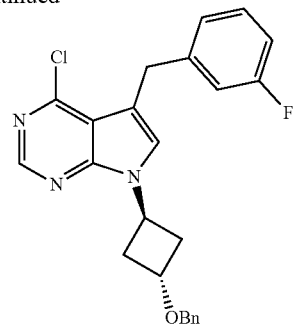

A mixture of 4-chloro-5-[(3-fluorophenyl)methyl]-7H-pyrrolo[2,3-d]pyrimidine (250 mg, 955 µmol, 1 eq) (3), $K_2CO_3$ (264 mg, 1.91 mmol, 2 eq) and (3-benzyloxycyclobutyl) methanesulfonate (416 mg, 1.62 mmol, 1.7 eq) (1A) in DMF (5 mL) was stirred at 120° C. for 6 h. The reaction was quenched by addition of 10 mL of water, and then extracted by EtOAc (3×5 mL). The crude product was purified by silica gel column chromatography (DCM/MeOH=1/0 to 10/1) to afford 7-(3-benzyloxycyclobutyl)-4-chloro-5-[(3-fluorophenyl)methyl]pyrrolo[2,3-d]pyrimidine (4) (100 mg, 237 µmol, 24.8% yield) as a yellow solid.

Step 4. Procedure for Preparation of 7-(3-benzyloxycyclobutyl)-5-[(3-fluorophenyl)methyl]pyrrolo[2,3-d]pyrimidin-4-amine (5)

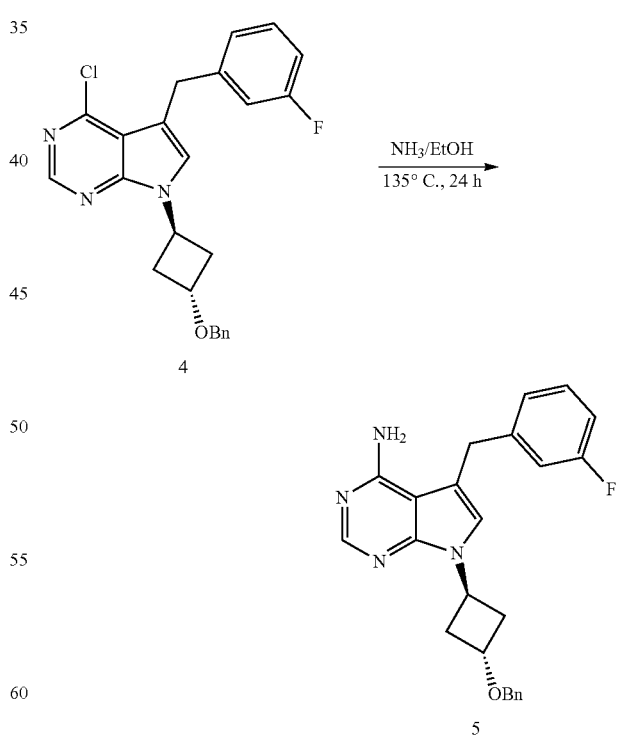

A solution of 7-(3-benzyloxycyclobutyl)-4-chloro-5-[(3-fluorophenyl)methyl]-pyrrolo[2,3-d]pyrimidine (100 mg, 237 µmol, 1 eq) (4) in $NH_3$/EtOH (4 M, 150 mL, 2531 eq) was stirred at 135° C. for 24 h in a sealed tube. The reaction mixture was concentrated under reduced pressure using a rotary evaporator. The crude product was purified by prep-TLC (DCM/MeOH—10/1) to afford 7-(3-benzyloxycyclobutyl)-5-[(3-fluorophenyl)methyl]pyrrolo[2,3-d]pyrimidin-4-amine (5) (50 mg, 124 μmol, 52.4% yield) as a white solid.

Step 5. Procedure for Preparation of 3-[4-amino-5-[(3-fluorophenyl)methyl]pyrrolo[2,3-d]pyrimidin-7-yl]cyclobutanol (6)

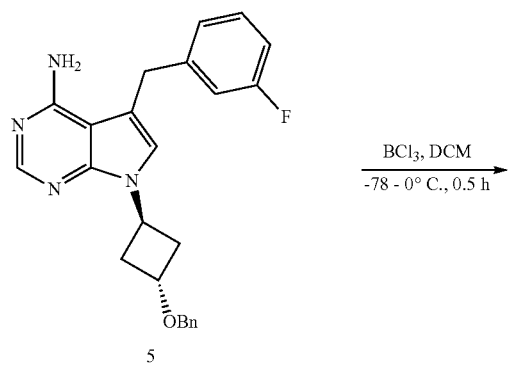

BCl₃ (1 M, 1.24 mL, 10 eq) was added dropwise to a stirred mixture of 7-(3-benzyloxycyclobutyl)-5-[(3-fluorophenyl)methyl]pyrrolo[2,3-d]pyrimidin-4-amine (5) (50 mg, 124 μmol, 1 eq) in DCM (2 mL) at −78° C. under N₂. The mixture was stirred at 0° C. for 0.5 h. The reaction was quenched by addition of 5 mL of MeOH at −78° C., and then stirred for 2 min. The mixture was basified by slowly adding ammonium hydrooxide at 0° C. to pH=8, filtered, and the filtrate was concentrated and the residue was purified by prep-HPLC (TFA condition) to give 3-[4-amino-5-[(3-fluorophenyl)methyl]pyrrolo[2,3-d]pyrimidin-7-yl]cyclobutanol (6) (15.3 mg, 35.5 μmol, 28.6% yield, 99% purity, TFA) as a white solid.

¹H NMR: (400 MHz, acetonitrile-d₃) δ=8.11 (s, 1H), 7.36-7.32 (m, 1H), 7.26 (s, 1H), 7.08 (d, J=7.6 Hz, 1H), 7.00-6.95 (m, 2H), 5.43-5.35 (m, 1H), 4.55-4.50 (m, 1H), 4.19 (s, 2H), 2.70-2.64 (m, 2H), 2.51-2.48 (m, 2H).

Synthesis Method T: General Procedure Represented by the Preparation of 2-(4-amino-1-cyclopropyl-pyrazolo[3,4-d]pyrimidin-3-yl)oxypyridin-4-ol (3)

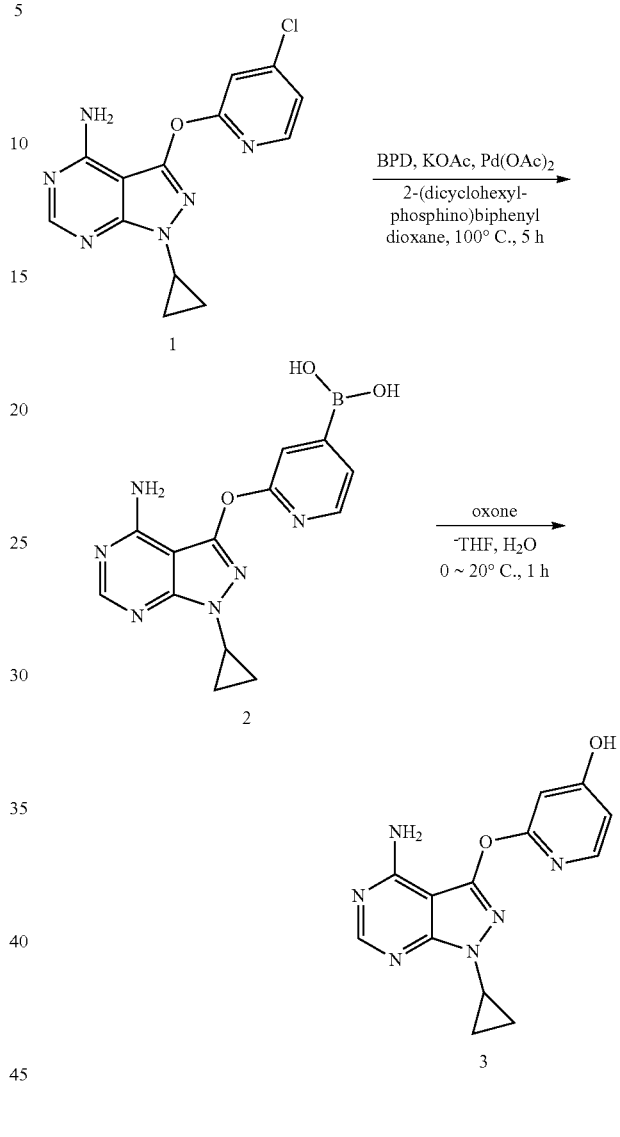

Step 1. Procedure for Preparation of [2-(4-amino-1-cyclopropyl-pyrazolo[3,4-d]pyrimidin-3-yloxy-4-pyridyl]boronic Acid (2)

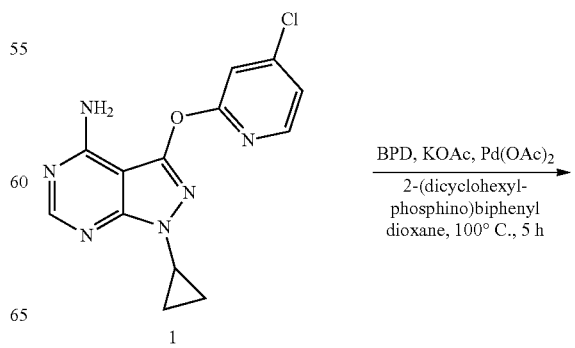

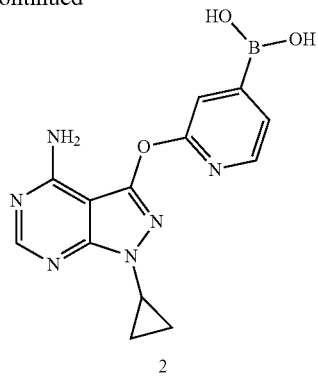

Pd(OAc)₂ (37.1 mg, 165 µmol, 0.05 eq) was added into a stirred mixture of 3-[(4-chloro-2-pyridyl)oxy]-1-cyclopropyl-pyrazolo[3,4-d]pyrimidin-4-amine (1) (1 g, 3.30 mmol, 1 eq), BPD (1.68 g, 6.61 mmol, 2 eq), KOAc (973 mg, 9.91 mmol, 3 eq) and dicyclohexyl-(2-phenylphenyl)phosphane (57.9 mg, 165 µmol, 0.05 eq) in dioxane (10 mL). The mixture was stirred at 100° C. for 5 h, quenched by addition of 20 mL of water, and the yellow solid was collected by filtration, washed with three portions (5 mL each) of water and dried under reduced pressure using a rotary evaporator to give [2-(4-amino-1-cyclopropyl-pyrazolo[3,4-d]pyrimidin-3-yl)oxy-4-pyridyl]boronic acid (2) (2 g, crude) as a yellow solid.

¹H NMR: (400 MHz, DMSO-d₆) δ=8.62 (s, 1H), 8.27 (s, 1H), 8.11 (d, J=5.6 Hz, 1H), 7.50-7.47 (m, 2H), 3.74-3.68 (m, 1H), 1.07-0.99 (m, 4H)

Step 2. Procedure for Preparation of 2-(4-amino-1-cyclopropyl-pyrazolo[3,4-d]pyrimidin-3-yl)oxypyridin-4-ol (1.5 g, crude) (3)

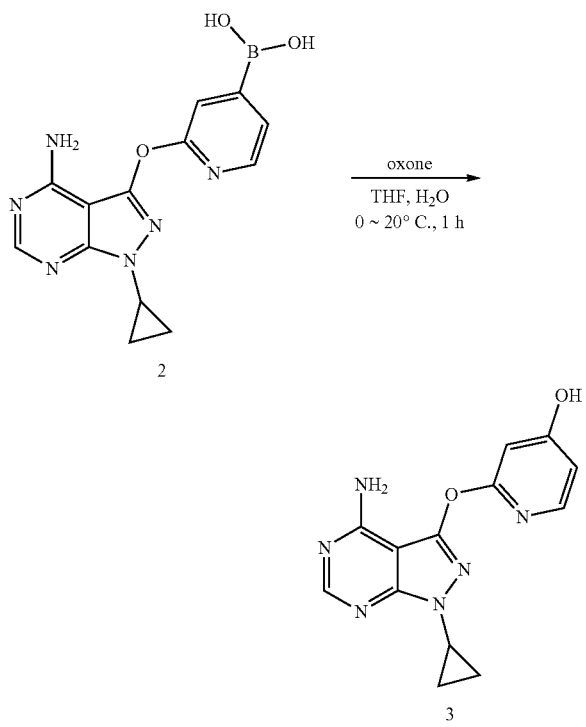

A solution of oxone (3.27 g, 5.33 mmol, 1.05 eq) in water (20 mL) was added to a stirred mixture of [2-(4-amino-1-cyclopropyl-pyrazolo[3,4-d]pyrimidin-3-yl)oxy-4-pyridyl]boronic acid (2 g, 6.41 mmol, 1 eq) in THF (20 mL) at 0° C. The mixture was stirred at 20° C. for 1 h and quenched by addition of 20 mL of saturation sodium sulfite. The white solid was collected by filtration, washed with three portions (10 mL each) of water and dried under reduced pressure using a rotary evaporator to give 2-(4-amino-1-cyclopropyl-pyrazolo[3,4-d]pyrimidin-3-yl)oxypyridin-4-ol (1.5 g, crude) as a white solid. A 200 mg portion of the crude product was purified by prep-HPLC (TFA condition) to give 5 mg of 2-(4-amino-1-cyclopropyl-pyrazolo[3,4-d]pyrimidin-3-yl)oxypyridin-4-ol (100% LCMS purity, TFA) as a white solid.

¹H NMR: (400 MHz, methanol-d₄) δ=8.34 (s, 1H), 7.96 (d, J=5.6 Hz, 1H), 6.89 (d, J=2.0 Hz, 1H), 6.73 (dd, J=2.0, 6.0 Hz, 1H), 3.85 (tt, J=3.6, 7.2 Hz, 1H), 1.30-1.20 (m, 2H), 1.20-1.09 (m, 2H).

Synthesis Method U: General Procedure Represented by the Preparation of 1-cyclopropyl-3-[(4-cyclopropyl-2-pyridyl)oxy]pyrazolo[3,4-d]pyrimidin-4-amine

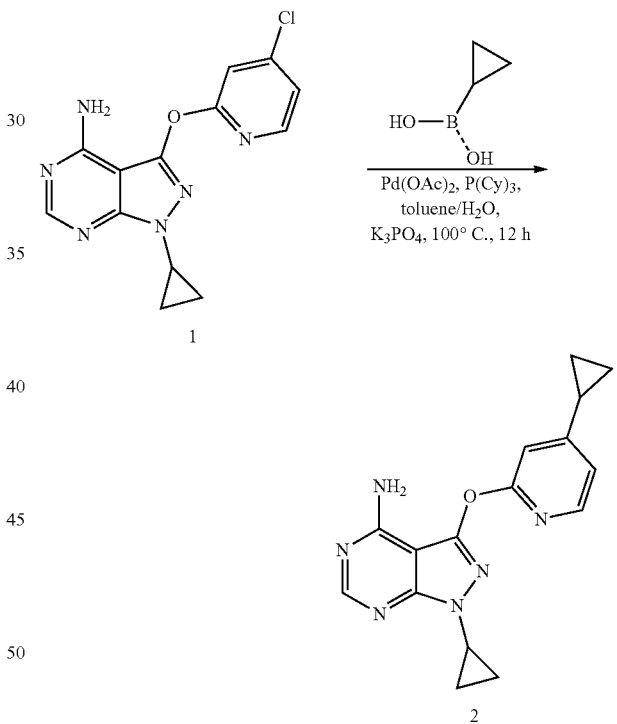

A mixture of 3-[(4-chloro-2-pyridyl)oxy]-1-cyclopropyl-pyrazolo[3,4-d]pyrimidin-4-amine (1) (80 mg, 264 µmol, 1 eq), cyclopropylboronic acid (45.4 mg, 529 µmol, 2 eq), Pd(OAc)₂ (1.19 mg, 5.29 µmol, 0.02 eq), K₃PO₄ (196 mg, 925 µmol, 3.5 eq), P(Cy)₃ (7.41 mg, 26.4 µmol, 8.57 µL, 0.1 eq) in H₂O (0.2 mL) and toluene (4 mL) was degassed and purged with N₂ for 3 times, and then stirred at 100° C. for 12 h under N₂ atmosphere. The mixture was filtered and the filtrate was concentrated under reduced pressure and the residue was purified by prep-HPLC (TFA condition) to give 1-cyclopropyl-3-[(4-cyclopropyl-2-pyridyl)oxy]pyrazolo[3,4-d]pyrimidin-4-amine (2) (6 mg, 18.9 µmol, 7.14% yield, 97% purity) as a white solid. LCMS: (M+H)⁺: 309.1, Rt:

4.548 min. ¹H NMR: (400 MHz, MeOD-d₄) δ=8.31 (s, 1H), 8.01 (d, J=5.2 Hz, 1H), 7.13 (s, 1H), 6.98 (d, J=4.0 Hz, 1H), 3.83-3.77 (m, 1H), 2.10-2.01 (m, 1H), 1.22-1.19 (m, 4H), 1.18-1.17 (m, 2H), 0.92-0.89 (m, 2H).

Additional Compounds of the Invention: The following compounds may be prepared according to the methods described herein.

TABLE 16

Further Compounds of the Invention

| Compound No. | IUPAC Name | Expected MW (M) | LC/MS Observed (M + H) | ¹H NMR (400 MHz) |
|---|---|---|---|---|
| 156 | 3-(3-chlorophenoxy)-1-[(trans)-3-fluorocyclobutyl]-1H-pyrazolo[3,4-d]pyrimidin-4-amine | 333.74 | 334 | (Methanol-d₄) δ = 8.18 (s, 1H), 7.47 (t, J = 2.0 Hz, 1H), 7.44-7.39 (m, 1H), 7.36-7.32 (m, 1H), 7.24 (dd, J = 1.2, 8.0 Hz, 1H), 5.53-5.45 (m, 1H), 5.40-5.38 (m, 0.5H), 5.28-5.23 (m, 0.5H), 2.89-2.70 (m, 4H) |
| 157 | 3-[(5-fluoroindol-3-yl)methyl]-1-[(trans)-3-fluorocyclobutyl]-1H-pyrazolo[3,4-d]pyrimidin-4-amine | 353.35 | 355.1 | (Acetonitrile-d₃) δ = 9.29 (s, 1H), 8.14 (s, 1H), 7.38 (dd, J = 4.4, 8.8 Hz, 1H), 7.20 (d, J = 2.4 Hz, 1H), 7.15 (dd, J = 2.8, 7.6 Hz, 1H), 6.92 (dt, J = 2.4, 9.2 Hz, 1H), 5.71-5.45 (m, 4H), 4.36 (s, 2H), 3.00-2.76 (m, 4H) |
| 158 | 3-[(4-chloropyridin-2-yl)oxy]-1-[(trans)-3-fluorocyclobutyl]-1H-pyrazolo[3,4-d]pyrimidin-4-amine | 334.74 | 335.1 | (DMSO-d₆) δ = 8.19 (s, 1H), 8.12 (d, J = 5.6 Hz, 1H), 7.41 (d, J = 1.6 Hz, 1H), 7.34 (dd, J = 1.6, 5.6 Hz, 1H), 5.50-5.45 (m, 1.5H), 5.35-5.31 (m, 0.5H), 2.82-2.67 (m, 4H) |
| 159 | 1-cyclopropyl-3-{[4-(trifluoromethyl)pyridin-2-yl]oxy}-1H-pyrazolo[3,4-d]pyrimidin-4-amine | 336.27 | 337 | (Methanol-d₄) δ = 8.41 (d, J = 5.2 Hz, 1H), 8.34 (s, 1H), 7.68 (s, 1H), 7.54 (d, J = 5.2 Hz, 1H), 3.88-3.83 (m, 1H), 1.26-1.20 (m, 2H), 1.14-1.13 (m, 2H) |
| 160 | 2-({4-amino-1-cyclopropyl-1H-pyrazolo[3,4-d]pyrimidin-3-yl}oxy)pyridin-4-ol | 284.27 | 285.1 | (Methanol-d₄) δ = 8.34 (s, 1H), 7.96 (d, J = 5.6 Hz, 1H), 6.89 (d, J = 2.0 Hz, 1H), 6.74-6.72 (m, 1H), 3.88-3.82 (m, 1H), 1.28-1.25 (m, 2H), 1.16-1.12 (m, 2H) |
| 161 | 3-[(3-fluorophenyl)methyl]-1-[(trans)-3-fluorocyclobutyl]-1H-pyrazolo[3,4-d]pyrimidin-4-amine | 315.32 | 316.2 | (Methanol-d₄) δ = .8.31 (s, 1H), 7.37-7.32 (m, 1H), 7.09 (d, J = 7.6 Hz, 1H), 7.05-6.98 (m, 2H), 5.68-5.62 (m, 1H), 5.55-5.53 (m, 0.5H), 5.40-5.39 (m, 0.5H), 4.48 (s, 2H), 3.00-2.85 (m, 4H) |
| 162 | 3-[(4-methoxypyridin-2-yl)oxy]-1-[(trans)-3-fluorocyclobutyl]-1H-pyrazolo[3,4-d]pyrimidin-4-amine | 330.32 | 331 | (Methanol-d₄) δ = 8.32 (s, 1H), 8.04 (d, J = 6.0 Hz, 1H), 7.04 (d, J = 2.0 Hz, 1H), 6.91-6.89 (m, 1H), 5.64-5.60 (m, 1H), 5.46-5.44 (m, 0.5H), 5.31-5.29 (m, 0.5H), 3.96 (s, 3H), 2.93-2.79 (m, 4H) |
| 163 | (cis)-3-{4-amino-3-[(4-chloropyridin-2-yl)oxy]-1H-pyrazolo[3,4-d]pyrimidin-1-yl}cyclobutan-1-ol | 332.75 | 333 | (DMSO-d₆ + D₂O) δ = 8.27 (s, 1H), 8.11 (d, J = 5.6 Hz, 1H), 7.43 (d, J = 1.6 Hz, 1H), 7.34 (dd, J = 1.6, 5.6 Hz, 1H), 4.83-4.75 (m, 1H), 4.03-3.95 (m, 1H), 2.71-2.67 (m, 2H), 2.41-2.33 (m, 2H) |

TABLE 16-continued

Further Compounds of the Invention

| Compound No. | IUPAC Name | Expected MW (M) | LC/MS Observed (M + H) | $^1$H NMR (400 MHz) |
|---|---|---|---|---|
| 164 | (trans)-3-{4-amino-5-[(3-fluorophenyl)methyl]-7H-pyrrolo[2,3-d]pyrimidin-7-yl}cyclobutan-1-ol | 312.34 | 313.1 | (Acetonitrile-d$_3$) δ = 8.11 (s, 1H), 7.36-7.32 (m, 1H), 7.26 (s, 1H), 7.08 (d, J = 7.6 Hz, 1H), 7.04-6.94 (m, 2H), 5.44-5.34 (m, 1H), 4.55-4.49 (m, 1H), 4.19 (s, 2H), 2.73-2.63 (m, 2H), 2.53-2.44 (m, 2H) |
| 165 | 1-cyclopropyl-3-[(4-cyclopropylpyridin-2-yl)oxy]-1H-pyrazolo[3,4-d]pyrimidin-4-amine | 308.34 | 309.1 | (Methanol-d$_4$) δ = 8.31 (s, 1H), 8.01 (d, J = 5.2 Hz, 1H), 7.13 (s, 1H), 6.98 (d, J = 4.0 Hz, 1H), 3.83-3.77 (m, 1H), 2.10-2.01 (m, 1H), 1.22-1.19 (m, 4H), 1.18-1.17 (m, 2H), 0.92-0.89 (m, 2H) |
| 166 | 1-[(trans)-3-fluorocyclobutyl]-3-[3-(trifluoromethyl)phenoxy]-1H-pyrazolo[3,4-d]pyrimidin-4-amine | 367.30 | 368.1 | (Methanol-d$_4$) δ = 8.18 (s, 1H), 7.80 (s, 1H), 7.72-7.68 (m, 1H), 7.66-7.61 (m, 1H), 7.56-7.51 (m, 1H), 5.49 (t, J = 7.2 Hz, 1H), 5.42-5.36 (m, 0.5H), 5.27-5.20 (m, 0.5H), 2.90-2.68 (m, 4H) |
| 167 | 3-(3-fluorophenoxy)-1-[(trans)-3-fluorocyclobutyl]-1H-pyrazolo[3,4-d]pyriniidin-4-amine | 317.29 | 318.1 | (Methanol-d$_4$) δ = 8.18 (s, 1H), 7.47-7.40 (m, 1H), 7.24-7.19 (m, 2H), 7.01-6.95 (m, 1H), 5.53-5.45 (m, 1H), 5.40-5.39 (m, 0.5H), 5.26-5.24 (m, 0.5H), 2.86-2.70 (m, 4H) |
| 168 | (cis)-3-{4-amino-3-[(4-methoxypyridin-2-yl)oxy]-1H-pyrazolo[3,4-d]pyrimidin-1-yl}cyclobutan-1-ol | 328.33 | 329.1 | (Methanol-d$_4$) δ = 8.17 (s, 1H), 8.01 (d, J = 6.0 Hz, 1H), 7.05 (d, J = 2.0 Hz, 1H), 6.84 (dd, J = 2.0, 6.0 Hz, 1H), 4.82-4.79 (m, 1H), 4.17-4.09 (m, 1H), 3.94 (s, 3H), 2.83-2.79 (m, 2H), 2.60-2.57 (m, 2H) |
| 169 | 1-cyclopropyl-3-{[4-(trifluoromethoxy)pyridin-2-yl]oxy}-1H-pyrazolo[3,4-d]pyrimidin-4-amine | 352.27 | 353.1 | (Methanol-d$_4$) δ = 8.25-8.22 (m, 2H), 7.32 (s, 1H), 7.16 (d, J = 5.6 Hz, 1H), 3.71-3.64 (m, 1H), 1.20-1.17 (m, 2H), 1.12-1.08 (m, 2H) |
| 170 | (cis)-3-(4-amino-3-([4-(trifluoromethyl)pyridin-2-yl]oxy}-1H-pyrazolo[3,4-d]pyrimidin-1-yl)cyclobutan-1-ol | 366.30 | 367.1 | (Methanol-d$_4$) δ = 8.42 (d, J = 5.2 Hz, 1H), 8.32 (s, 1H), 7.70 (s, 1H), 7.55 (d, J = 5.6 Hz, 1H), 5.00-4.92 (m, 1H), 4.18-4.11 (m, 1H), 2.86-2.81 (m, 2H), 2.58-2.55 (m, 2H) |
| 171 | 3-(3-chlorophenoxy)-1-[(trans)-3-fluorocyclobutyl]-1H-pyrazolo[3,4-d]pyrimidin-4-amine | 333.75 | 334 | (Methanol-d$_4$) δ = 8.18 (s, 1H), 7.47 (d, J = 2.0 Hz, 1H), 7.42-7.40 (m, 1H), 7.37 (d, /= 15.6 Hz, 1H), 7.23 (d, J = 8.4 Hz, 1H), 5.51-5 47 (m, 1H), 5.40-5.38 (m, 0.5H), 5.26-5.24 (m, 0.5H), 2.88-2.71 (m, 4H) |

TABLE 16-continued

Further Compounds of the Invention

| Compound No. | IUPAC Name | Expected MW (M) | LC/MS Observed (M + H) | ¹H NMR (400 MHz) |
|---|---|---|---|---|
| 172 | 3-({4-amino-1-[(trans)-3-fluorocyclobutyl]-1H-pyrazolo[3,4-d]pyrimidin-3-yl}methyl)benzonitrile | 322.34 | 323.1 | (Acetonitrile-d₃) δ = 8.23 (s, 1H), 7.65 (d, J = 7.6 Hz, 1H), 7.62-7.57 (m, 2H), 7.55-7.47 (m, 1H), 5.62-5.51 (m, 1.5H), 5.45-5.35 (m, 0.5H), 4.43 (s, 2H), 3.01-2.76 (m, 4H) |
| 173 | 3-({4-amino-1-[(trans)-3-fluorocyclobutyl]-1H-pyrazolo[3,4-d]pyrimidin-3-yl}oxy)benzonitrile | 324.31 | 325.1 | (Methanol-d₄) δ = 8.18 (s, 1H), 7.83 (s, 1H), 7.76 (dd, J = 2.4, 7.6 Hz, 1H), 7.65-7.60 (m, 2H), 5.51-5.47 (m, 1H), 5.39-5.37 (m, 0.5H), 5.25-5.22 (m, 0.5H), 2.88-2.71 (m, 4H) |
| 174 | 2-({4-amino-1-[(trans)-3-fluorocyclobutyl]-1H-pyrazolo[3,4-d]pyrimidin-3-yl}oxy)pyridine-4-carboxamide | 343.32 | 344.1 | (Methanol-d₄) δ = 8.34 (d, J = 5.6 Hz, 1H), 8.30 (s, 1H), 7.82 (s, 1H), 7.66 (dd, J = 1.2, 5.2 Hz, 1H), 5.66-5.58 (m, 1H), 5.47-5.41 (m, 0.5H), 5.33-5.27 (m, 0.5H), 2.98-2.80 (m, 4H) |
| 175 | 3-[(4-methoxypyridin-2-yl)oxy]-1-[(trans)-3-fluorocyclobutyl]-1H-pyrazolo[3,4-d]pyrimidin-4-amine | 330.32 | 331.1 | (Acetonitrile-d₃) δ = 8.22 (s, 1H), 7.95 (d, J = 6.4 Hz, 1H), 6.77-6.76 (m, 2H), 5.94 (br s, 2H), 5.55-5.48 (m, 1.5H), 5.43-5.34 (m, 0.5H), 3.90 (s, 3H), 2.91-2.77 (m, 4H) |
| 176 | 2-({4-amino-1-[(trans)-3-hydroxycyclobutyl]-1H-pyrazolo[3,4-d]pyrimidin-3-yl}oxy)pyridin-4-ol | 314.30 | 315 | (Methanol-d₄) δ = 8.31 (s, 1H), 7.97 (d, J = 5.6 Hz, 1H), 6.94 (d, J = 2.0 Hz, 1H), 6.75 (dd, J = 5.6, 2.0 Hz, 1H), 5.58-5.51 (m, 1H), 4.64-4.60 (m, 1H), 2.86-2.81 (m, 2H), 2.54-2.49 (m, 2H) |
| 177 | 2-({4-amino-1-[(trans)-3-fluorocyclobutyl]-1H-pyrazolo[3,4-d]pyrimidin-3-yl}oxy)pyridin-4-ol | 316.29 | 317 | (Methanol-d₄) δ = 8.32 (s, 1H), 7.98 (d, J = 5.6 Hz, 1H), 6.94 (d, J = 2.0 Hz, 1H), 6.75 (dd, J = 2.0, 6.0 Hz, 1H), 5.64-5.61 (m, 1H), 5.49-5.46 (m, 1H), 5.33-5.32 (m, 1H), 2.98-2.81 (m, 4H) |
| 178 | 3-((4-amino-1-((trans)-3-hydroxycyclobutyl)-1H-pyrazolo[3,4-d]pyrimidin-3-yl)oxy)benzonitrile | 322.3 | 323.1 | (Methanol-d₄) δ = 8.28 (s, 1H), 7.87 (d, J = 0.8 Hz, 1H), 7.82-7.78 (m, 1H), 7.67-7.63 (m, 2H), 5.51-5.43 (m, 1H), 4.58-4.52 (m, 1H), 2.80-2.72 (m, 2H), 2.48 (ddd, J = 4.4, 8.8, 13.2 Hz, 2H) |
| 179 | (trans)-3-(4-amino-3-(3-(trifluoromethyl)phenoxy)-1H-pyrazolo[3,4-d]pyrimidin-1-yl)cyclobutan-1-ol | 365.31 | 366.1 | (Methanol-d₄) δ = 8.28 (s, 1H), 7.84 (s, 1H), 7.77-7.72 (m, 1H), 7.67 (t, J = 8.0 Hz, 1H), 7.61-7.57 (m, 1H), 5.51-5.43 (m, 1H), 4.59-4.52 (m, 1H), 2.80-2.70 (m, 2H), 2.48 (ddd, J = 4.4, 8.8, 13.2 Hz, 2H) |
| 180 | 1-(4-amino-3-((4-(trifluoromethyl)pyridin-2-yl)oxy)-1H-pyrazolo[3,4-d]pyrimidin-1-yl)cyclobutane-1-carboxylic acid | 394.1 | 395.1 | (Methanol-d₄) δ = 8.44 (d, J = 5.2 Hz, 1H), 8.26 (s, 1H), 7.71 (s, 1H), 7.54 (d, J = 5.2 Hz, 1H), 3.15-3.01 (m, 2H), 2.94 (m, 2H), 2.40-2.29 (m, 1H), 2.16-2.04 (m, 1H) |

TABLE 16-continued

Further Compounds of the Invention

| Compound No. | IUPAC Name | Expected MW (M) | LC/MS Observed (M + H) | $^1$H NMR (400 MHz) |
|---|---|---|---|---|
| 181 | ethyl 1-(4-amino-3-((4-(trifluoromethyl)pyridin-2-yl)oxy)-1H-pyrazolo[3,4-d]pyrimidin-1-yl)cyclobutane-1-carboxylate | 422.13 | 423.1 | (Methanol-d$_4$) δ = 8.44 (d, J = 5.2 Hz, 1H), 8.27 (s, 1H), 7.70 (s, 1H), 7.56-7.53 (m, 1H), 4.19 (q, J = 7.2 Hz, 2H), 3.12-3.03 (m, 2H), 2.96-2.88 (m, 2H), 2.31 (m, 1H), 2.17-2.04 (m, 1H), 1.20 (t, J = 7.2 Hz, 3H) |
| 182 | 1-(1-(trifluoromethyl)cyclobutyl)-3-((4-(trifluoromethyl)pyridin-2-yl)oxy)-1H-pyrazolo[3,4-d]pyrimidin-4-amine | | | |
| 183 | 1-(1-(trifluoromethyl)cyclopropyl)-3-((4-(trifluoromethyl)pyridin-2-yl)oxy)-1H-pyrazolo[3,4-d]pyrimidin-4-amine | | | |

Example 3

Certain of the compounds prepared as described above were assayed to determine their IC$_{50}$ for inhibition of *T. gondii* CDPK1 (tgCDPK1). At least three independent replicates of the assay were conducted for each compound tested. The results are presented in Table 17 below. Compounds described herein that are selective for tgCDPK1 are expected to be selective for CDPK1 derived from the genera *Plasmodium* and *Cryptosporidium* as well.

TABLE 17

Potency of Exemplary Compounds against T. gondii CDPK1

| No. | Compound Name | tgCDPK1 IC$_{50}$ (nM) |
|---|---|---|
| 12 | 3-(4-chlorobenzyl)-1-cyclopropyl-1H-pyrazolo[3,4-d]pyrimidin-4-amine | 1830 |
| 23 | 3-(3-chlorobenzyl)-1-cyclopropyl-1H-pyrazolo[3,4-d]pyrimidin-4-amine | 17.2 |
| 9 | 3-([1,1'-biphenyl]-3-ylmethyl)-1-cyclopropyl-1H-pyrazolo[3,4-d]pyrimidin-4-amine | 26.3 |
| 10 | 1-cyclopropyl-3-(pyrimidin-5-yl)benzyl)-1H-pyrazolo[3,4-d]pyrimidin-4-amine | 373 |
| 11 | 1-cyclopropyl-3-(3-(pyridin-4-yl)benzyl)-1H-pyrazolo[3,4-d]pyrimidin-4-amine | 1170 |
| 4 | 3-(3-chloro-5-fluorobenzyl)-1-cyclopropyl-1H-pyrazolo[3,4-d]pyrimidin 4 amine | 91.7 |
| 5 | 1-cyclopropyl-3-(3-fluorobenzyl)-1H-pyrazolo[3,4-d]pyrimidin-4-amine | 25.3 |
| 6 | 3-(3-chlorobenzyl)-1-cyclobutyl-1H-pyrazolo[3,4-d]pyrimidin-4-amine | 8.70 |
| 16 | (4-amino-1-cyclopropyl-1H-pyrazolo[3,4-d]pyrimidin-3-yl)(phenyl)methanol | 1750 |
| 17 | 3-benzyl-1-cyclopropyl-1H-pyrazolo[3,4-d]pyrimidin-4-amine | 25.4 |
| 18 | (4-amino-1-cyclopropyl-1H-pyrazolo[3,4-d]pyrimidin-3-yl)(pyridin-3-yl)methanol | 4870 |
| 107 | 3-((4-chloropyridin-2-yl)oxy)-1-cyclobutyl-1H-pyrazolo[3,4-d]pyrimidin-4-amine | 6.16 |
| 135 | 3-(3-chlorobenzyl)-1-((cis)-3-fluorocyclobutyl)-1H-pyrazolo[3,4-d]pyrimidin-4-amine | 7.05 |
| 121 | 3-(3-chlorophenoxy)-1-cyclobutyl-1H-pyrazolo[3,4-d]pyrimidin-4-amine | 7.41 |
| 42 | 3-((4-chloropyridin-2-yl)oxy)-1-cyclopropyl-1H-pyrazolo[3,4-d]pyrimidin-4-amine | 8.37 |
| 124 | (trans)-3-(4-amino-3-(3-chlorobenzyl)-1H-pyrazolo[3,4-d]pyrimidin-1-yl)cyclobutan-1-ol | 8.87 |
| 109 | 1-cyclobutyl-3-((4-(trifluoromethyl)pyridin-2-yl)oxy)-1H-pyrazolo[3,4-d]pyrimidin-4-amine | 9.79 |
| 111 | 2-((4-amino-1-cyclobutyl-1H-pyrazolo[3,4-d]pyrimidin-3-yl)oxy)isonicotinonitrile | 10.2 |
| 131 | (cis)-3-(4-amino-3-(3-bromobenzyl)-1H-pyrazolo[3,4-d]pyrimidin-1-yl)cyclobutan-1-ol | 11.4 |
| 154 | (trans)-3-(4-amino-3-(3-chlorophenoxy)-1H-pyrazolo[3,4-d]pyrimidin-1-yl)cyclobutan-1-ol | 11.8 |
| 112 | 1-cyclobutyl-3-((4-methoxypyridin-2-yl)oxy)-1H-pyrazolo[3,4-d]pyrimidin-4-amine | 14.6 |
| 130 | (cis)-3-(4-amino-3-(3-chlorobenzyl)-1H-pyrazolo[3,4-d]pyrimidin-1-yl)cyclobutan-1-ol | 15.4 |
| 116 | (trans)-3-(4-amino-3-((4-chloropyridin-2-yl)oxy)-1H-pyrazolo[3,4-d]pyrimidin-1-yl)cyclobutan-1-ol | 15.4 |

TABLE 17-continued

Potency of Exemplary Compounds against T. gondii CDPK1

| No. | Compound Name | tgCDPK1 IC$_{50}$ (nM) |
|---|---|---|
| 77 | 1-cyclopropyl-3-((4-(trifluoromethyl)pyridin-2-yl)oxy)-1H-pyrazolo[3,4-d]pyrimidin-4-amine | 16.5 |
| 127 | (trans)-3-(4-amino-3-(3-bromobenzyl)-1H-pyrazolo[3,4-d]pyrimidin-1-yl)cyclobutan-1-ol | 18.4 |
| 54 | 1-cyclopropyl-3-((4-phenylpyridin-2-yl)oxy)-1H-pyrazolo[3,4-d]pyrimidin-4-amine | 18.9 |
| 83 | 1-cyclopropyl-3-((4-methylpyridin-2-yl)oxy)-1H-pyrazolo[3,4-d]pyrimidin-4-amine | 20.6 |
| 78 | 2-((4-amino-1-cyclopropyl-1H-pyrazolo[3,4-d]pyrimidin-3-yl)oxy)isonicotinonitrile | 21.7 |
| 88 | 1-cyclopropyl-3-((4-methoxypyridin-2-yl)oxy)-1H-pyrazolo[3,4-d]pyrimidin-4-amine | 25.4 |
| 113 | (trans)-3-(4-amino-3-((4-(trifluoromethyl)pyridin-2-yl)oxy)-1H-pyrazolo[3,4-d]pyrimidin-1-yl)cyclobutan-1-ol | 26.5 |
| 152 | (cis)-3-(4-amino-3-(3-chlorophenoxy)-1H-pyrazolo[3,4-d]pyrimidin-1-yl)cyclobutan-1-ol | 27.3 |
| 128 | (trans)-3-(4-amino-3-(3-fluorobenzyl)-1H-pyrazolo[3,4-d]pyrimidin-1-yl)cyclobutan-1-ol | 28.3 |
| 132 | (cis)-3-(4-amino-3-(3-fluorobenzyl)-1H-pyrazolo[3,4-d]pyrimidin-1-yl)cyclobutan-1-ol | 28.4 |
| 86 | (2-((4-amino-1-cyclopropyl-1H-pyrazolo[3,4-d]pyrimidin-3-yl)oxy)pyridin-4-yl)methanol | 29.6 |
| 151 | (cis)-3-(4-amino-3-(3-(trifluoromethyl)phenoxy)-1H-pyrazolo[3,4-d]pyrimidin-1-yl)cyclobutan-1-ol | 31.3 |
| 153 | (cis)-3-(4-ammo-3-(3-fluorophenoxy)-1H-pyrazolo[3,4-d]pyrimidin-1-yl)cyclobutan-1-ol | 33.8 |
| 125 | (trans)-3-(4-amino-3-(3-(trifluoromethyl)benzyl)-1H-pyrazolo[3,4-d]pyrimidin-1-yl)cyclobutan-1-ol | 36.0 |
| 38 | 1-cyclopropyl-3-(pyridin-2-yloxy)-1H-pyrazolo[3,4-d]pyrimidin-4-amine | 37.6 |
| 155 | (trans)-3-(4-amino-3-(3-fluorophenoxy)-1H-pyrazolo[3,4-d]pyrimidin-1-yl)cyclobulan-1-ol | 38.0 |
| 156 | 3-(3-chlorophenoxy)-1-[(1r,3r)-3-fluorocyclobutyl]-1H-pyrazolo[3,4-d]pyrimidin-4-amine | 10.0 |
| 157 | 3-[(5-fluoroindol-3-yl)methyl]-1-[(trans)-3-fluorocyclobutyl]-1H-pyrazolo[3,4-d]pyrimidin-4-amine | 11.0 |
| 158 | 3-[(4-chloropyridin-2-yl)oxy]-1-[(trans)-3-fluorocyclobutyl]-1H-pyrazolo[3,4-d]pyrimidin-4-amine | 11.4 |
| 159 | 1-cyclopropyl-3-{[4-(trifluoromethyl)pyridin-2-yl]oxy}-1H-pyrazolo[3,4-d]pyrimidin-4-amine | 13.0 |
| 160 | 2-({4-amino-1-cyclopropyl-1H-pyrazolo[3,4-d]pyrimidin-3-yl}oxy)pyridin-4-ol | 13.6 |
| 161 | 3-[(3-fluorophenyl)methyl]-1-[(trans)-3-fluorocyclobutyl]-1H-pyrazolo[3,4-d]pyrimidin-4-amine | 14.2 |
| 162 | 3-[(4-methoxypyridin-2-yl)oxy]-1-[(trans)-3-fluorocyclobutyl]-1H-pyrazolo[3,4-d]pyrimidin-4-amine | 17.4 |
| 163 | (cis)-3-{4-amino-3-[(4-chloropyridin-2-yl)oxy]-1H-pyrazolo[3,4-d]pyrimidin-1-yl}cyclobutan-1-ol | 18.0 |
| 164 | (trans)-3-{4-amino-5-[(3-fluorophenyl)methyl]-7H-pyrrolo[2,3-d]pyrimidin-7-yl}cyclobutan-1-ol | 28.3 |
| 165 | 1-cyclopropyl-3-[(4-cyclopropylpyridin-2-yl)oxy]-1H-pyrazolo[3,4-d]pyrimidin-4-amine | 28.9 |
| 166 | 1-[(trans)-3-fluorocyclobutyl]-3-[3-(trifluoromethyl)phenoxy]-1H-pyrazolo[3,4-d]pyrimidin-4-amine | 28.9 |
| 167 | 3-(3-fluorophenoxy)-1-[(trans)-3-fluorocyclobutyl]-1H-pyrazolo[3,4-d]pyrimidin-4-amine | 36.4 |
| 168 | (cis)-3-{4-amino-3-[(4-methoxypyridin-2-yl)oxy]-1H-pyrazolo[3,4-d]pyrimidin-1-yl}cyclobutan-1-ol | 37.1 |
| 169 | 1-cyclopropyl-3-([4-(trifluoromethoxy)pyridin-2-yl)oxy}-1H-pyrazolo[3,4-d]pyrimidin-4-amine | 37.7 |
| 170 | (cis)-3-(4-amino-3-{[4-(trifluoromethyl)pyridin-2-yl]oxy}-1H-pyrazolo[3,4-d]pyrimidin-1-yl)cyclobutan-1-ol | 38.6 |
| 171 | 3-(3-chlorophenoxy)-1-[(trans)-3-fluorocyclobutyl]-1H-pyrazolo[3,4-d]pyrimidin-4-amine | 41.1 |
| 172 | 3-({4-amino-1-[(trans)-3-fluorocyclobutyl]-1H-pyrazolo[3,4-d]pyrimidin-3-yl}methyl)benzonitrile | 45.9 |
| 173 | 3-({4-amino-1-[(trans)-3-fluorocyclobutyl]-1H-pyrazolo[3,4-d]pyrimidin-3-yl}oxy)benzonitrile | 49.8 |
| 174 | 2-({4-amino-1-[(trans)-3-fluorocyclobulyl]-1H-pyrazolo[3,4-d]pyrimidin-3-yl}oxy)pyridine-4-carboxamide | 69.7 |
| 175 | 3-[(4-methoxypyridin-2-yl)oxy]-1-[(trans)-3-fluorocyclobutyl]-1H-pyrazolo[3,4-d]pyrimidin-4-amine | 17.4 |
| 178 | 3-((4-amino-1-((trans)-3-hydroxycyclobutyl)-1H-pyrazolo[3,4-d]pyrimidin-3-yl)oxy)benzonitrile | 79.6 |
| 179 | (trans)-3-(4-amino-3-(3-(trifluoromethyl)phenoxy)-1H-pyrazolo[3,4-d]pyrimidin-1-yl)cyclobutan-1-ol | 47.9 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound having the structure of formula (I) or a pharmaceutically acceptable salt thereof:

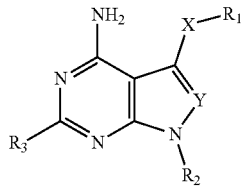
(I)

wherein:
X is $R^6$, O, S, $(NR^4)$, $OR^6$, $SR^6$, or $(NR^4)R^6$;
Y is N or CH;
$R^1$ is phenyl or 5-10 member heteroaryl;
$R^2$ is cyclopropyl or cyclobutyl, and is substituted with one or more $R^7$, wherein each $R^7$ is independently selected from haloalkyl, halogen, hydroxyl, oxo, alkoxy, cycloalkyloxy, cyano, and alkylthio;
$R^3$ is H, $C_{1-6}$ alkyl, $C_{1-6}$ haloalkyl, or $C_{3-6}$ cycloalkyl;
$R^4$ is H or $C_{1-6}$ alkyl; and
$R^6$ is $C_{1-6}$ alkylene or $C_{2-6}$ alkenylene.

2. The compound of claim 1, wherein X is $R^6$.
3. The compound of claim 1, wherein X is O.
4. The compound of claim 1, wherein $R^1$ is substituted with one or more $R^5$, and wherein each $R^5$ is independently selected from alkyl, trifluoromethyl, cycloalkyl, halogen, hydroxyl, oxo, alkoxy, cycloalkyloxy, amino, amidine, imine, cyano, azido, sulfhydryl, alkylthio, heterocyclyl, aryl, and heteroaryl.
5. The compound of claim 4, wherein $R^1$ is 3-chlorophenyl, 3-cyanophenyl, 3-fluorophenyl, 3-trifluoromethylphenyl or 3-methoxyphenyl.
6. The compound of claim 4, wherein $R^1$ is pyridin-2-yl substituted at the 4-position with $R^5$.
7. The compound of claim 6, wherein $R^5$ is trifluoromethyl, cyano, or hydroxyl.
8. The compound of claim 1, wherein $R^2$ is cyclopropyl and is substituted with one or more $R^7$.
9. The compound of claim 1, wherein $R^2$ is substituted by one or more $R^7$ selected from halogen.
10. The compound of claim 8, wherein $R^2$ is selected from hydroxycyclobutyl, fluorocyclobutyl, difluorocyclobutyl, oxocyclobutyl, hydroxycyclopropyl, fluorocyclopropyl, and difluorocyclopropyl.
11. The compound of claim 1, wherein $R^3$ is H.
12. The compound of claim 1, wherein $R^6$ is methylene, ethylene, or ethenylene.
13. The compound of claim 1, having the structure of formula (Ia) or a pharmaceutically acceptable salt thereof:

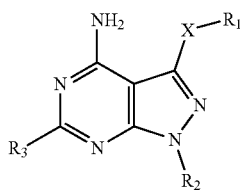
(Ia)

wherein:
X is $R^6$, O, S, or $(NR^4)$;
$R^1$ is phenyl optionally substituted with one or more $R^5$ independently selected from $C_{1-3}$ alkyl, $C_{1-3}$ haloalkyl, cyano, and halo;
$R^2$ is $C_{3-4}$ cycloalkyl substituted with one or more $R^7$ selected from hydroxyl and fluoro;
$R^3$ is H;
$R^4$ is H or $C_{1-6}$ alkyl; and
$R^6$ is $C_{1-3}$ alkylene.

14. The compound of claim 13, wherein the compound is:

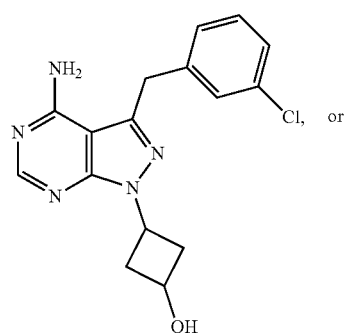

or

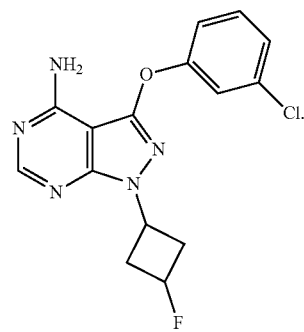

15. A compound having the structure of formula (Ib) or a pharmaceutically acceptable salt thereof:

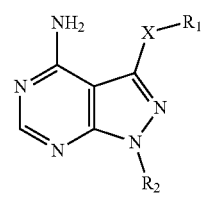
(Ib)

wherein:
X is $R^6$, O, S, or $(NR^4)$;
$R^1$ is pyridin-2-yl substituted at the 4-position with an $R^5$, selected from trifluoromethyl, hydroxyl, and cyano;
$R^2$ is substituted or unsubstituted $C_{3-4}$ cycloalkyl;
$R^4$ is H or $C_{1-6}$ alkyl; and
$R^6$ is $C_{1-3}$ alkylene.

16. The compound of claim 15, wherein X is O.

17. The compound of claim 15, wherein the compound is:

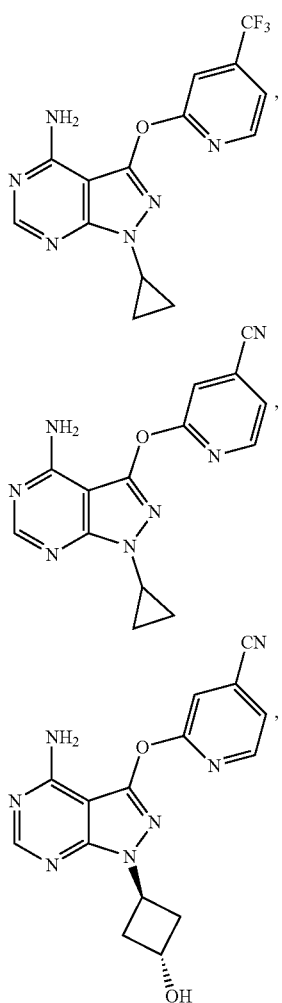

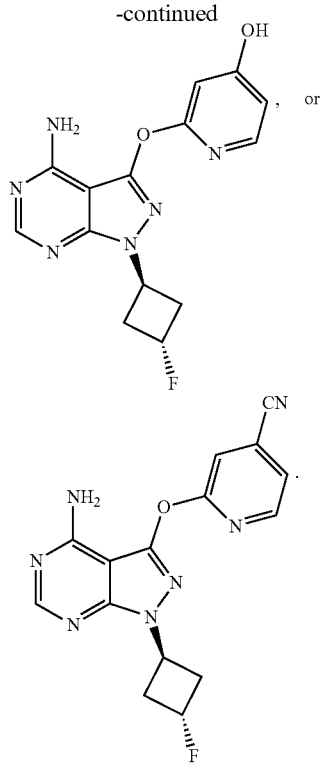

18. A pharmaceutical composition comprising a compound of claim 1 and a pharmaceutically acceptable excipient.

19. A pharmaceutical composition comprising a compound of claim 15 and a pharmaceutically acceptable excipient.

20. A method of treating an infection, comprising administering a compound or composition of claim 1.

21. The method of claim 20, wherein the infection is caused by protozoan.

* * * * *